United States Patent [19]

Sunagawa et al.

[11] Patent Number: 4,962,103

[45] Date of Patent: Oct. 9, 1990

[54] CARBAPENEM COMPOUNDS AND PRODUCTION THEREOF

[75] Inventors: Makoto Sunagawa, Osaka; Haruki Matsumura, Nara; Takaaki Inoue; Masamoto Fukasawa, both of Hyogo; Masuhiro Kato, Osaka, all of Japan

[73] Assignee: Sumitomo Pharmaceuticals Company, Limited, Osaka, Japan

[21] Appl. No.: 325,025

[22] Filed: Mar. 17, 1989

Related U.S. Application Data

[63] Continuation of Ser. No. 796,329, Nov. 8, 1985, abandoned.

[30] Foreign Application Priority Data

Nov. 8, 1984 [JP] Japan ............................ 59-234064
Jan. 7, 1985 [JP] Japan ............................ 60-577
Jan. 9, 1985 [JP] Japan ............................ 60-1925

[51] Int. Cl.$^5$ .................. C07D 487/04; A61K 31/40
[52] U.S. Cl. .................................. 514/210; 540/350
[58] Field of Search ..................... 540/350; 514/210

[56] References Cited

FOREIGN PATENT DOCUMENTS 0010317  4/1980  European Pat. Off. ............ 540/350
0071908  2/1983  European Pat. Off. ............ 540/350
0072710  2/1983  European Pat. Off. ............ 540/350
0089139  9/1983  European Pat. Off. ............ 540/350

OTHER PUBLICATIONS

"Synthesis and in vitro Activity of a New Carbapenem, RS-533", *The Journal of Antibiotics*, pp. 1034–1039.
"Synthetic Carbapenem Antibiotics I.1-β-methylcarbapenem", *Heterocycles*, pp. 29–40.

*Primary Examiner*—Robert Gerstl
*Attorney, Agent, or Firm*—Birch, Stewart, Kolasch & Birch

[57] ABSTRACT

A compound of the formula:

wherein $R_1$ is a hydrogen atom or a lower alkyl group, $R_2$ is a hydrogen atom or a conventional protecting group for a carboxyl group, $R_0$ is a hydrogen atom or a conventional protecting group for a hydroxyl group, X is a protected or unprotected amino group, a carboxyl group, a lower alkoxycarbonyl group, an ar(lower)alkyloxycarbonyl group, a cyano group, a hydroxyl group, a lower alkyloxy group, a lower alkylthio group, a lower alkylsulfonyl group or a group of either one of the following formulas:

$$-CON\begin{matrix}R_3\\R_4\end{matrix} \quad (1)$$

wherein $R_3$ and $R_4$, which may be the same or different, each represents a hydrogen atom or a lower alkyl group, or they are taken together to represent an alkylene chain to form, in combination with the adjacent nitrogen atom, a 3- to 7-membered cyclic amino group, $$-ZCOR_5 \quad (2)$$

wherein Z represents —NH— or —O— and $R_5$ represents an amino group, a mono(lower)alkylamino group, a di(lower)alkylamino group, a lower alkyloxy group or a lower alkyl group, $$-NH-\underset{R_6}{C}=NH \quad (3)$$

wherein $R_6$ represents a hydrogen atom or a lower alkyl group, $$-CH=N-R_7 \quad (4)$$

wherein $R_7$ represents a mono(lower)alkylamino group, a di(lower)alkylamino group or a lower alkyloxy group, or $$-CO-N-N\begin{matrix}R_9\\R_{10}\end{matrix}\\ \phantom{-CO-N}R_8 \quad (5)$$

wherein $R_8$, $R_9$ and $R_{10}$, which may be the same or different, each represents a hydrogen atom or a lower alkyl group, Y represents a hydrogen atom, a conventional protecting group for an amino group or a group of either one of the following formulas:

$$-CON\begin{matrix}R_{11}\\R_{12}\end{matrix} \quad (6)$$

wherein $R_{11}$ and $R_{12}$, which may be the same or different, each represents a hydrogen atom or a lower alkyl group or $$-\underset{R_6}{C}=NH \quad (7)$$

wherein $R_6$ is as defined above and n is an ingeter of 1 to 6, and a pharmacologically acceptable salt thereof, which is useful as an antimicrobial agent.

29 Claims, No Drawings

CARBAPENEM COMPOUNDS AND PRODUCTION THEREOF

This application is a continuation of application Ser. No. 796,329, filed on Nov. 8, 1985, now abandoned.

The present invention relates to novel carbapenem compounds useful as antimicrobial agents or intermediates therefor, and their production.

Since the discovery of thienamycin having a potential antimicrobial activity against Gram-negative and Gram-positive bacteria, studies on the syntheses of carbapenem derivatives which are analogous to thienamycin have been widely developed. As a result, it has now been found that carbapenem derivatives having, as their 2-side chain, a substituent easily derived from 4-hydroxy-proline, i.e. a pyrrolidinyl group substituted on its 2-position, exhibit a potential antimicrobial activity and are useful as medicines or as intermediates for antibiotic substances.

This invention provides novel carbapenem compounds of the formula (I):

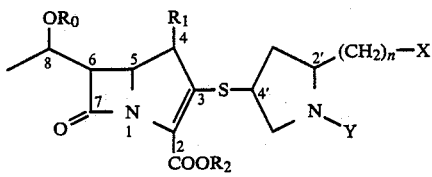

wherein $R_1$ is a hydrogen atom or a lower alkyl group;

$R_2$ is a hydrogen atom or a conventional protecting group for a carboxyl group;

$R_0$ is a hydrogen atom or a conventional protecting group for a hydroxyl group;

X is a protected or unprotected amino group, a carboxyl group, a lower alkoxycarbonyl group, an ar(-lower)alkyloxycarbonyl group such as phenyl(lower)alkyloxycarbonyl, a cyano group, a hydroxyl group, a lower alkyloxy group, a lower alkylthio group, a lower alkylsulfonyl group or a group of either one of the following formulas:

      (1)

wherein $R_3$ and $R_4$, which may be the same or different, each represent a hydrogen atom or a lower alkyl group, or they are taken together to represent an alkylene chain to form, in combination with the adjacent nitrogen atom, a 3- to 7-membered cyclic amino group, $$-ZCOR_5 \quad (2)$$

wherein Z represents —NH— or —O— and $R_5$ represents an amino group, a mono(lower)alkylamino group, a di(lower)alkylamino group, a lower alkyloxy group or a lower alkyl group,

      (3)

wherein $R_6$ represents a hydrogen atom or a lower alkyl group,

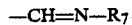      (4)

wherein $R_7$ represents a mono(lower)alkylamino group, a di(lower)alkylamino group or a lower alkyloxy group, or

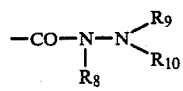      (5)

wherein $R_8$, $R_9$ and $R_{10}$, which may be the same or different, each represent a hydrogen atom or a lower alkyl group;

Y is a hydrogen atom, a conventional protecting group for an amino group or a group of either one of the following formulas:

      (6)

wherein $R_{11}$ and $R_{12}$, which may be the same or different, each represent a hydrogen atom or a lower alkyl group, or

      (7)

wherein $R_6$ is as defined above; and n is an integer of 1 to 6.

The present invention also provides the pharmacologically acceptable salts of the carbapenem compounds (I).

In the above formula (I), the term "lower" as used in connection with any group is intended to mean generally a group having not more than 8 carbon atoms, particularly not more than 5 carbon atoms, unless otherwise defined. For instance, specific examples of lower alkyl are methyl, ethyl, n-propyl, isopropyl, n-butyl, sec-butyl, t-butyl, etc. Further, for instance, specific examples of lower alkyloxy are methoxy, ethoxy, n-propoxy, isopropoxy, n-butoxy, sec-butoxy, t-butoxy, etc.

The protecting group for a hydroxyl group as represented by $R_0$ may be any of those commonly employed, and its preferred examples are $C_1$-$C_4$ alkoxycarbonyl (e.g. t-butyloxycarbonyl), halo($C_1$-$C_3$)alkoxycarbonyl (e.g. 2-iodoethyloxycarbonyl, 2,2,2-trichloroethyloxycarbonyl), substituted or unsubstituted ar(lower)alkyloxycarbonyl such as substituted or unsubstituted phenyl($C_1$-$C_3$)alkyloxycarbonyl (e.g. benzyloxycarbonyl, p-methoxybenzyloxycarbonyl, o-nitrobenzyloxycarbonyl, p-nitrobenzyloxycarbonyl), tri($C_1$-$C_4$)alkylsilyl (e.g. trimethylsilyl, t-butyldimethylsilyl), etc.

The protecting group for a carboxyl group as represented by $R_2$ may be any of those commonly employed, and its preferred examples include $C_1$-$C_4$ alkyl (e.g. methyl, ethyl, isopropyl, t-butyl), halo($C_1$-$C_3$)alkyl (e.g. 2-iodoethyl, 2,2,2-trichloroethyl), $C_1$-$C_4$ alkoxymethyl (e.g. methoxymethyl, ethoxymethyl, isobutoxymethyl), $C_1$-$C_8$ aliphatic acyloxymethyl (e.g. acetoxymethyl, propionyloxymethyl, butyryloxymethyl, pivaloyloxymethyl), 1-($C_1$-$C_4$)alkoxycarbonyloxyethyl (e.g. 1-methoxycarbonyloxyethyl, 1-ethoxycorbonyloxyethyl), substituted or unsubstituted ar(lower)alkyl such as substituted or unsubstituted phenyl($C_1$-$C_3$)alkyl (e.g. benzyl, p-methoxybenzyl, o-nitrobenzyl, p-nitrobenzyl), benzhydryl, phthalidyl, etc.

In the definitions for $R_1$, X and Y, the term "lower" is preferred to mean any group having not more than 3 carbon atoms. For instance, examples of lower alkyl are methyl, ethyl, n-propyl and isopropyl.

When X is the group (1), $R_3$ and $R_4$ may be the same or different from each other. In the definitions for $R_3$ and $R_4$, the lower alkyl group represents preferably the one having not more than 4 carbon atoms (e.g. methyl, ethyl, n-propyl, isopropyl, n-butyl, t-butyl).

In the case where $R_3$ and $R_4$ jointly represent an alkylene chain to form, in combination with the adjacent nitrogen atom, a 3- to 7-membered cyclic amino group, specific examples include a saturated cyclic amino group (e.g. aziridino, azetidino, pyrrolidino, piperidino).

The lower alkoxycarbonyl group for X includes, for example, $C_1$-$C_4$ alkoxycarbonyl such as methoxycarbonyl, ethoxycarbonyl and isopropoxycarbonyl. The ar(lower)alkyloxycarbonyl group for X includes, for example, substituted or unsubstituted ar(lower)alkyloxycarbonyl such as benzyloxycarbonyl, p-methoxybenzyloxycarbonyl, p-nitrobenzyloxycarbonyl and o-nitrobenzyloxycarbonyl.

When Y is the group (6), the lower alkyl group represented by $R_{11}$ or $R_{12}$ is preferred to have 1 to 4 carbon atoms and may be, for instance, methyl, ethyl, n-propyl, isopropyl, n-butyl, t-butyl, etc.

The protecting group for an amino group as represented by Y or used in the protected amino group of X may be any of those commonly employed. Preferred examples are $C_1$-$C_4$ alkoxycarbonyl (e.g. t-butyloxycarbonyl), halo($C_1$-$C_3$)alkoxycarbonyl (e.g. 2-iodoethyloxycarbonyl, 2,2,2-trichloroethyloxycarbonyl), substituted or unsubstituted ar(lower)alkyloxycarbonyl such as substituted or unsubstituted phenyl($C_1$-$C_3$)alkyloxycarbonyl (e.g. benzyloxycarbonyl, p-methoxybenzyloxycarbonyl, o-nitrobenzyloxycarbonyl, p-nitrobenzyloxycarbonyl), tri($C_1$-$C_4$)alkylsilyl (e.g. trimethylsilyl, t-butyldimethylsilyl), etc.

The carbapenem compounds (I) wherein —COOR$_2$ or X represents a carboxyl group may be converted into their pharmacologically acceptable salts, if desired. Specific examples of such salts are inorganic metal salts (e.g. lithium salt, sodium salt, potassium salt, calcium salt, magnesium salt), ammonium salts (e.g. ammonium salt, cyclohexylammonium salt, diisopropylammonium salt, triethylammonium salt), etc., among which sodium salt and potassium salt are the most preferred. The carbapenem compounds (I) wherein X represents an amino group or a group of the formula (3) or Y represents a hydrogen atom or a group of the formula (7) may be also converted into their pharmacologically acceptable salts, if desired. Examples of such salts are those with mineral acids such as hydrochloric acid and sulfuric acid.

Among the carbapenem compounds (I) of the invention, preferred are those of the formula (I-a):

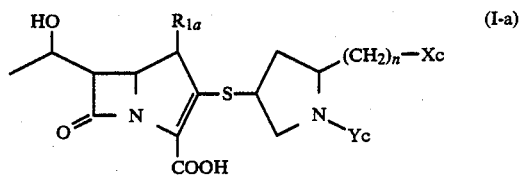

wherein $R_{1a}$ is a hydrogen atom or a lower alkyl group, Xc is either one of the groups (1) to (5), an amino group, a carboxyl group, a lower alkoxycarbonyl group, a cyano group, a hydroxyl group, a lower alkoxy group, a lower alkylthio group or a lower alkylsulfonyl group, Yc is a hydrogen atom or either one of the groups (6) and (7) and n is an integer of 1 to 6.

Particularly preferred are the carbapenem compounds of the formula (I-b):

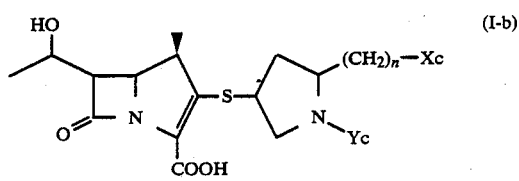

wherein Xc and Yc are each as defined above.

Preferred examples of the substituent: —(CH$_2$)$_n$—Xc at the 2-position of the pyrrolidinyl group include those of the following formulas (a) to (e):

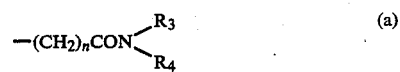

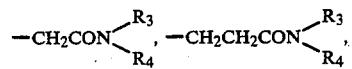

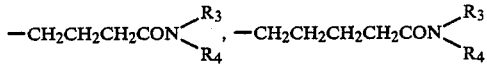

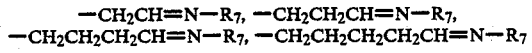

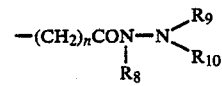

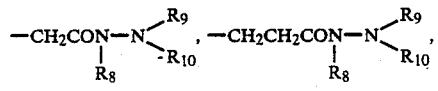

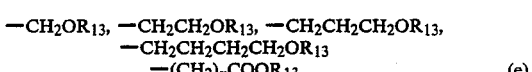

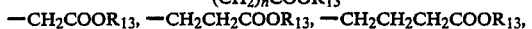

-continued

—CH₂CH₂CH₂CH₂COOR₁₃ wherein $R_3$, $R_4$, $R_7$, $R_8$, $R_9$ and $R_{10}$ are each as defined above and $R_{13}$ represents a hydrogen atom or a lower alkyl group, the groups (a) and (d) being particularly favorable.

The carbapenem compounds (I) can be produced by various procedures, among which some typical ones are set forth below.

(A) The carbapenem compound of the formula (II):

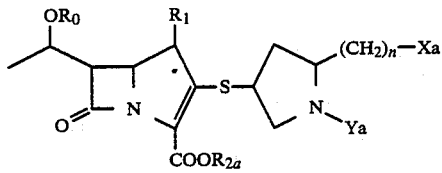

wherein $R_0$, $R_1$ and n are each as defined above, $R_{2a}$ is a protecting group for a carboxyl group, Xa is either one of the groups (1), (2), (4) and (5), a protected amino group, a lower alkoxycarbonyl group, an ar(lower)alkyoxycabonyl group, a cyano group, a hydroxyl group, a lower alkyloxy group, a lower alkylthio group or a lower alkylsulfonyl group and Ya is a protecting group for an amino group or the group (6), is prepared by reacting the carbapenem compound of the formula (III):

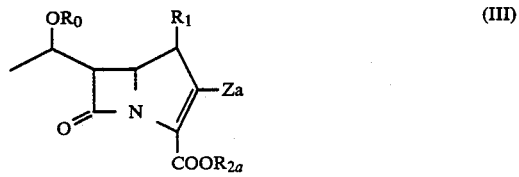

wherein $R_0$, $R_1$ and $R_{2a}$ are each as defined above and Za is a reactive ester group with a mercaptan of the formula (IV):

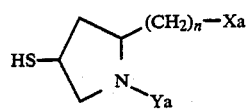

wherein Xa, Ya and n are each as defined above, in an inert solvent in the presence of a base.

The term "reactive ester group" herein used is intended to mean a leaving group such as a halide or a sulfonate. It may be the residue of a substituted or unsubstituted arylsulfonate, a lower alkanesulfonate, a halo(lower)alkanesulfonate, a diarylphosphoric acid ester, a halide or the like. Examples of the substituted or unsubstituted arylsulfonate are benzenesulfonate, p-toluenesulfonate, p-nitrobenzenesulfonate, p-bromobenzenesulfonate, etc. Examples of the lower alkanesulfonate are methanesulfonate, ethanesulfonate, etc. Examples of the halo(lower)alkanesulfonate are trifluoromethanesulfonate, etc. As the diarylphosphoric acid ester, there may be exemplified diphenylphosphoric acid ester, etc. The halide includes, for example, chloride, bromide, iodide, etc. Of these reactive esters, preferred are p-toluenesulfonate, methanesulfonate, diphenylphosphoric acid ester, etc.

The protecting group for a carboxyl group as represented by $R_{2a}$ corresponds to the one as represented by $R_2$, and the same preferred groups as enumerated for $R_2$ can also be applied to $R_{2a}$.

In the process, the carbapenem compound (III) and the mercaptan (IV) are reacted normally by the use of a large excessive amount, particularly from 1 to 1.5 equivalents, of the latter to the former.

As the inert solvent, there may be used dioxane, tetrahydrofuran, dimethylformamide, dimethylsulfoxide, acetonitrile, hexamethylphosphoramide, etc. Their mixtures are also usable. Among them, acetonitrile, dimethylformamide, etc. are preferred. Examples of the base include inorganic bases (e.g. sodium carbonate, potassium carbonate, sodium hydride, potassium hydride, potassium t-butoxide) and organic bases (e.g. pyridine, 4-dimethylaminopyridine, triethylamine, diisopropylethylamine), among which organic bases are preferred. The base may be used in such an amount as sufficient to promote the reaction and usually from 1 to 1.5 equivalents per mol of the mercaptan (IV).

The reaction can be carried out at a temperature of from about −78° to 60° C., preferably from −40° to 40° C.

Recovery of the reaction product from the reaction mixture may be accomplished by a per se conventional procedure, for instance, by washing the reaction mixture with water, drying and evaporating the solvent. The reaction product may, if necessary, be further purified by a per se conventional means, for example, by recrystallization, preparative thin layer chromatography, column chromatography or the like.

The thus obtained carbapenam compound (II) may be subjected, if necessary, to reaction for removal of the hydroxyl-protecting group on $R_0$, removal of the amino-protecting group on Ya, removal of the carboxyl-protecting group on $R_{2a}$ and/or removal of the protecting group on Xa to obtain the carbapenem compound (I). Removal of the protecting group may be achieved by adoption of an appropriate per se conventional procedure depending upon the type of the protecting group. For instance, the carbapenem compound (II) bearing a halo(lower)alkoxycarbonyl group or an ar(lower)alkyloxycarbonyl group as the hydroxyl-protecting group or the amino-protecting group or a halo(lower)alkyl group, an ar(lower)alkyl group or a benzhydryl group as the carboxyl-protecting group may be subjected to reduction for removal of any of those protecting groups. The reduction is preferably carried out, for instance, by treatment with zinc in an organic solvent (e.g. acetic acid, tetrahydrofuran, methanol) when the protecting group is a halo(lower)alkoxycarbonyl group or a halo(lower)alkyl group, or by catalytic reduction using a catalyst (e.g. platinum, palladium-on-carbon) when the protecting group is an ar(lower)alkyloxycarbonyl group, an ar(lower)alkyl group or a benzhydryl group. The catalytic reduction is usually effected in any liquid medium chosen from organic solvents such as lower alcohols (e.g. methanol, ethanol), ethers (e.g. tetrahydrofuran, dioxane) and acetic acid or from their mixtures with water or buffer solutions (e.g. phosphoric acid, morpholinopropanesulfonic acid). The reduction is normally conducted at a temperature of from about 0° to 100° C., preferably from about 0° to 40° C., in a hydrogen atmosphere under the atmospheric or an elevated pressure.

When the protecting group is an o-nitrobenzyl group or an o-nitrobenzyloxycarbonyl group, it can also be removed by photo-reaction.

(B) The carbapenem compound of the formula (V):

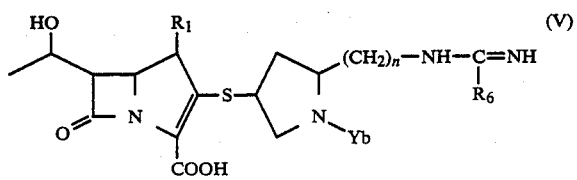

wherein $R_1$ and n are each as defined above, $R_6$ is a hydrogen atom or a lower alkyl group and Yb is the group (6) can be prepared by reacting the carbapenem compound of the formula (VI):

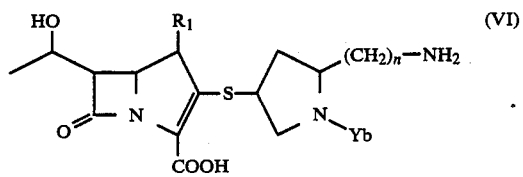

wherein $R_1$, Yb and n are each as defined above with an imidate of the formula (8):

wherein $R_6$ is as defined above and $R_{14}$ represents a lower alkyl group or a benzyl group, or a salt thereof under a basic condition.

In the formula (8), the lower alkyl group for $R_{14}$ may be preferably alkyl of 1 to 5 carbon atoms (e.g. methyl, ethyl, n-propyl, isopropyl, n-butyl, isobutyl). As the salt of the imidate (8), there are exemplified hydrohalides such as hydrochloride, hydrobromide and hydroiodide.

The reaction is normally effected under a basic condition at a pH ranging from about 8 to 14, preferably from about 9 to 10. Such basic condition may be prepared by the use of an alkali metal hydroxide (e.g. sodium hydroxide, potassium hydroxide), an alkaline earth metal hydroxide (e.g. calcium hydroxide, barium hydroxide), an alkali metal carbonate (e.g. sodium carbonate, potassium carbonate), etc. The reaction is preferably carried out in water, but can be done in a mixed solvent of water with an organic solvent chosen from lower alcohols (e.g. methanol, ethanol, n-propanol), ethers (e.g. tetrahydrofuran, dioxane), dimethylformamide, acetonitrile, etc. The reaction temperature is preferred to be from 0° C. to room temperature, but the reaction rate may be suppressed or promoted by cooling or heating if necessary.

Separation of the reaction product from the reaction mixture may be accomplished by a per se conventional procedure. For example, the reaction mixture is neutralized with a conventional acid (e.g. hydrochloric acid, sulfuric acid) and purified by column chromatography on an adsorbent to give a fraction containing the desired product. Concentration or lyophilization of the fraction affords the reaction product.

(C) The carbapenem compound of the formula (VII):

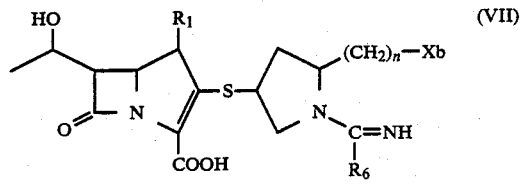

wherein $R_1$, $R_6$ and n are each as defined above, Xb is either one of the groups (1), (2), (4) and (5), a carboxyl group, a lower alkoxycarbonyl group, a cyano group, a hydroxyl group, a lower alkyloxy group, a lower alkylthio group or a lower alkylsulfonyl group, can be prepared by reacting a carbapenem compound of the formula (VIII):

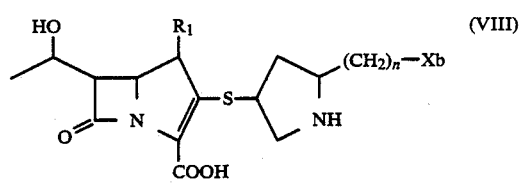

wherein $R_1$, Xb and n are each as defined above with the imidate (8) or its salt under a basic condition by the same procedure as (B).

In the carbapenem compounds (I), asymmetric carbon atoms are present at the 5-, 6- and 8-positions. The carbon atoms at the 2'- and 4'-positions in the 2-side chain are also asymmetric. Further, when $R_1$ is an alkyl group, the carbon atom at the 4-position is asymmetric. Therefore, the carbapenem compounds (I) have optical isomers and steric isomers due to these asymmetric carbon atoms. Although all of these isomers are represented by a respective single formula for the sake of convenience, the scope of the invention extends to and covers all of them.

Among those isomers, preferred are the ones having the same relative-configuration as thienamycin on the carbon atom at the 5-position. The compounds wherein $R_1$ is an alkyl group and which have a 5S-configuration, i.e. the (5S,6S)- or (5S,6R)-compounds, are preferred. The compounds wherein $R_1$ is a hydrogen atom and which have a 5R-configuration, i.e. the (5R,6S)- or (5R,6R)-compounds, are favorable. With respect to the carbon atom at the 8-position, those having an R-configuration are preferred. With respect to the 4-position, the compounds wherein $R_1$ is an alkyl group and which have an R-configuration, i.e. the (4R)-compounds, are favorable.

More preferred are the compounds (I) wherein $R_1$ is an alkyl group and which have a (4R,5S,6S,8R)-configuration, the compounds (I) wherein $R_1$ is a hydrogen atom and which have a (4R,5R,6S,8R)-configuration, etc.

The most preferred compounds include those of the formulas:

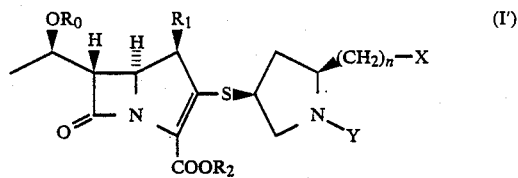

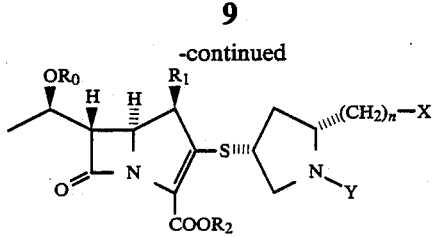

(I")

wherein $R_0$, $R_1$, $R_2$, X, Y, and n are each as defined above.

The isomers having the steric configurations as stated above can be prepared from the starting compounds (III) or (IV) having the corresponding configurations.

The starting compounds (III) can be prepared by various conventional methods. The compounds (III) wherein $R_1$ is a hydrogen atom are known per se in (1) Japanese Patent Publication (unexamined) No. 27169/80, (2) J. Am. Chem. Soc., Vol. 103, 6765-6767 (1981), (3) J. Chem. Soc., Perkin I, 964-968 (1981), etc. and can be produced by the methods as described in said literatures (1) to (3). The compounds (III) wherein $R_1$ is a lower alkyl group are known per se in (4) Heterocycles, Vol. 21, 29-40 (1984), (5) EP-A-No. 0071908, (6) EP-A-No. 0126587, etc. and can be produced according to the methods as described in the literature articles (4) to (6).

The starting mercaptan derivatives (IV) can be prepared from trans-4-hydroxy-L-proline or cis-4-hydroxy-D-proline by application of a series of per se conventional reactions thereto.

Of the carbapenem compounds (I), those wherein $R_0$ and $R_2$ are all hydrogen atoms exhibit an excellent antimicrobial activity against a wide variety of disease-causing bacteria including Gram-positive bacteria such as *Staphylococcus aureaus, Staphylococcus epidermidis, Streptococcus pyrogenes* and *Streptococcus faecalis* and Gram-negative bacteria such as *Escherichia coli, Proteus mirabilis, Serratia marcescens* and *Psudomonas aeruginosa* and are useful as antimicrobial agents. Further, these compounds are characteristic in exhibiting an excellent antimicrobial activity against beta-lactamase-producing strains.

Other compounds according to the invention are important intermediates for the synthesis of the carbapenem compounds having an antimicrobial activity.

The compounds according to the invention are also characterized in general by their high physiochemical stability and excellent water solubility, although some variation is observed depending on the respective compounds.

Carbapenem compounds including thienamycin are known to have very poor stability in the human body, especially to dehydropeptidase (DHP-I) existing in a part of renal. The compounds of invention, particularly those represented by the formula (I) wherein $R_1$ is a (R)-methyl group, are also characterized in general by their high stability to said enzyme DHP-I, although varying depending on the respective compounds. Some of the compounds of the invention have extremely high stability.

The compounds of the present invention can be used as antimicrobial agents for treating bacteria-caused infectious diseases in the form of oral preparations such as tablets, capsules, powders, syrups, etc. or non-oral preparations such as intravenous injections, intramuscular injections, rectal preparations, etc.

The dosage of the antimicrobial agent varies depending upon the symptoms, ages, bodyweight, dosage forms, times of doses and the like, but usually ranges from about 100 mg to 3,000 mg per day in a single dose or several divided doses for adults. The above dose level can be increased or decreased according to necessity.

The present invention will now be illustrated in greater detail with reference to the following Reference Examples and Examples, but it should be understood that these examples are given only for illustrative purposes and are not limiting the present invention.

In Reference Examples and Examples, the following abbreviations are used:

PNZ: p-Nitrobenzyloxycarbonyl group
PMZ: p-Methoxybenzyloxycarbonyl group
PMB: p-Methoxybenzyl group
PNB: p-Nitrobenzyl group
Ph: Phenyl group
Ac: Acetyl group
Ms: Methanesulfonyl group
Ts: p-Toluenesulfonyl group
TBDMS: t-Butyldimethylsilyl group
tBu: t-Butyl group
Me: Methyl group
Et: Ethyl group

REFERENCE EXAMPLE 1

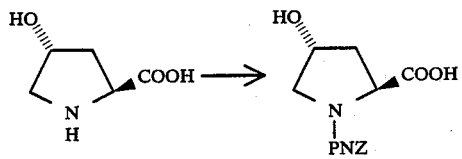

Trans-4-Hydroxy-L-proline (6.55 g) and triethylamine (7.5 ml) were dissolved in 15 ml of water, and a solution of 15.95 g of S-p-nitrobenzyloxycarbonyl-4,6-dimethyl-2-mercaptopyrimidine in 35 ml of dioxane was dropwise added thereto. The resulting mixture was stirred at room temperature for 1.5 hours and allowed to stand overnight. To the reaction mixture was added 30 ml of 2N sodium hydroxide solution under ice-cooling, and the resultant mixture was shaken with diethyl ether. The aqueous layer was separated from the ethereal layer, the ethereal layer was washed with 20 ml of 1m hydroxide solution, and the washing was combined with the aqueous layer. The combined mixture was made acidic with 100 ml of 2N hydrochloric acid and extracted with ethyl acetate. The ethyl acetate extract was washed with 2N hydrochloric acid, dried over anhydrous sodium sulfate and distilled to remove the solvent. The resulting crude crystals were washed with ethyl acetate to obtain trans-1-(p-nitrobenzyloxycarbonyl)-4-hydroxy-L-proline. M.P., 134.3°-135.5° C.

IR $max^{Nujol}$ cm$^{-1}$: 3300 (br), 1738, 1660, 1605, 1520, 1340, 1205, 1172, 1070, 965.

REFERENCE EXAMPLE 2

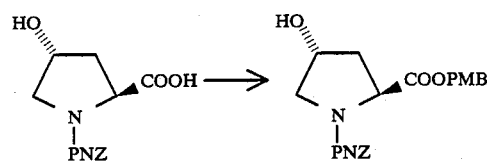

Trans-1-(p-Nitrobenzyloxycarbonyl)-4-hydroxy-L-proline (15.0 g) and triethylamine (13.5 ml) were dissolved in 150 ml of dry dimethylformamide, and 12.66 ml of p-methoxybenzyl chloride was dropwise added thereto under nitrogen stream, followed by stirring at 70° C. for 10 hours. The reaction mixture was diluted with 500 ml of ethyl acetate, washed with water, dried over anhydrous sodium sulfate and distilled to remove the solvent. Recrystallization of the residue from diethyl ether gave trans-1-(p-nitrobenzyloxycarbonyl)-4-hydroxy-L-proline p-methoxybenzyl ester. M.P., 83°–85° C.

IR $_{max}^{film}$ cm$^{-1}$: 3430, 1735, 1705, 1510, 1340, 1245, 1160.

In the same procedure as described above but using the corresponding acid, the p-methoxybenzyl ester derivatives as shown in Table 1 were obtained.

TABLE 1

| No. | n | Structure | Physical data |
|---|---|---|---|
| 1 | 1 | HO⋯[pyrrolidine]-(CH$_2$)$_n$COOPMB, N-PNZ | IR$_{max}^{neat}$ cm$^{-1}$: 1695, 1606, 1518, 1400, 1360, 1240, 1107 |
| 2 | 2 | | IR$_{max}^{neat}$ cm$^{-1}$: 1725, 1700, 1608, 1516, 1425, 1400, 1345 |
| 3 | 3 | | IR$_{max}^{neat}$ cm$^{-1}$: 1720, 1688, 1515, 1400, 1343 |
| 4 | | HO⋯[pyrrolidine]-CH$_2$COOPNB, N-PNZ | IR$_{max}^{neat}$ cm$^{-1}$: 1740, 1702, 1523, 1405, 1345 |
| 5 | | AcS⋯[pyrrolidine]-(CH$_2$)$_2$COOPNB, N-PNZ | IR$_{max}^{neat}$ cm$^{-1}$: 1732, 1697, 1515, 1393, 1342 |

REFERENCE EXAMPLE 3

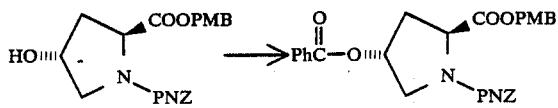

Trans-1-(p-Nitrobenzyloxycarbonyl)-4-hydroxy-L-proline p-methoxybenzyl ester (49 g) was dissolved in 300 ml of dry tetrahydrofuran, and 33 ml of triethylamine, 9.59 g of 4-dimethylaminopyridine and 33.2 g of benzoyl chloride were added thereto, followed by stirring under reflux for 5 hours. The reaction mixture was cooled down to room temperature and distilled to remove the solvent. The residue was diluted with ethyl acetate, washed successively with water, dilute hydrochloric acid, water, a saturated sodium bicarbonate solution and water, dried over anhydrous sodium sulfate and distilled to remove the solvent. Recrystallization of the residue from diethyl ether gave trans-1-(p-nitrobenzyloxycarbonyl)-4-benzoyloxy-L-proline p-methoxybenzyl ester.

IR $_{max}^{Nujol}$ cm$^{-1}$: 1740, 1716, 1703, 1608, 1516, 1343.

REFERENCE EXAMPLE 4

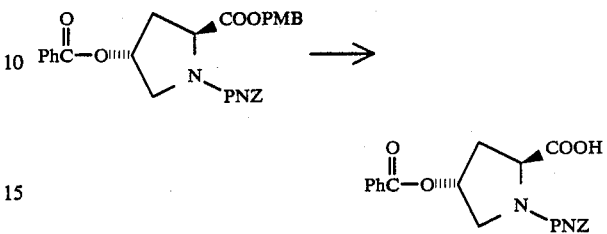

Trans-1-(p-Nitrobenzyloxycarbonyl)-4-benzoyloxy-L-proline p-methoxybenzyl ester (61.3 g) and anisole (12.8 ml) were stirred together with 70 ml of trifluoroacetic acid at room temperature for 30 minutes. The reaction mixture was distilled to remove tri-fluoroacetic acid, and the residue was diluted with ethyl acetate and a saturated sodium bicarbonate solution. The precipitated crystals were separated by filtration and dissolved in methanol. The solution was acidified with 6N hydrochloric acid to pH 1.0, diluted with ethyl acetate, washed with water and dried over anhydrous sodium sulfate. The solvent was removed by distillation to give trans-1-(p-nitrobenzyloxycarbonyl)-4-benzoyloxy-L-proline.

IR $_{max}^{CHCl_3}$ cm$^{-1}$: 1720, 1610, 1527, 1436, 1350, 1275, 1114.

In the same procedure as described above but using the corresponding p-methoxybenzyl ester, the acid derivatives as shown in Table 2 were obtained.

TABLE 2

| No. | n | Physical data |
|---|---|---|
| 1 | 1 | IR$_{max}^{neat}$ cm$^{-1}$: 1690, 1602, 1517, 1400, 1342, 1108 |
| 2 | 2 | IR$_{max}^{neat}$ cm$^{-1}$: 1690, 1600, 1510, 1420, 1393, 1338 |
| 3 | 3 | IR$_{max}^{neat}$ cm$^{-1}$: 1703, 1528, 1410, 1350, 1110 |

(structure: AcS⋯[pyrrolidine]-(CH$_2$)$_n$COOH, N-PNZ)

REFERENCE EXAMPLE 5

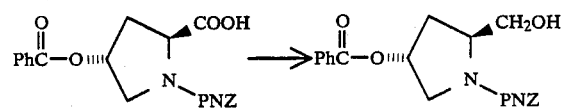

Trans-1-(p-Nitrobenzyloxycarbonyl)-4-benzolyloxy-L-proline (43.1 g) was dissolved in 86 ml of dry tetrahydrofuran, 12.2 g of triethylamine was added thereto. Ethyl chloroformate (13.0 g) was dropwise added to the mixture at −10° to −15° C. under nitrogen stream, followed by stirring for 15 minutes at the same temperature. The reaction mixture was separated by filtration, and the filtrate was added to a solution of 7.68 g of sodium borohydride in 78 ml of water at 0° C. After stirring for 1 hour at the same temperature, the reaction mixture was diluted with ethyl acetate and washed successively with water, dilute hydrochloric acid and water. A saturated sodium bicarbonate solution was added to the ethereal layer to precipitate crystals. The crystals were removed by filtration, and the filtrate was washed with water and dried over anhydrous sodium sulfate. The solvent was removed by distillation to give (2S,4R)-1-(p-nitrobenzyloxycarbonyl)-2-hydroxymethyl-4-benzoyloxypyrrolidine.

IR $_{max}^{CHCl_3}$ cm$^{-1}$: 1720, 1530, 1435, 1352, 1280, 1115.

REFERENCE EXAMPLE 6

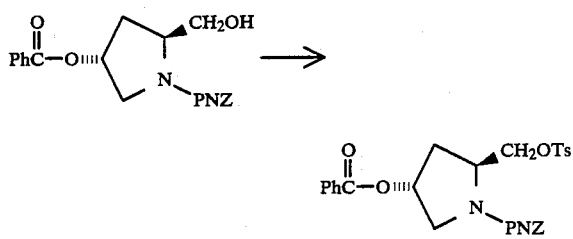

(2S,4R)-1-(p-Nitrobenzyloxycarbonyl)-2-hydroxymethyl-4-benzoyloxypyrrolidine (32.6 g) was dissolved in 64 ml of dry pyridine, and 28.02 g of p-toluenesulfonyl chloride was added thereto, followed by stirring at room temperature for 12 hours. The reaction mixture was diluted with water and extracted with a mixture of diethyl ether and dichloromethane (4:1). The extract was washed successively with brine, dilute hydrochloric acid, brine, a saturated sodium bicarbonate solution and brine, dried over anhydrous sodium sulfate and distilled to remove the solvent. Recrystallization of the residue from diethyl ether gave (2S,4R)-1-(p-nitrobenzyloxycarbonyl)-2-p-toluenesulfonyloxymethyl-4-benzoyloxypyrrolidine.

IR $_{max}^{CHCl_3}$ cm$^{-1}$: 1700, 1518, 1342, 1265, 1172, 1090.

REFERENCE EXAMPLE 7

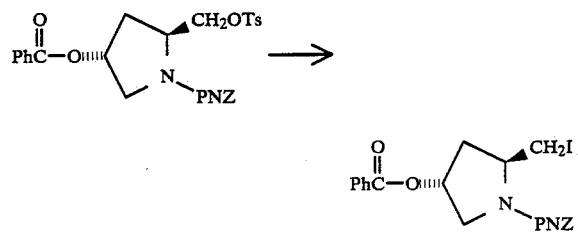

(2S,4R)-1-(p-Nitrobenzyloxycarbonyl)-2-p-toluenesulfonyloxymethyl-4-benzoyloxypyrrolidine (35.82 g) was dissolved in 90 ml of methylethylketone, and 19.29 g of sodium iodide was added thereto, followed by stirring under reflux for 1 hour. The reaction mixture was cooled down to room temperature and filtered. The filtrate was distilled to remove the solvent. The residue was diluted with ethyl acetate, washed successively with water, a sodium hypochlorite solution and water and dried over anhydrous sodium sulfate. The solvent was removed by distillation to give (2S,4R)-1-(p-nitrobenzyloxycarbonyl)-2-iodomethyl-4-benzoyloxypyrrolidine.

IR $_{max}^{Nujol}$ cm$^{-1}$: 1710, 1515, 1394, 1275, 1115.

REFERENCE EXAMPLE 8

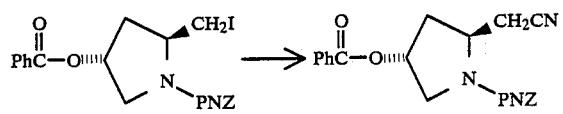

(2S,4R)-1-(p-Nitrobenzyloxycarbonyl)-2-iodomethyl-4-benzoyloxypyrrolidine (5.24 g) was dissolved in 26 ml of dry dimethylformamide, and 539 mg of sodium cyanide was added thereto, followed by stirring at room temperature for 24 hours. The reaction mixture was diluted with water and extracted with ethyl acetate. The extract was washed with water, dried over anhydrous sodium sulfate and distilled to remove the solvent. The residue was purified by silica gel column chromatography to give (2R,4R)-1-(p-nitrobenzyloxycarbonyl)-2-cyanomethyl-4-benzoyloxypyrrolidine.

IR $_{max}^{neat}$ cm$^{-1}$: 2250, 1715, 1605, 1520, 1400, 1345, 1275, 1110.

REFERENCE EXAMPLE 9

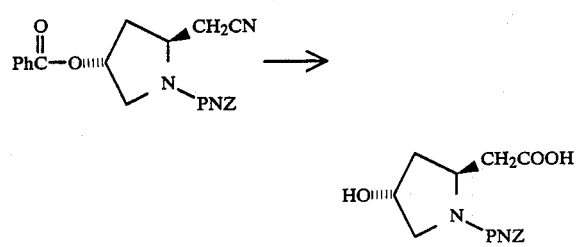

(2R,4R)-1-(p-Nitrobenzyloxycarbonyl)-2-cyanomethyl-4-benzoyloxypyrrolidine (3.0 g) was dissolved in 10 ml of acetic acid and 10 ml of conc. hydrochloric acid. After refluxing for 3 hours, the reaction mixture was cooled down to room temperature and distilled to remove the solvent. The residue was diluted with 4 ml of water and 25 ml of 1N sodium hydroxide solution. A solution of 1.53 g of p-nitrobenzyl chloroformate in 6 ml of diethyl ether and 2 ml of tetrahydrofuran was added to the above mixture at 0° C., followed by stirring at the same temperature for 30 minutes. The reaction mixture was separated. The aqueous layer was acidified with 6N hydrochloric acid to pH 1.0 and extracted with ethyl acetate. The extract was washed with water and dried over anhydrous sodium sulfate. The solvent was removed by distillation to give (2S,4R)-1-(p-nitrobenzyloxycarbonyl)-2-carboxymethyl-4-hydroxypyrrolidine.

IR $_{max}^{Nujol}$ cm$^{-1}$: 1690, 1603, 1517, 1460, 1200, 1116.

REFERENCE EXAMPLE 10

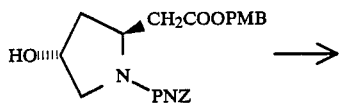

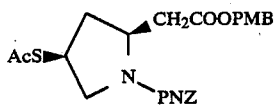

(2S,4R)-1-(p-Nitrobenzyloxycarbonyl)-2-p-methoxybenzyloxycarbonylmethyl-4-hydroxypyrrolidine (1.40 g) and triphenylphosphine (1.18 g) were dissolved in 7 ml of dry tetrahydrofuran under nitrogen stream. To the resulting solution was added 783 mg of diethyl azodicarboxylate at 0° C., followed by stirring at the same temperature for 30 minutes. Thereafter, 342 mg of thioacetic acid was added thereto, and the mixture was stirred for 1 hour. The reaction mixture was diluted with ethyl acetate, washed successively with a saturated sodium bicarbonate solution and water, dried over anhydrous sodium sulfate and distilled to remove the solvent. The residue was purified by silica gel column chromatography to give (2R,4S)-1-(p-nitrobenzyloxycarbonyl)-2-p-methoxybenzyloxycarbonylmethyl-4-acetylthiopyrrolidine.

IR $_{max}^{neat}$ cm$^{-1}$: 1700, 1605, 1510, 1400, 1343, 1240.

In the same procedure as above but using the corresponding alcohol, the thioacetate derivatives as shown in Table 3 were obtained.

TABLE 3

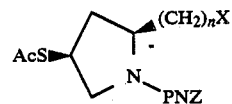

| No. | X | n | Physical data |
|---|---|---|---|
| 1 | NHCONH$_2$ | 1 | IR$_{max}^{neat}$ cm$^{-1}$: 1703 (sh), 1685, 1520, 1400, 1340, 1110 |
| 2 | NHCONMe$_2$ | 1 | IR$_{max}^{neat}$ cm$^{-1}$: 1685, 1635, 1520, 1400, 1342, 1115 |
| 3 | NHCOOEt | 1 | IR$_{max}^{CHCl_3}$ cm$^{-1}$: 3430, 1710, 1505, 1340, 1230, 1055 |
| 4 | NHAc | 1 | IR$_{max}^{neat}$ cm$^{-1}$: 1690, 1510, 1395, 1340, 1110, 845 |
| 5 | OTBDMS | 1 | IR$_{max}^{neat}$ cm$^{-1}$: 1710, 1525, 1400, 1345, 1253, 1115 |
| 6 | COOPMB | 2 | IR$_{max}^{neat}$ cm$^{-1}$: 1730, 1700, 1606, 1516, 1398, 1344, 1242 |
| 7 | SMe | 1 | IR$_{max}^{neat}$ cm$^{-1}$: 1710, 1612, 1528, 1403, 1350, 1108 |
| 8 | SO$_2$Me | 1 | IR$_{max}^{Nujol}$ cm$^{-1}$: 1701, 1522, 1453, 1343, 1300, 1125 |
| 9 | COOPMB | 3 | IR$_{max}^{neat}$ cm$^{-1}$: 1732, 1708, 1518, 1345, 1243 |
| 10 | COOtBu | 4 | IR$_{max}^{neat}$ cm$^{-1}$: 1720 (sh), 1700, 1520, 1400, 1342 |
| 11 | COOPNB | 1 | IR$_{max}^{neat}$ cm$^{-1}$: 1740, 1700, 1525, 1403, 1343 |
| 12 | CH=NNMe$_2$ | 1 | IR$_{max}^{neat}$ cm$^{-1}$: 1700, 1518, 1398, 1340 |
| 13 | CH=N—OMe | 1 | IR$_{max}^{neat}$ cm$^{-1}$: 1700, 1518, 1393, 1340 |

TABLE 3-continued

| No. | X | n | Physical data |
|---|---|---|---|
| 14 | CN | 1 | IR$_{max}^{neat}$ cm$^{-1}$: 2245, 1690, 1512, 1340 |
| 15 | OAc | 2 | IR$_{max}^{neat}$ cm$^{-1}$: 1740, 1705, 1520, 1400, 1345 |
| 16 | OAc | 3 | IR$_{max}^{neat}$ cm$^{-1}$: 1740, 1710, 1523, 1402, 1348 |
| 17 | CH$_2$NHPNZ (structure with PMZ) | | IR$_{max}^{neat}$ cm$^{-1}$: 1725 (sh), 1686, 1515, 1407, 1342, 1242 |

REFERENCE EXAMPLE 11

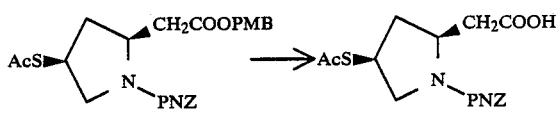

(2R,4S)-1-(p-Nitrobenzyloxycarbonyl)-2-p-methoxybenzyloxycarbonylmethyl -acetylthiopyrrolidine (810 mg) and anisole (330 mg) were stirred together with 4 ml of trifluoroacetic acid at room temperature for 30 minutes. The reaction mixture was concentrated under reduced pressure, and the residue was purified by silica gel thin layer chromatography to obtain (2R,4S)-1-(p-nitrobenzyloxycarbonyl)-2-carboxymethyl-4-acetylthiopyrrolidine.

IR $_{max}^{neat}$ cm$^{-1}$: 1690, 1602, 1517, 1400, 1342, 1108.

REFERENCE EXAMPLE 12

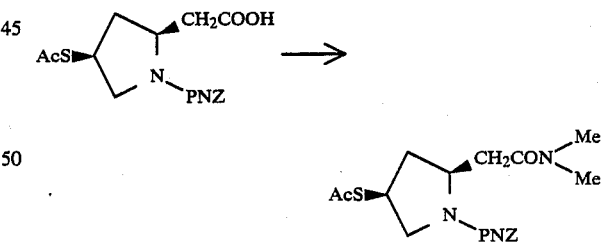

(2R,4S)-1-(p-Nitrobenzyloxycarbonyl)-2-carboxymethyl-4-acetylthiopyrrolidine (125 mg) was dissolved in 1 ml of dry methylene chloride, and 0.1 ml of oxalyl chloride and a catalytic amount of dimethylformamide were added thereto, followed by stirring at room temperature for 2 hours. The reaction mixture was distilled to remove the solvent, and dry benzene was added to the residue, followed by distillation of benzene. After two times repetition of the above procedure, the resulting residue was dissolved in 2 ml of dry methylene chloride. The resultant mixture was added to a solution of 45 mg of dimethylamine in 1.5 ml of dry methylene chloride and 0.2 ml of dry tetrahydrofuran under nitrogen stream at 0° C., followed by stirring at the same temperature for 30 minutes. The reaction mixture was diluted with methylene chloride, washed successively with water, dilute hydrochloric acid, water, a saturated sodium bicarbonate solution and water, dried over anhydrous sodium sulfate and distilled to remove the solvent. The residue was purified by silica gel thin layer chromatography to obtain (2R,4S)-1-(p-nitrobenzyloxycarbonyl)-2-dimethylaminocarbonylmethyl-4-acetylthiopyrrolidine.

IR $_{max}^{neat}$ cm$^{-1}$: 1700, 1635, 1518, 1398, 1342, 1100.

In the same procedure as above but using the corresponding acid, there was prepared (2R,4S)-1-(p-nitrobenzyloxycarbonyl)-2-(2-dimethylaminocarbonylethyl)-4-acetylthiopyrrolidine of the formula:

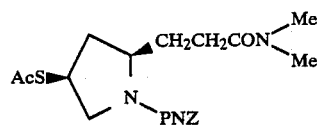

IR $_{max}^{neat}$ cm$^{-1}$: 1690, 1630, 1515, 1400, 1346, 1110.

REFERENCE EXAMPLE 13

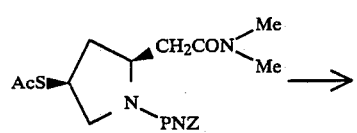

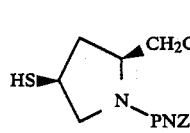

(2R,4S)-1-(p-Nitrobenzyloxycarbonyl)-2-dimethylaminocarbonylmethyl-4-acetylthiopyrrolidine (100 mg) was dissolved in 3 ml of methanol, and 0.24 ml of 1N sodium hydroxide solution was added thereto under nitrogen stream at room temperature, followed by stirring at the same temperature for 15 minutes. 1N Hydrochloric acid (0.24 ml) was added thereto, followed by concentration under reduced pressure. The concentrate was diluted with methylene chloride, washed with water, dried over anhydrous sodium sulfate and distilled to remove the solvent to obtain (2R,4S)-1-(p-nitrobenzyloxycarbonyl)-2-dimethylaminocarbonylmethyl-4-mercaptopyrrolidine.

IR $_{max}^{neat}$ cm$^{-1}$: 1700, 1640, 1520, 1400, 1345, 1100.

In the same procedure as above but using the corresponding thioacetate, the mercaptan derivatives as shown in Table 4 were obtained.

TABLE 4

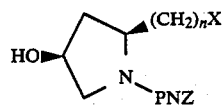

| No. | X | n | Physical data |
|---|---|---|---|
| 1 | CONH$_2$ | 1 | IR$_{max}^{CHCl_3}$ cm$^{-1}$: 1785, 1605, 1520, 1400, 1343, 1110 |
| 2 | COOMe | 1 | IR$_{max}^{neat}$ cm$^{-1}$: 1750, 1695, 1510, 1400, 1342, 1200, 1100 |
| 3 | NHCONH$_2$ | 1 | IR$_{max}^{neat}$ cm$^{-1}$: 1683, 1600, 1515, 1338, 1210, 1100 |
| 4 | NHCONMe$_2$ | 1 | IR$_{max}^{neat}$ cm$^{-1}$: 1690, 1630, 1520, 1398, 1340, 1110 |
| 5 | NHCOOEt | 1 | IR$_{max}^{CHCl_3}$ cm$^{-1}$: 3430, 1710, 1510, 1400, 1340, 1210, 1055 |
| 6 | NHA$_c$ | 1 | IR$_{max}^{CHCl_3}$ cm$^{-1}$: 2440, 1680, 1515, 1395, 1340, 1185, 1105, 840 |
| 7 | OCONMe$_2$ | 1 | IR$_{max}^{neat}$ cm$^{-1}$: 1703, 1518, 1400, 1343, 1188, 1102 |
| 8 | COOPNB | 1 | IR$_{max}^{neat}$ cm$^{-1}$: 1740, 1700, 1510, 1403, 1345 |
| 9 | OCONHMe | 1 | IR$_{max}^{neat}$ cm$^{-1}$: 1708, 1520, 1400, 1342, 1255, 1103 |
| 10 | OAc | 1 | IR$_{max}^{neat}$ cm$^{-1}$: 1739, 1708, 1510, 1400 |
| 11 | OCOOEt | 1 | IR$_{max}^{neat}$ cm$^{-1}$: 1743, 1710, 1523, 1400, 1345, 1260 |
| 12 | CONH$_2$ | 2 | IR$_{max}^{neat}$ cm$^{-1}$: 1680, 1600, 1510, 1395, 1340, 1200 |
| 13 | CONHMe | 2 | IR$_{max}^{Nujol}$ cm$^{-1}$: 1692, 1630, 1520, 1400, 1345 |
| 14 | CONMe$_2$ | 2 | IR$_{max}^{neat}$ cm$^{-1}$: 1705, 1640, 1523, 1403, 1350, 1110 |
| 15 | SMe | 1 | IR$_{max}^{neat}$ cm$^{-1}$: 1705, 1605, 1522, 1404, 1348, 1103 |
| 16 | SO$_2$Me | 1 | IR$_{max}^{neat}$ cm$^{-1}$: 1700, 1604, 1526, 1398, 1340, 1299 |
| 17 | OH | 1 | IR$_{max}^{CHCl_3}$ cm$^{-1}$: 1685, 1608, 1520, 1403, 1303, 1105 |
| 18 | OMe | 1 | IR$_{max}^{neat}$ cm$^{-1}$: 1710, 1522, 1430, 1345, 1103 |
| 19 | CONHMe | 3 | IR$_{max}^{neat}$ cm$^{-1}$: 1702, 1650, 1520, 1405, 1348 |
| 20 | CONHMe | 4 | IR$_{max}^{neat}$ cm$^{-1}$: 1698, 1650, 1518, 1400, 1340 |
| 21 | COOPNB | 2 | IR$_{max}^{neat}$ cm$^{-1}$: 1730, 1700, 1508, 1400, 1340 |
| 22 | CONHNMe$_2$ | 1 | IR$_{max}^{neat}$ cm$^{-1}$: 1700, 1522, 1400, 1348 |
| 23 | CH=N—OMe | 1 | IR$_{max}^{neat}$ cm$^{-1}$: 1700, 1520, 1400, 1343 |
| 24 | CN | 1 | IR$_{max}^{neat}$ cm$^{-1}$: 2240, 1690, 1512, 1333 |
| 25 | CH=NNMe$_2$ | 1 | IR$_{max}^{neat}$ cm$^{-1}$: 1710, 1522, 1402, 1348 |

TABLE 4-continued

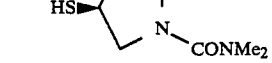

| No. | X | n | Physical data |
|---|---|---|---|
| 26 | 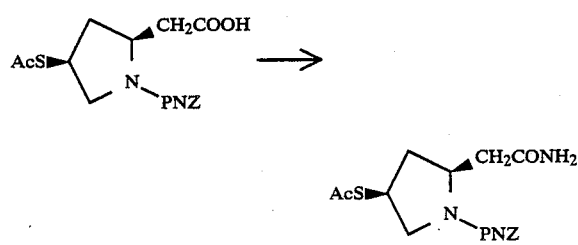 | | IR$_{max}^{CHCl_3}$ cm$^{-1}$: 1695, 1585, 1470, 1362, 1320 |

REFERENCE EXAMPLE 14

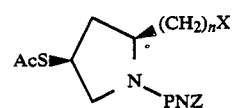

→

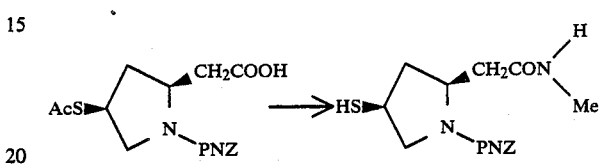

(2R,4S)-1-(p-Nitrobenzyloxycarbonyl)-2-carboxymethyl-4-acetylthiopyrrolidine (82 mg) was dissolved in 1.5 ml of dry tetrahydrofuran, and 33 mg of triethylamine was added thereto. Ethyl chloroformate (35 mg) was added to the mixture under nitrogen stream at $-10°$ to $-15°$ C., followed by stirring at the same temperature for 30 minutes. 29% (w/w) Aqueous ammonia (13 mg) was added at $-40°$ C. to the resulting mixture, followed by stirring at $-30°$ to $-40°$ C. for 30 minutes. The reaction mixture was acidified with dilute hydrochloric acid, diluted with ethyl acetate, washed successively with water, a saturated sodium bicarbonate solution and water, dried over anhydrous sodium sulfate and distilled to remove the solvent. The residue was purified by silica gel thin layer chromatography to obtain (2R,4S)-1-(p-nitrobenzyloxycarbonyl)-2-aminocarbonylmethyl-4-acetylthiopyrrolidine.

IR $_{max}^{CHCl_3}$ cm$^{-1}$: 1705, 1603, 1518, 1395, 1342, 1260, 1105.

In the same procedure as above but using the corresponding acid, the amide derivatives as shown in Table 5 were obtained.

TABLE 5

| No. | X | n | Physical data |
|---|---|---|---|
| 1 | CONH$_2$ | 2 | IR$_{max}^{CHCl_3}$ cm$^{-1}$: 1683, 1602, 1518, 1398, 1340, 1110 |
| 2 | CONHMe | 2 | IR$_{max}^{neat}$ cm$^{-1}$: 1692, 1633, 1520, 1394, 1340, 1195 |
| 3 | CONHMe | 3 | IR$_{max}^{neat}$ cm$^{-1}$: 1695, 1645, 1518, 1400, 1340 |
| 4 | CONHMe | 4 | IR$_{max}^{neat}$ cm$^{-1}$: 1690, 1650, 1519, 1400, 1342 |

REFERENCE EXAMPLE 15(1)

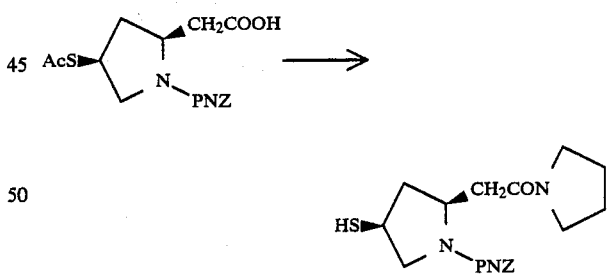

(2R,4S)-1-(p-Nitrobenzyloxycarbonyl)-2-carboxymethyl-4-acetylthiopyrrolidine (153 mg) was dissolved in 2 ml of dry tetrahydrofuran, and 61 mg of triethylamine was added thereto. Ethyl chloroformate (65 mg) was added thereto at $-10°$ to $-15°$ C. under nitrogen stream, followed by stirring at the same temperature for 30 minutes. A 30% ethanol solution of methylamine (414 mg) was added thereto at $-40°$ C., and stirring was continued at $-20°$ to $-30°$ C. for 1 hour. The reaction mixture was acidified with dilute hydrochloric acid, diluted with ethyl acetate, washed successively with water, a saturated sodium bicarbonate solution and water, dried over anhydrous sodium sulfate and distilled to remove the solvent. The residue was purified by silica gel thin layer chromatography to obtain (2R,4S)-1-(p-nitrobenzyloxycarbonyl)-2-methylaminocarbonylmethyl-4-mercaptopyrrolidine.

IR $_{max}^{neat}$ cm$^{-1}$: 1700, 1642, 1515, 1458, 1350.

REFERENCE EXAMPLE 15(2)

Following the procedure as in Reference Example 15(1) but replacing methylamine by pyrrolidine, (2R,4S)-1-(p-nitrobenzyloxycarbonyl)-2-pyrrolidinocarbonylmethyl-4-mercaptopyrrolidine was obtained.

IR $_{max}^{neat}$ cm$^{-1}$: 1700, 1615, 1520, 1430, 1356, 1107.

REFERENCE EXAMPLE 16

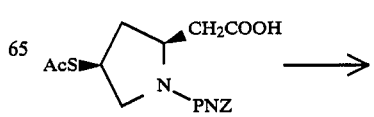

→

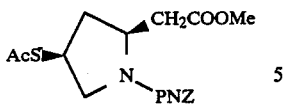

(2R,4S)-1-(p-Nitrobenzyloxycarbonyl)-2-carboxymethyl-4-acetylthiopyrrolidine (148 mg) was dissolved in 2 ml of dry methylene chloride, and 0.2 ml of oxalyl chloride and a catalytic amount of dimethylformamide were added thereto, followed by stirring at room temperature for 2 hours. The reaction mixture was distilled to remove the solvent, and dry benzene was added thereto, followed by distillation of benzene. After two times repetition of the above procedure, the residue was dissolved in 2 ml of dry methylene chloride. The solution was added to a mixture of methanol (125 mg), triethylamine (81 mg) and dry methylene chloride (1 ml) under nitrogen stream with ice-cooling and stirred at the same temperature for 2 hours. The reaction mixture was washed successively with water and dilute hydrochloric acid, dried over anhydrous sodium sulfate and distilled to remove the solvent to obtain (2R,4S)-1-(p-nitrobenzyloxycarbonyl)-2-methoxycarbonylmethyl-4-acetylthiopyrrolidine.

IR $_{max}^{neat}$ cm$^{-1}$: 1736, 1710, 1522, 1406, 1352, 1160.

REFERENCE EXAMPLE 17

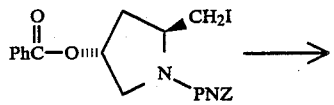

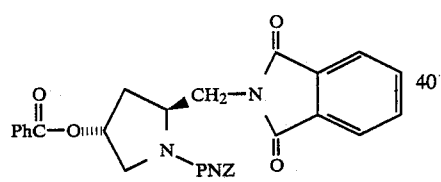

(2S,4R)-1-(p-Nitrobenzyloxycarbonyl)-2-iodomethyl-4-benzoyloxypyrrolidine (5.24 g) was dissolved in 21 ml of dry dimethylformamide, and 2.22 g of potassium phthalimide was added thereto, followed by stirring at 90° C. for 6 hours. The reaction mixture was diluted with water and extracted with ethyl acetate. The extract was washed with water, dried over anhydrous sodium sulfate and distilled to remove the solvent. The residue was purified by silica gel column chromatography to obtain (2S,4R)-1-(p-nitrobenzyloxycarbonyl)-2-phthalimidoylmethyl-4-benzoyloxypyrrolidine.

IR $_{max}^{neat}$ cm$^{-1}$: 1775, 1720, 1605, 1522, 1346, 1275.

REFERENCE EXAMPLE 18

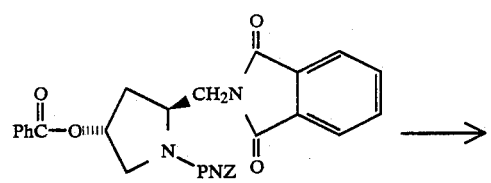

(2S,4R)-1-(p-Nitrobenzyloxycarbonyl)-2-phthalimidoylmethyl-4-benzoyloxypyrrolidine (490 mg) was dissolved in 20 ml of ethanol, and 432 mg of hydrazine hydrate was added thereto, followed by stirring under reflux for 30 minutes. The reaction mixture was cooled down to room temperature and filtered, and the filtrate was distilled to remove the solvent. The residue was dissolved in 3 ml of dry tetrahydrofuran, and 212 mg of trichloroacetyl isocyanate was added thereto, followed by stirring at room temperature for 3 hours. The resulting mixture was distilled off to remove the solvent. The residue was purified by silica gel thin layer chromatography to obtain (2S,4R)-1-(p-nitrobenzyloxycarbonyl)-2-trichloroacetylaminocarbonylaminomethyl-4-benzoyloxypyrrolidine.

IR $_{max}^{neat}$ cm$^{-1}$: 1710, 1600, 1517, 1440, 1270, 1110.

REFERENCE EXAMPLE 19

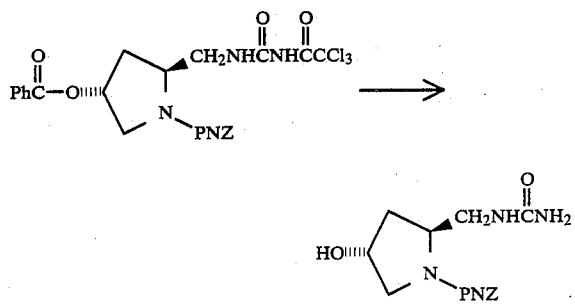

(2S,4R)-1-(p-Nitrobenzyloxycarbonyl)-2-trichloroacetylaminocarbonylaminomethyl-4-benzoyloxypyrrolidine (431 mg) was dissolved in 10 ml of methanol, and 1.48 ml of 1N sodium hydroxide solution was added thereto, followed by stirring at room temperature for 1.5 hours. 1N Hydrochloric acid (1.48 ml) was added thereto, followed by concentration to remove methanol. The residue was diluted with methylene chloride, washed with water, dried over anhydrous sodium sulfate and distilled to remove the solvent. The residue was purified by silica gel thin layer chromatography to obtain (2S,4R)-1-(p-nitrobenzyloxycarbonyl)-2-aminocarbonylaminomethyl-4-hydroxypyrrolidine.

IR $_{max}^{neat}$ cm$^{-1}$: 1665, 1596, 1510, 1425, 1336, 1103.

REFERENCE EXAMPLE 20(1)

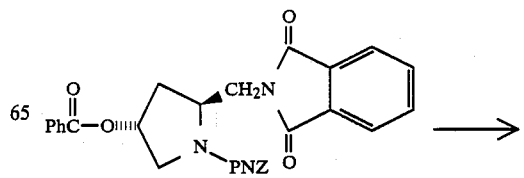

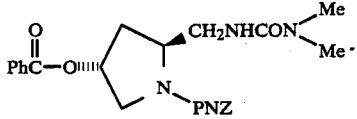

(2S,4R)-1-(p-Nitrobenzyloxycarbonyl)-2-phthalimidoylmethyl-4-benzoyloxypyrrolidine (105 mg) and hydrazine hydrate (14 mg) were dissolved in 2 ml of ethanol. The resulting mixture was refluxed for 30 minutes. After removal of any insoluble material by filtration, the filtrate was distilled to remove the solvent. The residue was dissolved in 2 ml of tetrahydrofuran, and 115 mg of triethylamine and 107 mg of dimethylaminocarbonyl chloride were added thereto. The resulting mixture was stirred at room temperature for 1 hour, diluted with ethyl acetate, washed successively with water, dilute hydrochloric acid, water, a saturated sodium bicarbonate solution and water, dried over anhydrous sodium sulfate and distilled to remove the solvent. The residue was purified by silica gel chromatography to obtain (2S,4R)-1-(p-nitrobenzyloxycarbonyl)-2-dimethylaminocarbonylaminomethyl-4-benzoyloxypyrrolidine.

IR $_{max}^{neat}$ cm$^{-1}$: 1710, 1640, 1530, 1345, 1275, 1110.

REFERENCE EXAMPLE 20(2)

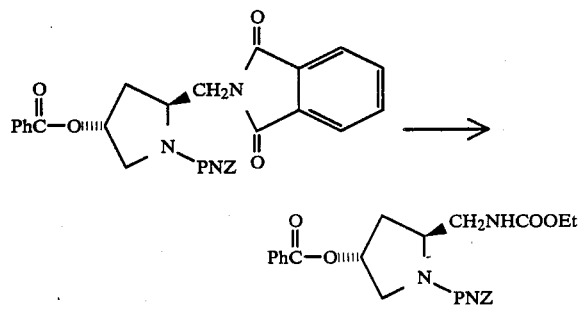

Following the procedure as in Reference Example 20(1) but replacing dimethylaminocarbonyl chloride by ethyl chloroformate, (2S,4R)-1-(p-nitrobenzyloxycarbonyl)-2-ethoxycarbonylaminoethyl-4-benzoyloxypyrrolidine was obtained.

IR $_{max}^{neat}$ cm$^{-1}$: 1705, 1515, 1400, 1345, 1270, 1100.

REFERENCE EXAMPLE 20(3)

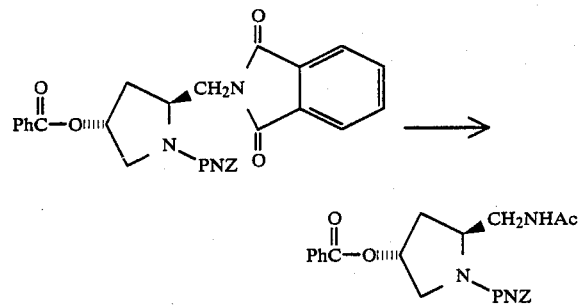

Following the procedure as in Reference Example 20(1) but replacing dimethylaminocarbonyl chloride by acetyl chloride, (2S,4R)-1-(p-nitrobenzyloxycarbonyl)-2-acetylaminomethyl-4-benzoyloxypyrrolidine was obtained.

IR $_{max}^{neat}$ cm$^{-1}$: 1705, 1520, 1400, 1345, 1275, 1110.

REFERENCE EXAMPLE 21

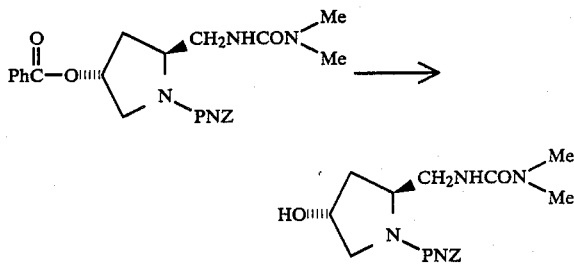

(2S,4R)-1-(p-Nitrobenzyloxycarbonyl)-2-dimethylaminocarbonylaminomethyl-4-benzoyloxyprrolidine (145 mg) was dissolved in methanol (2.4 ml), and 0.32 ml of 1N sodium hydroxide solution was added thereto. The resulting mixture was stirred at room temperature for 30 minutes. To the reaction mixture was added 0.32 ml of 1N hydrochloric acid, and the mixture was distilled to remove methanol. The residue was diluted with methylene chloride, washed with water, dried over anhydrous sodium sulfate and distilled to remove the solvent. The residue was purified by silica gel chromatography to obtain (2S,4R)-1-(p-nitrobenzyloxycarbonyl)-2-dimethylaminocarbonylaminomethyl-4-hydroxypyrrolidine.

IR $_{max}^{neat}$ cm$^{-1}$: 1690, 1632, 1530, 1410, 1345, 1110.

In the same procedure as above but using the corresponding benzoate, the following alcohol derivatives as shown in Table 6 were obtained.

TABLE 6

| No. | X | n | Physical data |
|---|---|---|---|
| 1 | NHCOOEt | 1 | IR$_{max}^{neat}$ cm$^{-1}$: 1690, 1530, 1410, 1350, 1260 |
| 2 | NHAc | 1 | IR$_{max}^{neat}$ cm$^{-1}$: 1685, 1520, 1425, 1345, 1185, 1110 |
| 3 | OTBDMS | 1 | IR$_{max}^{neat}$ cm$^{-1}$: 1700, 1525, 1430, 1343, 1108, 834 |
| 4 | I | 1 | IR$_{max}^{neat}$ cm$^{-1}$: 1690, 1610, 1520, 1435, 1404, 1350 |
| 5 | SMe | 1 | IR$_{max}^{neat}$ cm$^{-1}$: 1683, 1603, 1518, 1425, 1400, 1342 |
| 6 | SO$_2$Me | 1 | IR$_{max}^{neat}$ cm$^{-1}$: 1698, 1522, 1403, 1342, 1302, 1120 |
| 7 | CN | 1 | IR$_{max}^{neat}$ cm$^{-1}$: 2235, 1690, 1512, 1333 |

REFERENCE EXAMPLE 22

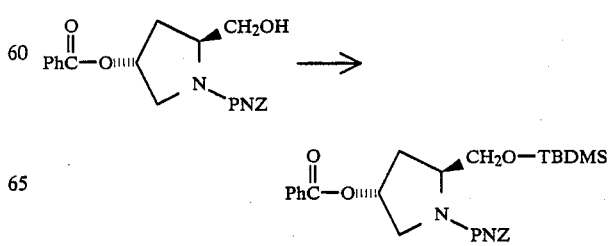

(2S,4R)-1-(p-Nitrobenzyloxycarbonyl)-2-hydroxymethyl-4-benzoyloxypyrrolidine (1.09 g), imidazole (0.46 g) and t-butyldimethylsilyl chloride (0.49 g) were dissolved in 16.5 ml of dry dimethylformamide. The resulting mixture was stirred at room temperature for 2 hours, diluted with ethyl acetate, washed with water, dried over anhydrous magnesium sulfate and distilled to remove the solvent. The residue was purified by silica gel chromatography to obtain (2S,4R)-1-(p-nitrobenzyloxycarbonyl)-2-t-butyldimethylsilyloxymethyl-4-benzoyloxypyrrolidine.

IR $max^{neat}$ cm$^{-1}$: 1710, 1520, 1400, 1340, 1265, 1108.

REFERENCE EXAMPLE 23

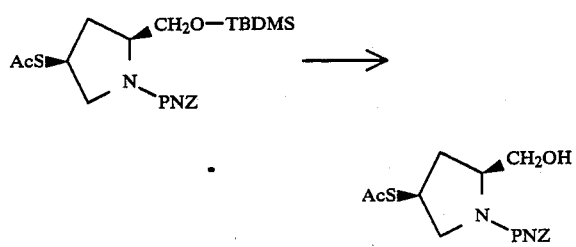

(2S,4S)-1-(p-Nitrobenzyloxycarbonyl)-2-t-butyldimethylsilyloxymethyl-4-acetylthiopyrrolidine (0.85 g) was dissolved in methanol (8.5 ml), and 0.85 ml of 6N hydrochloric acid was added thereto. The resulting mixture was stirred at room temperature for 2.5 hours, diluted with ethyl acetate, washed with water, dried over anhydrous magnesium sulfate and distilled to remove the solvent. Recrystallization of the residue from diethyl ether gave (2S,4S)-1-(p-nitrobenzyloxycarbonyl)-2-hydroxymethyl-4-acetylthiopyrrolidine.

IR $max^{Nujol}$ cm$^{-1}$: 1690, 1670, 1514, 1460, 1203.

REFERENCE EXAMPLE 24

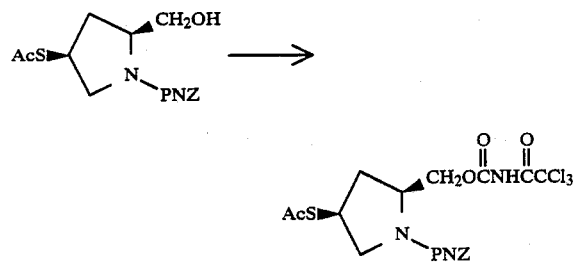

(2S,4S)-1-(p-Nitrobenzyloxycarbonyl)-2-hydroxymethyl-4-acetylthiopyrrolidine (100 mg) was dissolved in 3 ml of dry ethyl acetate. To the solution was added 0.05 ml of trichloroacetyl isocyanate under ice-cooling in a nitrogen stream, followed by stirring at the same temperature for 1 hour. The mixture was diluted with ethyl acetate, washed successively with a saturated sodium bicarbonate solution and water, dried over anhydrous sodium sulfate and distilled to obtain (2S,4S)-1-(p-nitrobenzyloxycarbonyl)-2-trichloroacetylaminocarbonyloxymethyl-4-acetylthiopyrrolidine.

IR $max^{neat}$ cm$^{-1}$: 1722, 1680, 1602, 1400, 1335, 1250, 1102.

REFERENCE EXAMPLE 25

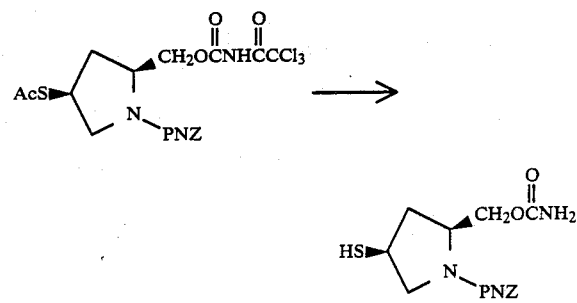

(2S,4S)-1-(p-Nitrobenzyloxycarbonyl)-2-trichloroacetylaminocarbonyloxymethyl-4-acetylthiopyrrolidine (121 mg) was dissolved in 5.8 ml of methanol. To the solution was added 0.45 ml of 1N sodium hydroxide solution under ice-cooling in a nitrogen stream, followed by stirring at the same temperature for 40 minutes. After neutralization by 1.45 ml of 1N hydrochloric acid, the mixture was distilled to remove methanol. The residue was diluted with methylene chloride, washed with water, dried over anhydrous sodium sulfate and distilled to obtain (2S,4S)-1-(p-nitrobenzyloxycarbonyl)-2-aminocarbonyloxymethyl-4-mercaptopyrrolidine.

IR $max^{neat}$ cm$^{-1}$: 1715, 1603, 1512, 1398, 1360, 1098.

REFERENCE EXAMPLE 26

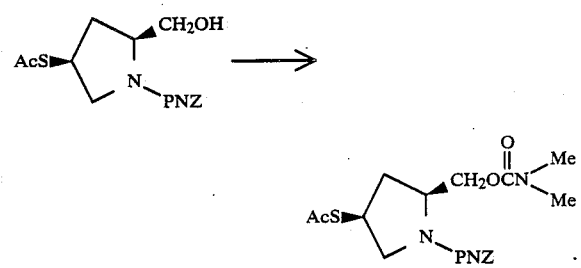

(2S,4S)-1-(p-Nitrobenzyloxycarbonyl)-2-hydroxymethyl-4-acetylthiopyrrolidine (78 mg) was dissolved in 1 ml of dry pyridine, and 135 mg of 4-N,N-dimethylaminopyridine and 119 mg of dimethylaminocarbonyl chloride were added successively thereto, followed by stirring at 90° to 100° C. for 20 hours. The reaction mixture was diluted with water and extracted with ethyl acetate. The extract was washed successively with water, dilute hydrochloric acid, water, a saturated sodium bicarbonate solution and water, dried over anhydrous sodium sulfate and distilled to obtain (2S,4S)-1-(p-nitrobenzyloxycarbonyl)-2-dimethylaminocarbonyloxymethyl-4-acetylthiopyrrolidine.

IR $max^{neat}$ cm$^{-1}$: 1700, 1515, 1393, 1340, 1185, 1100.
NMR δ (CDCl$_3$) 2.34 (3H,s), 2.89 (6H,s), 5.23 (2H,s).

REFERENCE EXAMPLE 27

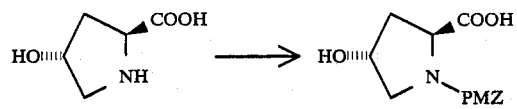

trans-4-Hydroxy-L-proline (13.1 g) and triethylamine (21 ml) were dissolved in 55 ml of water, and a solution of 33.44 g of S-p-methoxybenzyloxycarbonyl-4,6-dimethyl-2-mercaptopyrimidine in 55 ml of dimethylformamide was added thereto. The resulting mixture was stirred at room temperature for 12 hours, diluted with water and washed with ethyl acetate. The aqueous layer was acidified with 5N hydrochloric acid (pH 2) under ice-cooling and extracted with ethyl acetate. The extract was washed successively with dilute hydrochloric acid and brine, dried over anhydrous sodium sulfate and distilled to obtain trans-1-(p-methoxybenzyloxycarbonyl)-4-hydroxy-L-proline. IR $_{max}^{neat}$ cm$^{-1}$: 1670, 1435, 1350, 1240, 1168.

REFERENCE EXAMPLE 28

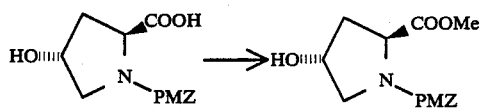

trans-1-(p-Methoxybenzyloxycarbonyl)-4-hydroxy-L-proline (5.0 g) was dissolved in 50 ml of methanol and 50 ml of tetrahydrofuran. An ethereal solution of diazomethane was added thereto under ice-cooling until nitrogen gas evolution stopped. The mixture was allowed to stand overnight and distilled to obtain trans-1-(p-methoxy-benzyloxycarbonyl)-4-hydroxy-L-proline methyl ester.

IR $_{max}^{neat}$ cm$^{-1}$: 1748, 1695, 1518, 1438, 1360, 1250, 1175.

REFERENCE EXAMPLE 29

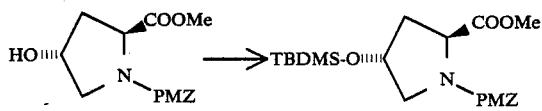

trans-1-(p-Methoxybenzyloxycarbonyl)-4-hydroxy-L-proline methyl ester (5.18 g), 3.79 g of triethylamine and 3.77 g of t-butyldimethylsilyl chloride were dissolved in 52 ml of dry dimethylformamide. The resulting mixture was stirred at room temperature for 3 hours, diluted with water, extracted with ethyl acetate, washed successively with water, dilute hydrochloric acid and water, dried over anhydrous sodium sulfate and distilled to remove the solvent. The residue was purified by silica gel chromatography to obtain trans-1-(p-methoxybenzyloxycarbonyl)-4-t-butyldimethylsilyloxy-L-proline methyl ester.

IR $_{max}^{neat}$ cm 1750, 1710, 1517, 1415, 1355, 1250, 1115.

In the same procedure as above but using the corresponding alcohols, the t-butyldimethylsilyl ether derivatives as shown in Table 7 were obtained.

TABLE 7

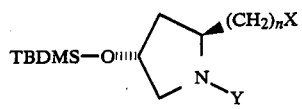

| No. | X | Y | n | Physical data |
|---|---|---|---|---|
| 1 | I | PNZ | 1 | IR$_{max}^{Nujol}$ cm$^{-1}$: 1690, 1505, 1345, 1130, 1100, 830 |

TABLE 7-continued

| No. | X | Y | n | Physical data |
|---|---|---|---|---|
| 2 | COOMe | Z | 0 | IR$_{max}^{neat}$ cm$^{-1}$: 1750, 1710, 1410, 1350, 1250 |
| 3 | COOMe | PNZ | 1 | IR$_{max}^{neat}$ cm$^{-1}$: 1740, 1713, 1523, 1400, 1345 |
| 4 | COOMe | PNZ | 2 | IR$_{max}^{neat}$ cm$^{-1}$: 1738, 1705, 1523, 1405, 1350 |

REFERENCE EXAMPLE 30

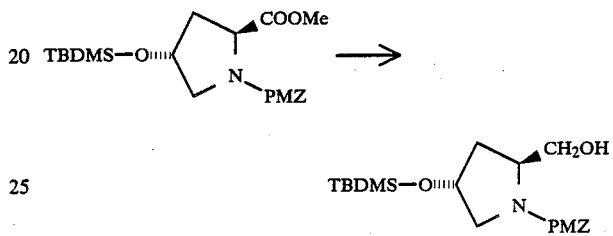

trans-1-(p-Methoxybenzyloxycarbonyl)-4-t-butyldimethylsilyloxy-L-proline methyl ester (5.64 g) was dissolved in 56.4 ml of dry tetrahydrofuran. Sodium borohydride (1.01 g) and lithium iodide (3.52 g) were added thereto. The resulting mixture was refluxed for 1 hour, diluted with water, extracted with ethyl acetate, washed with water, dried over anhydrous sodium sulfate and distilled off to obtain (2S,4R)-1-(p-methoxybenzyloxycarbonyl)-2-hydroxymethyl-4-t-butyldimethylsilyloxypyrrolidine.

IR $_{max}^{neat}$ cm$^{-1}$: 1670, 1504, 1420, 1405, 1240, 1100.

In the same procedure as above but using the corresponding methyl ester, the alcohol derivatives as shown in Table 8 were obtained.

TABLE 8

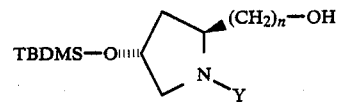

| No. | n | Y | Physical data |
|---|---|---|---|
| 1 | 1 | Z | IR$_{max}^{neat}$ cm$^{-1}$: 1700, 1415, 1355, 1250, 1110 |
| 2 | 3 | Z | IR$_{max}^{neat}$ cm$^{-1}$: 1702, 1410, 1358, 1258, 1118 |
| 3 | 2 | PNZ | IR$_{max}^{Nujol}$ cm$^{-1}$: 1678, 1522, 1463, 1402, 1345 |
| 4 | 3 | PNZ | IR$_{max}^{neat}$ cm$^{-1}$: 1690, 1525, 1405, 1350 |

REFERENCE EXAMPLE 31

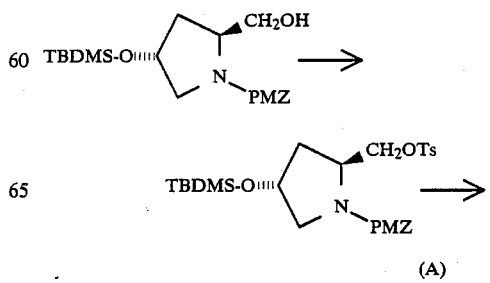

(A)

-continued

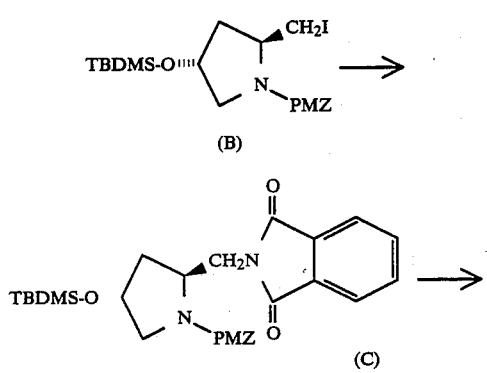

TABLE 9

| No. | X | n | Physical data | |
|---|---|---|---|---|
| 1 | COOtBu | 4 | $IR_{max}^{neat}$ cm$^{-1}$: | 1723 (sh), 1700, 1522, 1402, 1345 |
| 2 | CH=NNMe$_2$ | 1 | $IR_{max}^{neat}$ cm$^{-1}$: | 1700, 1520, 1400, 1343 |
| 3 | CH=N—OMe | 1 | $IR_{max}^{CHCl_3}$ cm$^{-1}$: | 1690, 1520, 1405, 1350 |
| 4 | OAc | 2 | $IR_{max}^{neat}$ cm$^{-1}$: | 1740, 1700, 1525, 1415, 1355 |
| 5 | OAc | 3 | $IR_{max}^{neat}$ cm$^{-1}$: | 1740, 1700, 1525, 1410, 1355 |

Following the procedure as in Reference Examples 6, 7, 17 and 20(1), (2S,4R)-1-(p-methoxybenzyloxycarbonyl)-4-(p-nitrogbenzyloxycarbonyl)aminomethyl-4-t-butyldimethylsilyloxypyrrolidine was obtained from the starting material, i.e., (2S,4R)-1-methoxybenzyloxycarbonyl)-2-hydroxymethyl-4-t-butyldimethylsilyloxypyrrolidine.

$IR_{max}^{neat}$ cm$^{-1}$: 1720, 1690(sh), 1517, 1345, 1245, 1112.

Compound A: $IR_{max}^{neat}$ cm$^{-1}$: 1700, 1505, 1402, 1354, 1240, 1166.

Compound B: $IR_{max}^{neat}$ cm$^{-1}$: 1700, 1512, 1405, 1353, 1248, 1100.

Compound C: $IR_{max}^{neat}$ cm$^{-1}$: 1757, 1715, 1510, 1390, 1245, 1111.

REFERENCE EXAMPLE 32

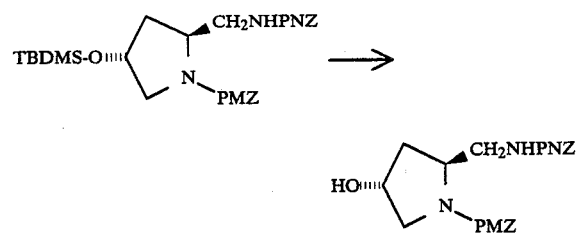

(2S,4R)-1-(p-Methoxybenzyloxycarbonyl)-2-(p-nitrobenzyloxycarbonyl)aminomethyl-4-t-butyldimethylsilyloxyprrolidine (850 mg) was dissolved in 8.5 ml of methanol and 1 ml of 6N hydrochloric acid was added thereto. The resulting mixture was stirred at room temperature for 30 minutes, diluted with ethyl acetate, washed with water, dried over anhydrous sodium sulfate and distilled to remove the solvent. The residue was purified by silica gel chromatography to obtain (2S,4R)-1-(p-methoxybenzyloxycarbonyl)-2-(p-nitrobenzyloxycarbonyl)aminomethyl-4-hydroxypyrrolidine.

$IR_{max}^{CHCl_3}$ cm$^{1-1}$: 1720 (sh), 1680, 1510, 1410, 1342, 1225.

In the same procedure as above but using the corresponding t-butyldimethylsilyl ether, the alcohol derivatives as shown in Table 9 were obtained.

REFERENCE EXAMPLE 33

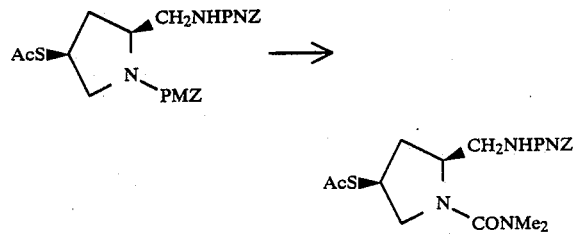

(2S,4S)-1-(p-Methoxybenzyloxycarbonyl)-2-(p-nitrobenzyloxycarbonyl)aminomethyl-4-acetylthiopyrrolidine (500 mg), 216 mg of anisole and 4 ml of trifluoroacetic acid were stirred at room temperature for 1 hour. The mixture was distilled to remove the solvent. The residue was dissolved in dichloromethane, washed successively with a saturated sodium bicarbonate solution and water, dried over anhydrous sodium sulfate and distilled to remove the solvent. The residue was dissolved in 4 ml of tetrahydrofuran, and 152 mg of triethylamine and 141 mg of dimethylaminocarbonyl chloride were added thereto. The resulting mixture was stirred at room temperature for 30 minutes, diluted with ethyl acetate, washed successively with water, carbonate solution and water, dried over anhydrous sodium sulfate and distilled to remove the solvent. The residue was purified by silica gel chromatography to obtain (2S,4S)-1-dimethylaminocarbonyl-2-(p-nitrobenzyloxycarbonyl)aminomethyl-4-acetylthiopyrrolidine.

$IR_{max}^{neat}$ cm$^{-1}$: 1720, 1695 (sh), 1620, 1510, 1446, 1240.

REFERENCE EXAMPLE 34(1)

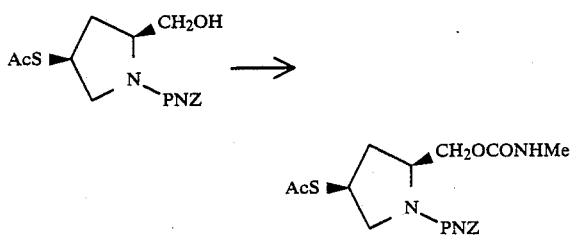

(2S,4S)-1-(p-Nitrobenzyloxycarbonyl)-2-hydroxymethyl-4-acetylthiopyrrolidine (200 mg) was dissolved in 2 ml of dry tetrahydrofuran. Methyl isocyanate (0.168 ml) was added thereto. The mixture was refluxed for 10 hours and distilled to remove the solvent. The residue was purified by silica gel chromatography to obtain (2S,4S)-1-(p-nitrobenzyloxycarbonyl)-2-methylaminocarbonyloxymethyl-4-acetylthiopyrrolidine.

IR$_{max}^{neat}$ cm$^{-1}$: 1702, 1521, 1402, 1350, 1258, 1110.

REFERENCE EXAMPLE 34(2)

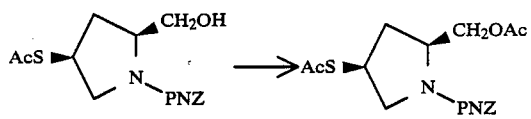

(2S,4S)-1-(p-Nitrobenzyloxycarbonyl)-2-hydroxymethyl-4-acetylthiopyrrolidine (300 mg) was dissolved in 1.5 ml of dry pyridine. Acetic anhydride (1.5 ml) was added thereto. The resulting mixture was stirred at room temperature for 5 hours, diluted with water, extracted with ether, washed successively with brine, dilute hydrochloric acid, brine, a saturated sodium bicarbonate solution and brine, dried over anhydrous sodium sulfate and distilled to obtain (2S,4S)-1-(p-nitrobenzyloxycarbonyl)-2-acetoxymethyl-4-acetylthiopyrrolidine.

IR$_{max}^{neat}$ cm$^{-1}$: 1735, 1690, 1512, 1390, 1340, 1225.

REFERENCE EXAMPLE 34(3)

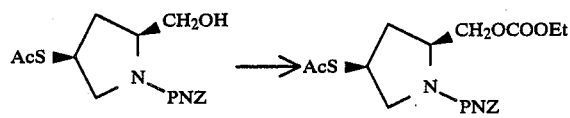

(2S,4S)-1-(p-Nitrobenzyloxycarbonyl)-2-hydroxymethyl-4-acetylthiopyrrolidine (177 mg), 76 mg of triethylamine and 61 mg of 4-N,N-dimethylaminopyridine were dissolved in 2 ml of dry dichloromethane. Ethyl chloroformate (81 mg) was added thereto under ice-cooling in a nitrogen stream. The mixture was stirred under ice-cooling for 3.5 hours, washed successively with water, dilute hydrochloric acid, water, a saturated sodium bicarbonate solution and water, dried over anhydrous sodium sulfate and distilled to obtain (2S,4S)-1-(p-nitrobenzyloxycarbonyl)-2-ethoxycarbonyloxymethyl-4-acetylthiopyrrolidine.

IR$_{max}^{neat}$ cm$^{-1}$: 1740, 1702, 1520, 1400, 1343, 1248

REFERENCE EXAMPLE 35

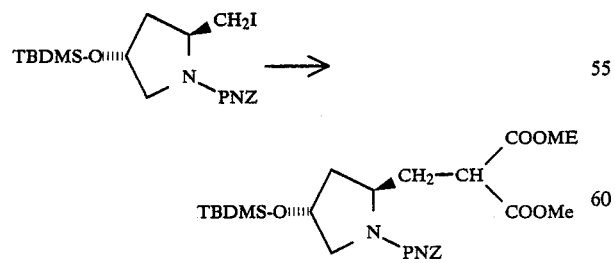

Dimethyl malonate (660 mg) and 180 mg of 50% sodium hydride in 12.5 ml of dry dimethylformamide were stirred at room temperature in a nitrogen stream for 15 minutes, and 1.34 g of (2S,4R)-1-(p-nitrobenzyloxycarbonyl)-2-iodomethyl-4-t-butyldimethylsilyloxypyrrolidine was added thereto. The resulting mixture was stirred at room temperature for 15 hours, neutralized with 3.75 ml of 1N hydrochloric acid, diluted with water, extracted with ethyl acetate, washed with water, dried over anhydrous sodium sulfate and distilled to remove the solvent. The residue was purified by silica gel chromatogrphy to obtain (2R,4R)-1-(p-nitrobenzyloxycarbonyl)-2-(2,2-dimethoxycarbonylethyl)-4-t-butyldimethylsilyloxypyrrolidine.

IR$_{max}^{neat}$ cm$^{-1}$: 1755, 1710, 1527, 1400, 1350, 1258.

The following compound was obtained in the same procedure as above.

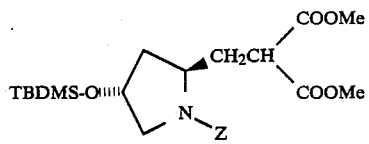

IR$_{max}^{neat}$ cm$^{-1}$: 1735, 1700, 1430, 1403, 1342.

REFERENCE EXAMPLE 36

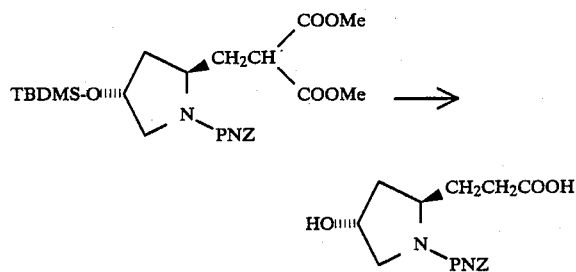

(2R,4R)-1-(p-Nitrobenzyloxycarbonyl)-2-(2,2-dimethoxycarbonylethyl)-4-t-butyldimethylsilyloxypyrrolidine (1.04 g) was dissolved in 6 ml of methanol, 3 ml of 4N sodium hydroxide solution was added thereto, and the resulting mixture was stirred at room temperature for 1.5 hours. The reaction mixture was acidified with 6 ml of 6N hydrochloric acid, and 5 ml of tetrahydrofuran was added thereto. The resulting mixture was stirred at room temperature for 2 days, diluted with water, adjusted to alkaline with a saturated sodium bicarbonate solution and extracted with ether. The aqueous layer was acidified (pH 1) with dilute hydrochloric acid, extracted with ethyl acetate, washed with water, dried over anhydrous sodium sulfate and distilled to obtain (2R,4R)-1-(p-nitrobenzyloxycarbonyl)-2-(2-carboxyethyl)-4-hydroxypyrrolidine.

IR$_{max}^{neat}$ cm$^{-1}$: 1710, 1610, 1524, 1435, 1410, 1352.

REFERENCE EXAMPLE 37

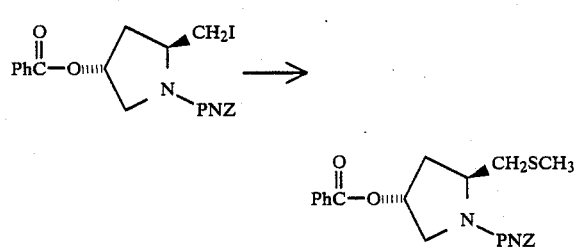

(2S,4R)-1-p-Nitrobenzyloxycarbonyl-2-iodomethyl-4-benzoyloxypyrrolidine (1.05 g) was dissolved in 10 ml of dimethylformamide, and a solution of 1.40 g of 15% methylmercaptan sodium salt in water was added thereto, followed by stirring at room temperature for 30 minutes under a nitrogen stream. The reaction mixture was diluted with ethyl acetate, washed with water, dried over anhydrous sodium sulfate and distilled to remove the solvent. The residue was purified by silica gel thin layer chromatography to obtain (2S,4R)-1-p-nitrobenzyloxycarbonyl-2-methylthiomethyl-4-benzoyloxypyrrolidine.

IR$_{max}^{neat}$ cm$^{-1}$: 1700, 1597, 1518, 1392, 1339, 1263.

REFERENCE EXAMPLE 38

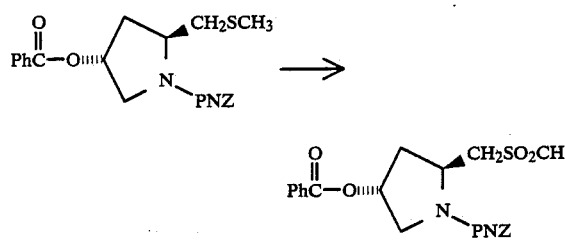

(2S,4R)-1-p-Nitrobenzyloxycarbonyl-2-methylthiomethyl-4-benzoyloxypyrrolidine (330 mg) was dissolved in 3.3 ml of dry chloroform, and 385 mg of m-chloroperbenzoic acid was added thereto, followed by refluxing for 6 hours. To the reaction mixture was added ether, and the resulting mixture was washed successively with a saturated sodium bicarbonate solution and brine, dried over anhydrous sodium sulfate and distilled to remove the solvent. The residue was purified by silica gel thin layer chromatography to obtain (2S,4R)-1-p-nitrobenzyloxycarbonyl-2-methylsulfonylmethyl-4-benzoyloxypyrrolidine.

IR$_{max}^{Nujol}$ cm$^{-1}$: 1719, 1692, 1518, 1450, 1345, 1299.

REFERENCE EXAMPLE 39

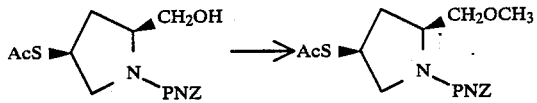

(2S,4S)-1-p-Nitrobenzyloxycarbonyl-2-hydroxymethyl-4-acetylthiopyrrolidine (354 mg) was dissolved in 30 ml of dichloromethane, and a solution of diazomethane in ether and a catalytic amount of BF$_3$—Et$_2$O complex were added thereto under ice-cooling, followed by stirring at the same temparature for 5 minutes. The reaction mixture was washed with brine, and after removal of any insoluble material by filtration from the dichloromethane layer, the filtrate was washed successively with a saturated sodium bicarbonate solution and brine, dried over anhydrous magnesium sulfate and distilled to remove the solvent. The residue was purified by silica gel thin layer chromatography to obtain (2S,4S)-1-p-nitrobenzyloxycarbonyl-2-methoxymethyl-4-acethylthiopyrrolidine.

IR$_{max}^{neat}$ cm$^{-1}$: 1700, 1685, 1516, 1392, 1340, 1100.

REFERENCE EXAMPLE 40

The mesylate derivatives as shown in Table 10 were obtained from the corresponding alcohols in the same procedure as in Reference Example 6 but replacing p-toluenesulfonyl chloride by methanesulfonyl chloride.

TABLE 10

| No. | n | Physical data |
|---|---|---|
| 1 | 1 | IR$_{max}^{neat}$ cm$^{-1}$: 1700, 1410, 1350, 1250, 1172 |
| 2 | 3 | IR$_{max}^{neat}$ cm$^{-1}$: 1698, 1410, 1352, 1250, 1175 |

REFERENCE EXAMPLE 41

The iodide derivatives as shown in Table 11 were obtained from the corresponding mesylates in the same procedure as in Reference Example 7.

TABLE 11

| No. | n | Physical data |
|---|---|---|
| 1 | 1 | IR$_{max}^{neat}$ cm$^{-1}$: 1700, 1403, 1353, 1250, 1103 |
| 2 | 3 | IR$_{max}^{neat}$ cm$^{-1}$: 1700, 1405, 1352, 1250, 1102 |

REFERENCE EXAMPLE 42

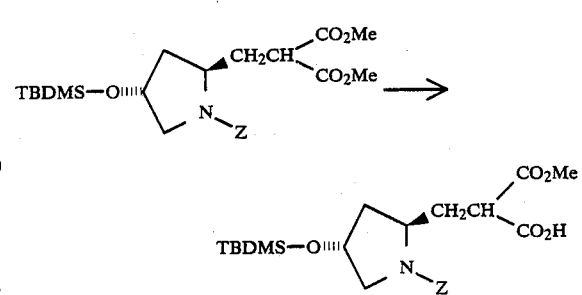

(2R,4R)-1-Benzyloxycarbonyl-2-(2,2-dimethoxycarbonyl)ethyl-4-t-butyldimethylsilyloxypyrrolidine (18 g) was dissolved in 180 ml of methanol, and 36 ml of 1N sodium hydroxide solution was added thereto, followed by stirring at room temperature for 18 hours. To the reaction mixture was added 36 ml of 1N hydrochloric acid, and the resulting mixture was distilled to remove the solvent. The residue was diluted with ethyl acetate, dried over anhydrous sodium sulfate and distilled to obtain (2R,4R)-1-benzyloxycarbonyl-2-(2-carboxy-2-methoxylcarbonyl)ethyl-4-t-butyldimethylsilyloxypyrrolidine.

IR$_{max}^{neat}$ cm$^{-1}$: 1732, 1710, 1680, 1420, 1350.

REFERENCE EXAMPLE 43

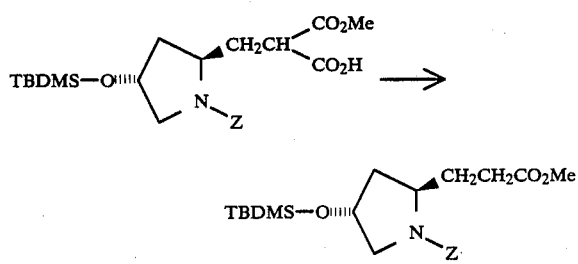

(2R,4R)-1-Benzyloxycarbonyl-2-(2-carboxy-2-methoxycarbonyl)ethyl-4-t-butyldimethylsilyloxypyrrolidine (18 g) was dissolved in 90 ml of dry dimethylsulfoxide, followed by stirring at 140° C. for 3 hours. The reaction mixture was poured into ice-water, extracted with ethyl acetate, dried over anhydrous sodium sulfate and distilled to obtain (2R,4R)-1-benzyloxycarbonyl-2-(2-methoxycarbonyl)ethyl-4-t-butyldimethylsilyloxypyrrolidine.

IR$_{max}^{neat}$ cm$^{-1}$: 1740, 1705, 1410, 1358, 1258.

REFERENCE EXAMPLE 44

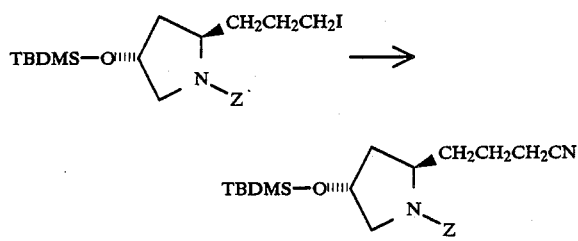

Following the procedure as in Reference Example 8 but using (2R,4R)-1-benzyloxycarbonyl-2-(3-iodopropyl)-4-t-butyldimethylsilyloxypyrrolidine as the starting material, (2R,4R)-1-benzyloxycarbonyl-2-(3-cyanopropyl)-4-t-butyldimethylsilyloxypyrrolidine was obtained.

IR$_{max}^{neat}$ cm$^{-1}$: 2250, 1705, 1415, 1358, 1255, 1112.

REFERENCE EXAMPLE 45

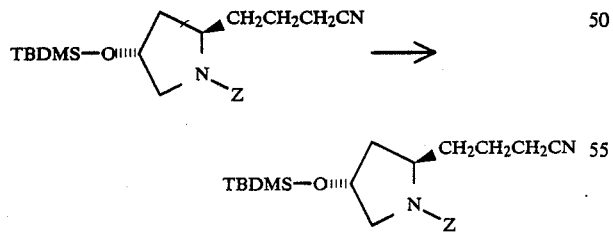

(2R,4R)-1-Benzyloxycarbonyl-2-(3-cyanopropyl)-4-t-butyldimethylsilyloxypyrrolidine (1.69 g) was dissolved in 34 ml of ethanol, and 338 mg of 5% palladium-carbon was added thereto, followed by hydrogenation at room temparature under 1 atm. for 2 hours. The catalyst was removed by filtration, and the filtrate was distilled to obtain (2R,4R)-2-(3-cyanopropyl)-4-t-butyldimethylsilyloxypyrrolidine.

IR$_{max}^{neat}$ cm$^{-1}$: 2245, 1460, 1250, 1080

REFERENCE EXAMPLE 46

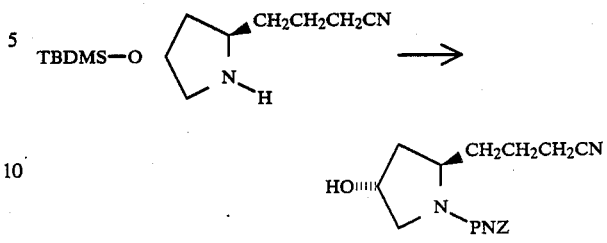

(2R,4R)-2-(3-Cyanopropyl)-4-t-butyldimethylsilyloxypyrrolidine (1.02 g) was dissolved in 22 ml of dioxane and 15.5 ml of water, and 7 ml of 4N sodium hydroxide solution was added thereto, followed by refluxing for 2 hours. The reaction mixture was neutralized with 6N hydrochloric acid and distilled to remove the solvent. The residue was dissolved in 10 ml of water, and 0.98 ml of triethylamine and a solution of 1.67 g of 2-(p-nitrobenzyloxycarbonyl)thio-4,6-dimethylpyrimidine in 20 ml of dimethylformamide were added thereto, followed by stirring at room temparature for 5 hours. The reaction mixture was diluted with ethyl acetate, washed successively with brine, dilute hydrochloric acid and brine, dried over anhydrous sodium sulfate and distilled to remove the solvent. The residue was purified by silica gel column chromatography to obtain (2R,4R)-1-(p-nitrobenzyloxy)carbonyl-2-(3-cyanopropyl)-4-hydroxypyrrolidine.

IR$_{max}^{neat}$ cm$^{-1}$: 2250, 1700, 1520, 1402, 1345.

REFERENCE EXAMPLE 47

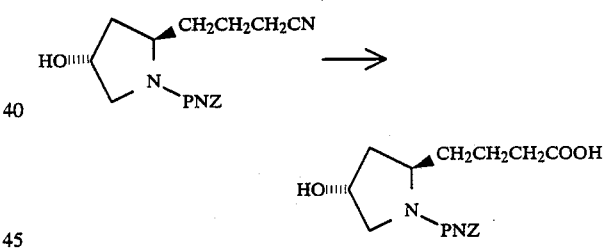

Following the procedure as in Reference Example 9 but using (2R,4R)-1p-nitrobenzyloxycarbonyl-2-(3-cyanopropyl)-4-hydroxypyrrolidine as the starting material, (2R,4R)-1-p-nitrobenzyloxycarbonyl-2-(3-carboxypropyl)-4-hydroxypyrrolidine was obtained.

IR$_{max}^{neat}$ cm$^{-1}$: 1700, 1618 (sh), 1518, 1402, 1343.

REFERENCE EXAMPLE 48

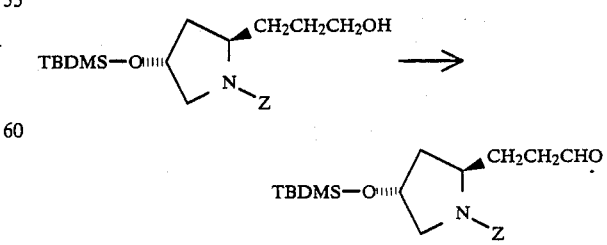

Oxalyl chloride (0.32 ml) was dissolved in 7.9 ml of dry dichloromethane, and 0.56 ml of dry dimethylsulfoxide was added thereto at −45° to −56° C. in a nitrogen stream, followed by stirring at the same temperature for 20 minutes. To the reaction mixture was added a solution of 1.30 g of (2R,4R)-1-benzyloxycarbonyl-2-(3-hydroxypropyl)-4-t-butyldimethylsilyloxypyrrolidine in 6.2 ml of dry dichloromethane at −50° to −60° C., followed by stirring at the same temperature for 15 minutes. Then, 2.2 ml of triethylamine was added thereto at −50° to −60° C. The temparature was elevated to room temperature, and the reaction mixture was washed successively with brine, dilute hydrochloric acid and brine, dried over anhydrous sodium sulfate and distilled to obtain (2R,4R)-1-benzyloxycarbonyl-2-(2-formylethyl)-4-t-butyldimethylsilyloxypyrrolidine.

IR$_{max}^{neat}$ cm$^{-1}$: 1703, 1413, 1359, 1255, 1110.

In the same procedure as above, (2S,4R)-1-p-nitrobenzyloxycarbonyl-2-formylmethyl-4-t-butyldimethylsilyloxypyrrolidine was obtained from (2R,4R)-1-p-nitrobenzyloxycarbonyl-2-(2-hydroxyethyl)-4-t-butyldimethylsilyloxypyrrolidine.

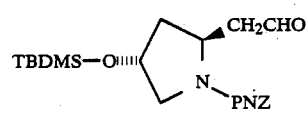

IR$_{max}^{neat}$ cm$^{-1}$: 1723 (sh), 1703, 1520, 1400, 1342.

REFERENCE EXAMPLE 49

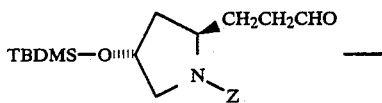

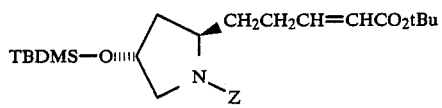

t-Butyloxycarbonylmethyltriphenylphosphonium bromide (2.15 g) was dissolved in 40 ml of dichloromethane, and 30 ml of a saturated sodium bicarbonate solution was added thereto, followed by stirring at room temperature for 5 minutes. The dichloromethane layer was separated and dried over anhydrous sodium sulfate. After filtration, a solution of 1.29 g of (2R,4R)-1-benzyloxycarbonyl-2-(2-formylethyl)-4-t-butyldimethylsilyloxypyrrolidine in 30 ml of dichloromethane was added to the filtrate, followed by refluxing for 30 minutes. After removal of the solvent, the residue was purified by silica gel column chromatography to obtain (2R,4R)-1-benzyloxycarbonyl-2-(3-t-butoxycarbonylmethylidenepropyl)-4-t-butyldimethylsilyloxypyrrolidine.

IR$_{max}^{neat}$ cm$^{-1}$: 1702, 1649, 1408, 1363, 1148.

REFERENCE EXAMPLE 50

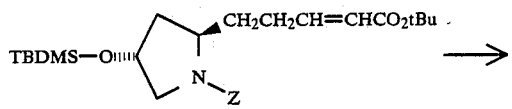

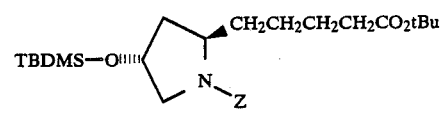

(2R,4R)-1-Benzyloxycarbonyl-2-(3-t-butoxycarbonylmethylidenepropyl)-4-t-butyldimethylsilyloxypyrrolidine (1.17 g) was dissolved in 24 ml of ethanol, and 350 mg of 5% palladium carbon was added thereto, followed by hydrogenation at room temperature under 1 atm for 3 hours. The catalyst was removed by filtration, and the filtrate was distilled to obtain (2R,4R)-2-(4-t-butoxycarbonylbutyl)-4-t-butyldimethylsilyloxypyrrolidine.

IR$_{max}^{neat}$ cm$^{-1}$: 1730, 1460, 1365, 1250, 1147.

REFERENCE EXAMPLE 51

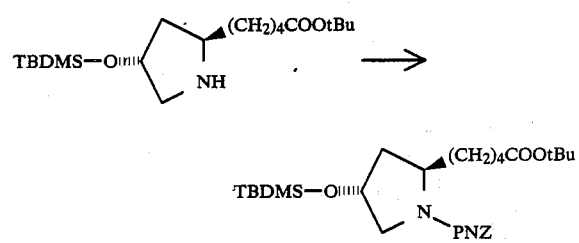

S-p-Nitrobenzyloxycarbonyl-4,6-dimethyl-2-mercaptopyrimidine (719 mg) was added to 770 mg of (2R,4R)-2-(4-t-butoxycarbonylbutyl)-4-t-butyldimethylsilyloxypyrrolidine in 7 ml of tetrahydrofuran and stirred at room temperature for 2 hours. The reaction mixture was diluted with ethyl acetate, washed successively with brine, dilute hydrochloric acid and brine, dried over anhydrous sodium sulfate and distilled to remove the solvent. The residue was purified by silica gel chromatography to obtain (2R,4R)-1-p-nitrobenzyloxycarbonyl-2-(4-t-butoxycarbonylbutyl)-4-t-butyldimethylsilyloxypyrrolidine.

IR$_{max}^{neat}$ cm$^{-1}$: 1730 (sh), 1712, 1528, 1402, 1350.

REFERENCE EXAMPLE 52

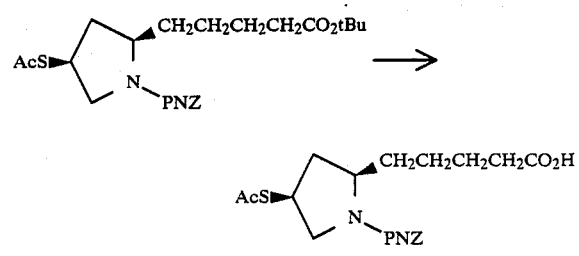

(2R,4S)-1-p-Nitrobenzyloxycarbonyl-2-(4-t-butyloxycarbonylbutyl)-4-acetylthiopyrrolidine (493 mg) was dissolved in 2.5 ml of trifluoroacetic acid, followed by stirring at room temperature for 15 minutes. The reaction mixture was distilled off to obtain (2R,4S)-1-p-nitrobenzyloxycarbonyl-2-(4-carboxybutyl)-4-acetylthiopyrrolidine.

IR$_{max}^{neat}$ cm$^{-1}$: 1702, 1520, 1402, 1343.

REFERENCE EXAMPLE 53

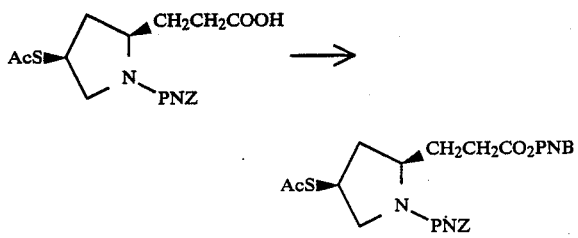

(2R,4S)-1-p-Nitrobenzyloxycarbonyl-2-(2-carboxyethyl)-4-acetylthiopyrrolidine (323 mg) was dissolved in 3.3 ml of dry dimethylformamide, and 150 mg of triethylamine and 324 mg of p-nitrobenzyl bromide were added thereto, followed by stirring at room temperature for 3.5 hours. To the reaction mixture was added water, and the resulting mixture was extracted with ethyl acetate, washed successively with a saturated sodium bicarbonate solution, water, dilute hydrochloric acid and water, dried over anhydrous sodium sulfate and distilled off to remove the solvent. The residue was purified by silica gel column chromatography to obtain (2R,4S)-1-p-nitrobenzyloxycarbonyl-2-(2-p-nitrobenzyloxycarbonylethyl)-4-acetylthiopyrrolidine.

$IR_{max}^{neat}$ cm$^{-1}$: 1732, 1697, 1515, 1393, 1342.

REFERENCE EXAMPLE 54

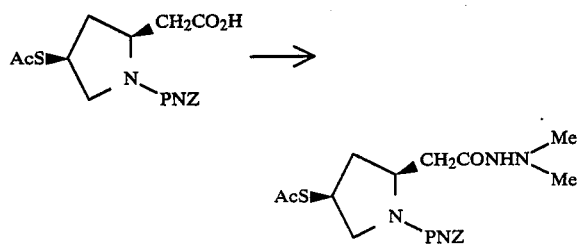

(2R,4S)-1-p-Nitrobenzyloxycarbonyl-2-carboxymethyl-4-acetylthiopyrrolidine (218 mg) was dissolved in 2.2 ml of dry tetrahydrofuran, and 63 mg of N,N-dimethylhydrazine and 159 mg of N,N-dicyclohexylcarbodiimide were added thereto, followed by stirring at room temperature for 3 hours. After any insoluble material was removed by filtration, the filtrate was distilled to remove the solvent. The residue was purified by silica gel thin layer chromatography to obtain (2R,4S)-1-p-nitrobenzyloxycarbonyl-2-[(N,N-dimethylhydrazinocarbonyl)methyl]-4-acetylthiopyrrolidine.

$IR_{max}^{neat}$ cm$^{-1}$: 1700, 1660, 1515, 1418, 1340.

REFERENCE EXAMPLE 55

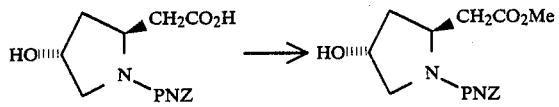

(2R,4R)-1-p-Nitrobenzyloxycarbonyl-2-carboxymethyl-4-hydroxypyrrolidine (5.39 g) was dissolved in 54 ml of dry methanol, and 0.9 ml of conc. sulfuric acid was added thereto, followed by refluxing for 4 hours. The reaction mixture was neutralized with 1N sodium hydroxide solution and distilled to remove the solvent. To the residue was added ethyl acetate, and the mixture was washed with water, dried over anhydrous sodium sulfate and distilled to obtain (2S,4R)-1-p-nitrobenzyloxycarbonyl-2-methoxycarbonylmethyl-4-hydroxypyrrolidine.

$IR_{max}^{neat}$ cm$^{-1}$: 1740, 1708, 1525, 1440, 1348.

In the same procedure as above, (2R,4R)-1-p-nitrobenzyloxycarbonyl-2-(2-methoxycarbonylethyl)-4-hydroxypyrrolidine was obtained from (2R,4R)-12-p-nitrobenzyloxycarbonyl-2(2-carboxyethyl)-4-hydroxypyrrolidine.

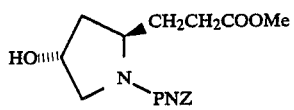

$IR_{max}^{neat}$ cm$^{-1}$: 1730, 1688, 1523, 1352.

REFERENCE EXAMPLE 56

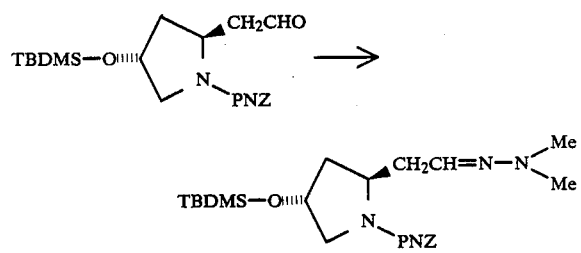

(2S,4R)-1-p-Nitrobenzyloxycarbonyl-2-formylmethyl-4-t-butyldimethylsilyloxypyrrolidine (423 mg) was dissolved in 2 ml of ethanol, and 65 mg of N,N-dimethylhydrazine was added thereto, followed by stirring at room temperature for 15 minutes. To the reaction mixture was added ethyl acetate, and the mixture was washed with water, dried over anhydrous sodium sulfate and distilled to remove the solvent. The residue was purified by silica gel thin layer chromatography to obtain (2R,4R)-1-p-nitrobenzyloxycarbonyl-2-(2-dimethylhydrazinoethyl)-4-t-butyldimethylsilyloxypyrrolidine.

$IR_{max}^{neat}$ cm$^{-1}$: 1713, 1528, 1405, 1348.

REFERENCE EXAMPLE 57

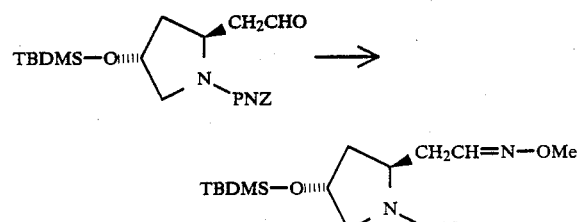

Methoxyamine hydrochloride (124 mg) was dissolved in 4 ml of water, and sodium acetate (244 mg) and a solution of 418 mg of (2S,4R)-1-p-nitrobenzyloxycarbonyl-2-formylmethyl-4-t-butyldimethylsilyloxypyrrolidine in 5 ml of ethanol were added thereto at room temperature, followed by stirring at the same temperature for 30 minutes. The reaction mixture was diluted with ethyl acetate, washed successively with water and a saturated sodium bicarbonate solution, dried over anhydrous sodium sulfate and distilled to remove the solvent. The residue was purified by silica gel thin layer chromatography to obtain (2R,4R)-1-p-nitrobenzyloxy-2-(2-methoxyimino)ethyl-4-t-butyl-dimethylsilyoxypyrrolidine.

IR$_{max}^{neat}$ cm$^{-1}$: 1705, 1523, 1400, 1343.

REFERENCE EXAMPLE 58

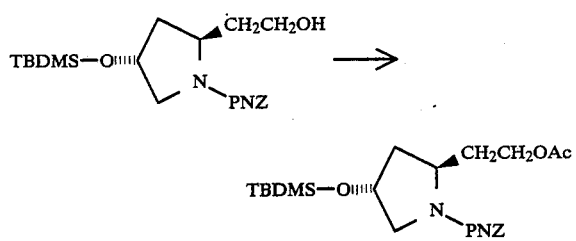

(2R,4R)-1-p-Nitrobenzyloxycarbonyl-2-(2-hydroxyethyl)-4-t-butyldimethylsilyloxypyrrolidine (900 mg) was dissolved in 2.25 ml of dry pyridine, and 2.25 ml of acetic anhydride was added to the solution at room temperature, followed by stirring for 1 hour. The reaction mixture was diluted with diethyl ether, washed successively with brine, a diluted aqueous hydrochloric acid, brine, a diluted aqueous sodium hydroxide solution and brine, dried over anhydrous sodium sulfate to give (2R,4R)-1-p-nitrobenzyloxycarbonyl-2-(2-acetoxyethyl)-4-t-butyldimethylsilyloxypyrrolidine.

IR$_{max}^{neat}$ cm$^{-1}$: 1730, 1705, 1522, 1408, 1350.

In the same procedure as above, (2R,4R)-1-p-nitrobenzyloxycarbonyl-2-(3-acetoxypropyl)-4-t-butyl-dimethylsilyloxypyrrolidine was obtained from (2R,4R)-1-p-nitrobenzyloxycarbonyl-2-(3-hydroxypropyl)-4-t-butyldimethylsilyloxypyrrolidine.

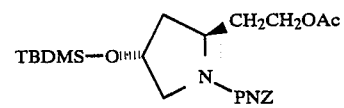

IR$_{max}^{neat}$ cm$^{-1}$: 1739, 1712, 1522, 1401, 1345.

REFERENCE EXAMPLE 59

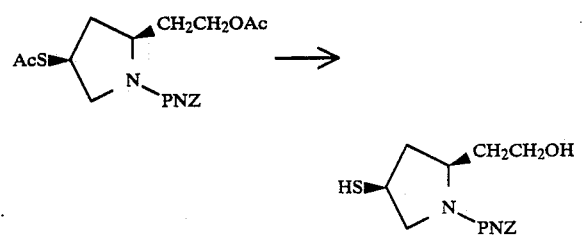

(2R,4S)-1-p-Nitrobenzyloxycarbonyl-2-(2-acetoxyethyl)-4-acetylthiopyrrolidine (204 mg) was dissolved in 5 ml of methanol and 1 ml of 1N sodium hydroxide solution was added thereto at room temperature under nitrogen stream, followed by stirring for 30 minutes. 1H Hydrochloric acid (1.2 ml) was added to the reaction mixture. The resulting mixture was diluted with ethyl acetate, washed with brine five times, dried over anhydrous sodium sulfate and evaporated to give an oily residue, which was purified by silica gel thin layer chromatogaraphy to give (2R,4S)-1-p-nitrobenzyloxycarbonyl-2-(2-hydroxyethyl)-4-mercaptopyrrolidine.

IR$_{max}^{neat}$ cm$^{-1}$: 1690, 1522, 1432, 1408, 1348.

In the same procedure as above, (2R,4S)-1-p-nitrobenzyloxycarbonyl-2-(3-hydroxypropyl)-4-mercaptopyrrolidine was obtained from (2R,4S)-1-p-nitrobenzyloxycarbonyl-2-(3-acetoxypropyl)-4-mercaptopyrrolidine.

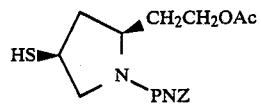

IR$_{max}^{neat}$ cm$^{-1}$: 1695, 1522, 1433, 1410, 1350.

EXAMPLE 1

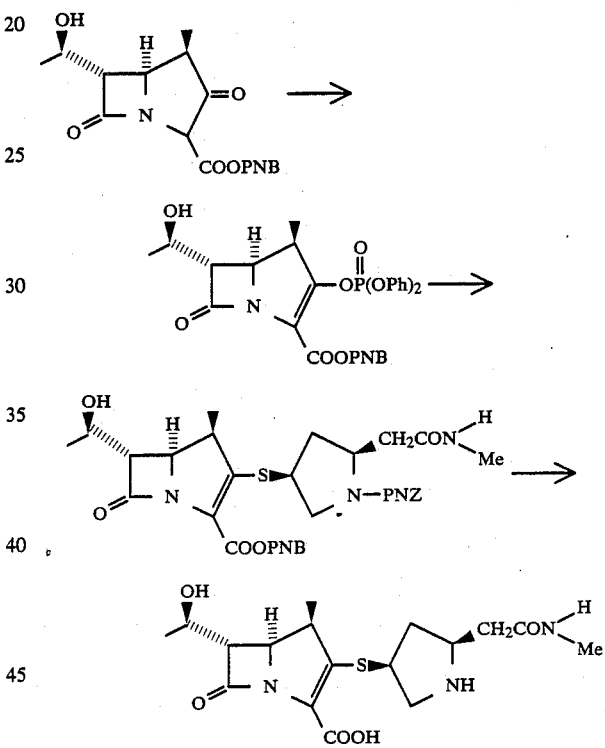

(a) (4R,5R,6S,8R)-p-Nibrobenzyl-4-methyl-6-(1-hydroxyethyl)-1-azabicyclo[3.2.0]-hept-3,7-dione-2-carboxylate (511 mg) was dissolved in 3.1 ml of dry acetonitrile and 154 mg of diisopropylethylamine. A solution of 317 mg of diphenyl chlorophosphate in 1 ml of dry acetonitrile was added thereto in a nitrogen stream under ice-cooling, followed by stirring for 1 hour. The mixture was cooled at −35° C., and 154 mg of diisopropylethylamine and 420 mg of (2R,4S)-1-p-nitrobenzyloxycarbonyl-2-methylaminocarbonylmethyl-4-mercaptopyrrolidine were added thereto, followed by stirring at −20° to −30° C. for 1 hour. The reaction mixture was diluted with ether-dichloromethane (4:1), washed successively with water, and aqueous potassium dihydrogen phosphate solution and water, dried over an hydrous magnesium sulfate and concentrated. The residue was purified by silica gel thin layer chromatography to obtain 453 mg of (4R,5S,6S,8R,2'R,4'S)-p-nitro benzyl-3-[(1-p-nitrobenzyloxycarbonyl-2- methylaminocarbonylmethylpyrrolidin)-4-ylthio]-4-methyl-6-(1-hydroxyethyl)-1-azabicyclo[3.2.0]-hept-2-en-7-one-2-carboxylate.

IR$_{max}^{neat}$ cm$^{-1}$: 1762, 1700, 1655, 1520, 1403, 1343, 1212.

NMR δ(CDCl$_3$): 1.27 (3H, d, J=7 Hz), 1.34 (3H, d, J=6.2 Hz), 2.76 (3H, d, J=4.6 Hz), 5.21 (2H,s), 5.47 (1H, d, J=13.6 Hz), 6.94 (1H, bs), 8.18 (4H, d, J=8.8 Hz).

(b) (4R,5S,6S,8R,2'R,4'S)-p-Nitrobenzyl-3-[(1-p-nitrobenzyloxycarbonyl-2-methylaminocarbonylmethylpyrrolidin)-4-ylthio]-4-methyl-6-(1-hydroxyethyl)-1-azabicyclo[3.2.0]-hept-2-en-7-one-2-carboxylate (453 mg) was dissolved in 21 ml of tetrahydrofuran. A morpholinopropanesulfonic acid buffer solution (pH 7.0) (14 ml) and 10% palladium-carbon (obtained by hydrogenation in water under atmospheric pressure of hydrogen at room temperature for 1 hour, filtration and washing with water) (549 mg) were added thereto. The resultant mixture was hydrogenated under atmospheric pressure of hydrogen at room temperature for 3 hours. The catalyst was removed by filtration, and the filtrate was distilled under reduced pressure to remove tetrahydrofuran. The residual solution was washed with dichloromethane, and the aqueous layer was again distilled under reduced pressure to remove the organic solvent. The residual solution was subjected to polymer chromatography (CHP-20P) to obtain (4R,5S,6S,8R,2'R,4,'S)-3-[(2-methylaminocarbonylmethylpyrrolidin)-4-ylthio]-4-methyl-6-(1-hydroxyethyl)-1-azabicyclo[3.2.0]-hept-2-en-7-one-2-carboxylic acid from the fraction eluted with 1% tetrahydrofuran-water.

UV$_{max}^{H_2O}$ nm: 298.

IR$_{max}^{KBr}$ cm$^{-1}$: 1748, 1650, 1585, 1380, 1250.

NMR δ(D$_2$O): 1.19 (3H, d, J=7 Hz), 1.27 (3H, d, J=6 Hz), 2.72 (3H, s), 2.79 (2H, d, J=7 Hz), 3.44 (1H, dd, J=2.6 Hz and 6Hz), 4.19 (1H, d, J=2.6 Hz).

EXAMPLE 2

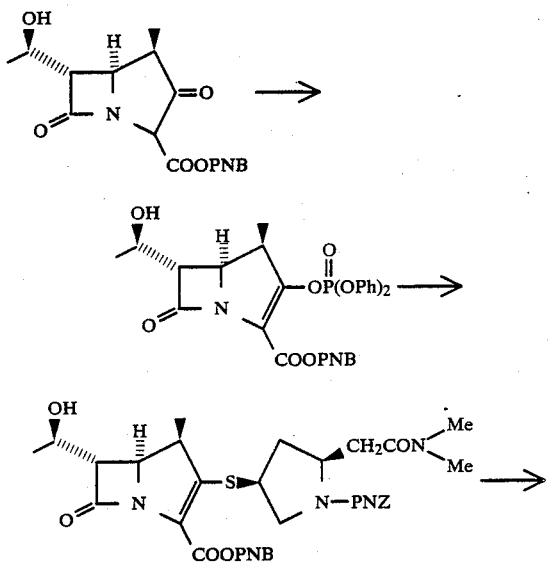

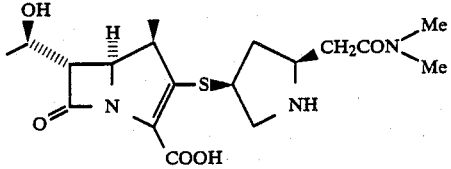

(a) (4R,5R,6S,8R)-p-Nitrobenzyl-4-methyl-6-(1-hydroxyethyl)-1-azabicyclo[3.2.0]-hept-3,7-dione-2-carboxylate (98 mg) was dissolved in 1 ml of dry acetonitrile and diisopropylethylamine (39 mg). A solution of 81 mg of diphenyl chlorophosphate in 0.5 ml of dry acetonitrile was added thereto in a nitrogen stream under ice-cooling, followed by stirring for 1 hour. The mixture was cooled at −35° C., and 35 mg of diisopropylethylamine and a solution of 99 mg of [2R,4S]-1-p-nitrobenzyloxycarbonyl-2-dimethylaminocarbonylmethyl-4-mercaptopyrrolidine in 1 ml of dry acetonitrile were added thereto, followed by stirring at −20° to −30° C. for 1 hour. The mixture was diluted with etherdichloromethane (4:1), washed successively with water, an aqueous potassium dihydrogen phosphate solution and water, dried over anhydrous magnesium sulfate and concentrated. The residue was purified by silica gel thin layer chromatography to obtain 88 mg of (4R,5S,6S,8R,2'R,4'S)-p-nitrobenzyl-3-[(1-p-nitrobenzyloxycarbonyl-2-dimethylaminocarbonylmethylpyrrolidin)-4-ylthio]-4-methyl-6-(1-hydroxyethyl)-1-azabicyclo[3.2.0]-hept-2-en-7-one-2-carboxylate.

IR$_{max}^{CHCl_3}$ cm$^{-1}$: 1770, 1690, 1520, 1400, 1345, 1105.

NMR δ(CDCl$_3$): 1.28 (3H, d, J=6.8 Hz), 1.36 (3H, d, J=7 Hz), 5.22 (2H, s), 5.49 (1H, d, J=13.9 Hz), 8.21 (4H, d, J=8.8 Hz).

(b) (4R,5S,6S,8R,2'R,4'S)-p-Nitrobenzyl-3-[(1-p-nitrobenzyloxycarbony-2-dimethylaminocarbonylmethylpyrrolidin)-4-ylthio]-4-methyl-6-(1-hydroxyethyl)-1-azabicyclo[ cyclo[3.2.0]-hept-2-en-7-one-2-carboxylate (83 mg) was dissolved in 3.7 ml of tetrahydrofuran, and a morpholinopropanesulfonic acid buffer solution (pH 7.0) (2.4 ml) and 10% palladium-carbon as prepared in Example 1 b) (101 mg) were added thereto. The resulting mixture was hydrogenated under atmospheric pressure of hydrogen at room temperature for 3 hours. The catalyst was removed by filtration, and the filtrate was concentrated under reduced pressure. The residual solution was washed with dichloromethane, and the aqueous layer was again distilled under reduced pressure to remove the organic solvent. The residual solution was subjected to polymer chromatography (CHP-20P) to obtain (4R,5S,6S,8R,2'R,4'S)-3-[(2-dimethylaminocarbonylmethyl-pyrrolidin)-4-ylthio]-4-methyl-6-(1-hydroxyethyl)-1-azabicyclo[3.2.0]-hept-2-en-7-one-2-carboxylic acid from the fraction eluted with 1% tetrahydrofuran-water.

UV $_{max}^{H2O}$ nm: 296.

IR $_{max}^{KBr}$ cm$^{-1}$: 1752, 1630, 1390, 1260, 1148.

NMR δ (D$_2$O) 1.20 (3H, d, J=6.9 Hz), 1.27 (3H, d, J=6.3 Hz), 2.91 (3H, s), 3.02 (3H, s).

EXAMPLE 3

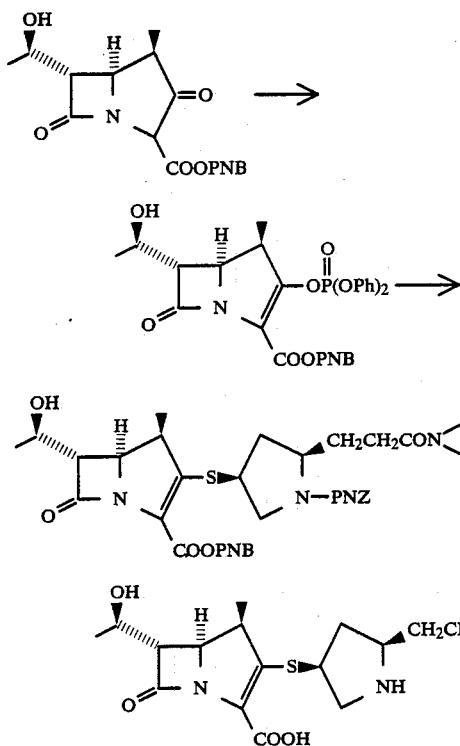

(a) (4R,5R,6S,8R)-p-Nitrobenzyl-4-methyl-6-(1-hydroxyethyl)-1-azabicyclo[3.2.0]-hept-3,7-dione-2-carboxylate (101 mg) was dissolved in 1.5 ml of dry acetonitrile and 37 mg of diisopropylethylamine. A solution of 77 mg of diphenyl chlorophosphate in 0.8 ml of dry acetonitrile was added thereto in a nitrogen stream under ice-cooling, followed by stirring for 1 hour. The mixture was cooled at $-35°$ C., and 40 mg of diisopropylethylamine and a solution of 117 mg of (2R,4S)-1-p-nitrobenzyloxycarbonyl-2-(2-dimethylaminocarbonylethyl)-4-mercaptopyrrolidine in 1 ml of dry acetonitrile were added thereto, followed by stirring for 1 hour at $-20°$ to $-30°$ C. The reaction mixture was diluted with ether-dichloromethane (4:1), washed successively with water, an aqueous potassium dihydrogen phosphate solution and water, dried over anhydrous magnesium sulfate and concentrated. The residue was purified by silica gel thin layer chromatography to obtain 90 mg of (4R,5S,6S,8R,2'R,4'S)-p-nitrobenzyl-3-[(1-p-nitrobenzyloxycarbonyl-2-(2-dimethylaminocarbonylethyl)-pyrrolidin)-4-ylthio]-4-methyl-6-(1-hydroxyethyl)-1-azabicyclo[3.2.0]-hept-2-en-7-one-2-carboxylate.

IR $_{max}{}^{neat}$ cm$^{-1}$: 1763, 1700, 1625, 1518, 1400, 1343.

NMR δ (CDCl$_3$) 1.26 (3H, d, J =7.9 Hz), 1.35 (3H, d, J =6.4 Hz), 2.91 (3H, s), 2.95 (3H, s), 5.21 (2H, s), 5.48 (1H, d, J =13.6 Hz), 8.20 (4H, d, J =8.8 Hz).

(b) (4R,5S,6S,8R,2'R,4'S)-p-Nitrobenzyl-3-[1-p-nitrobenzyloxycarbonyl-2-(2-dimethylaminocarbonylethyl)-pyrrolidin)-4-ylthio]-4-methyl-6-(1-hydroxyethyl)-1-azabicyclo[3.2.0]-hept-2-en-7-one-2-carboxylate (90 mg) was dissolved in 4 ml of tetrahydrofuran. A morpholinopropanesulfonic acid buffer solution (pH 7.0) (2.7 ml) and 10% palladium-carbon as prepared in Example 1 b) (109 mg) were added thereto. The resulting mixture was hydrogenated under atmospheric pressure of hydrogen at room temperature for 3 hours. The catalyst was removed by filtration, and the filtrate was distilled under reduced pressure to remove tetrahydrofuran. The residual solution was washed with dichloromethane, and the aqueous layer was again distilled under reduced pressure to remove the organic solvent. The residual solution was subjected to polymer chromatography (CHP-20P) to obtain (4R,5S,6S,8R,2'R,4'S)-3-[[2-(2-dimethylaminocarbonylethyl pyrrolidin]-4-ylthio]-4-methyl-6-(1-hydroxyethyl)-1-azabicyclo[3.2.0]-hept-2 en-7-one-2-carboxylic acid from the fraction eluted with I % tetrahydrofuran-water.

Uv$_{max}{}^{H_2max\,O}$ nm: 298.

IR $_{max}{}^{KRr}$ cm$^{-1}$: 1757, 1620, 1385, 1260, 1145.

NMR δ (D$_2$O): 1.18 (3H, , J =7.3 Hz), 1.26 (3H, d, J =6.3 Hz), 2.90 (3H, s), 3.03 (3H, s).

EXAMPLE 4

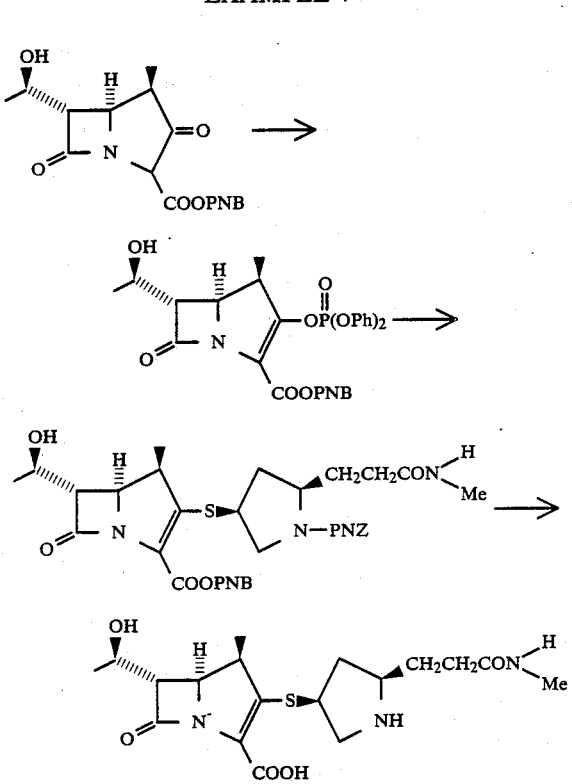

(a) (4R,5R,6S,8R)-p-Nitrobenzyl-4-methyl-6-(1-hydroxyethyl)-1-azabicyclo [3.2.0]-hept-3,7-dione-2-carboxylate (78 mg) was dissolved in 1 ml of dry acetonitrile and 29 mg of diisopropylethylamine. A solution of 59 mg of diphenyl chlorophosphate in 0.6 ml of dry acetonitrile was added thereto in a nitrogen stream under ice-cooling, followed by stirring for 1 hour. The mixture was cooled at $-35°$ C., and 26 mg of diisopropylethylamine and a solution of 72 mg of (2R,4S)-1-p-nitrobenzyloxycarbonyl-2-(2-methylaminocarbonylethyl)-4-mercaptopyrrolidine in 1 ml of dry acetonitrile were added thereto, followed by stirring at $-20°$ to $-30°$ C. for 1 hour. The reaction mixture was diluted with ether-dichloromethane (4:1), washed successively with water, an aqueous potassium dihydrogen phosphate solution and water, dried over anhydrous magnesium sulfate and concentrated. The residue was purified by silica gel thin layer chromatography to obtain 68 mg of (4R,5S,6S,8R,2'R,4'S)-p-nitrobenzyl-3-[(1-p-nitrobenzyloxy-carbonyl-2-(2-methylaminocarbonylethyl)pyrrolidin)-4-ylthio]-4-methyl-6-(1-hydroxyethyl)-1-azabicyclo[3.2.0]-hept-2-en-7-one-2-carboxylate.

IR$_{max}$$^{CHCl_3}$ cm$^{-1}$: 1767, 1695, 1518, 1400, 1341.

NMR δ (acetone-d$_6$) 1.27 (3H, d, J=5.9 Hz), 1.28 (3H, d, J =7 Hz), 2.68 (3H, d, J =4.6 Hz), 5.26 (2H, s).

(b) (4R,5S,6S,8R,2'R,4'S)-p-Nitrobenzyl-3-[(1-p-nitrobenzyloxycarbonyl-2-(2-methylaminocarbonylethyl)-pyrrolidin)-4-ylthio]-4-methyl-6-(1-hydroxyethyl)-1-azabicyclo[3.2.0]-hept-2-en-7-one-2-carboxylte (68 mg) was dissolved in 2.8 ml of 25% dimethylformamide-tetrahydrofuran. A morpholinopropanesulfonic acid buffer solution (pH 7.0) (1.4 ml) and 10% palladium-carbon as prepared in Example 1 b) (83 mg) were added thereto. The resulting mixture was hydrogenated under atmospheric pressure of hydrogen at room temperature for 3 hours. The catalyst was removed by filtration, and the filtrate was distilled under reduced pressure to remove tetrahydrofuran. The residual solution was washed with dichloromethane, and the aqueous layer was again distilled under reduced pressure to remove the organic solvent. The residual solution was subjected to polymer chromatography (CHP-20P) to obtain (4R,5S,6S,8R,2'R,4'S)-3-[(2-(2-methylaminocarbonylethyl)-pyrrolidin)-4-ylthio]-4-methyl-6-(1-hydroxyethyl)-1-azabicyclo[3.2.0]-hept-2-en-7-one-2-carboxylic acid from the fraction eluted with 1% tetrahydrofuran-water.

UV $_{max}$$^{H_2O}$ nm: 299.

IR $_{max}$$^{KBr}$ cm$^{-1}$: 1751, 1640, 1592, 1382, 1253.

NMR δ (D$_2$O) 1.19 (3H, d, J =7.3 Hz), 1.27 (3H, d, J =6.3 Hz), 2.71 (3H, s), 3.44 (1H, dd, J =1.7 Hz and 5.9 Hz).

EXAMPLE 5

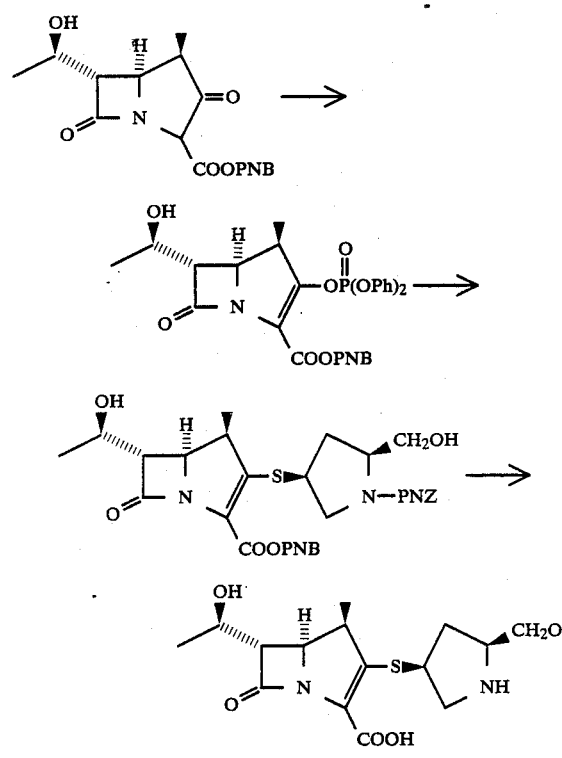

(a) (4R,5R,6S,8R)-p-Nitrobenzyl-4-methyl-6-(1-hydroxyethyl)-1-azabicyclo[3.2.0]-hept-3,7-dione-2-carboxylate (123 mg) was dissolved in 2 ml of dry acetonitrile and 45 mg of diisopropyethylamine. A solution of 93 mg of diphenyl chlorophosphate in 1 ml of dry acetonitrile was added thereto in a nitrogen stream under ice-cooling, followed by stirring for 1 hour. The mixture was cooled at −35° C., and 49 mg of diisopropylethylamine and a solution of 117 mg of (2S,4S)-1-p-nitrobenzyloxycarbonyl-2-hydroxymethyl-4-mercaptopyrrolidine in 1 ml of dry acetonitrile were added thereto, followed by stirring at −20° C. to −30° C. for 1 hour. The reaction mixture was diluted with ether-dichloromethane (4:2), washed successively with water, an aqueous potassium dihydrogen phosphate solution and water, dried over anhydrous magnesium sulfate and concentrated. The residue was purified by silica gel thin layer chromatography to obtain 136 mg of (4R,5S,6S, 8R,2'S,4'S)-p-nitrobenzyl-3-[(1-p-nitrobenzyloxycarbonyl-2-hydroxymethyl-pyrrolidin)-4-ylthio]-4-methyl-6-(1-hydroxyethyl)-1-azabicyclo[3.2.0]-hept-2-en-7-one-2-carboxylate.

IR $_{max}$$^{neat}$ cm$^{-1}$: 1762, 1695, 1518, 1340, 1210.

NMR δ (CDCl$_3$) 1.27 (3H, d, J =6.4 Hz), 1.33 (3H, d, J =5.7 Hz), 5.22 (2H, s), 5.46 (1H, d, J =13.9 Hz), 8.18 (4H, d, J =8.6 Hz).

(b) (4R,5S,6S,8R,2'S,4'S)-p-Nitrobenzyl-3-[(1-p-nitrobenzyloxycarbonyl-2-hydroxymethylpyrrolidin)-4-ylthio]-4-methyl-6-(1-hydroxyethyl)-1-azabicyclo[3.2.0]-hept-2-en-7-one-2-carboxylate (136 mg) was dissolved in 6 ml of tetrahydrofuran. A morpholinopropanesulfonic acid buffer solution (pH 7.0) (4 ml) and 10% palladium-carbon as prepared in Example 1 b) (165 mg) were added thereto. The resultant mixture was hydrogenated under atmospheric pressure of hydrogen at room temperature for 3 hours. The catalyst was removed by filtration, and the filtrate was distilled under reduced pressure to remove tetrahydrofuran. The residual solution was washed with dichloromethane, and the aqueous layer was again distilled under reduced pressure to remove the organic solvent. The residual solution was subjected to polymer chromatography (CHP-20P) to obtain (4R,5S,6S,8R,2'S,4'S)-3-(2-hydroxymethylpyrrolidin)-4-ylthio]-4-methyl-6-(1-hydroxyethyl)-1-azabicyclo[3.2.0]-hept-2-en-7-one-2-carboxylic acid from the fraction eluted with 1% tetrahydrofuran-water.

UV $_{max}$$^{H_2O}$ nm: 298.

IR $_{max}$$^{KBr}$ cm$^{-1}$: 1748, 1585, 1386, 1252.

NMR δ (D$_2$O): 1 20 (3H, d, J=7.3 Hz), 1.27 (3H, d, J=6.3 Hz).

EXAMPLE 6

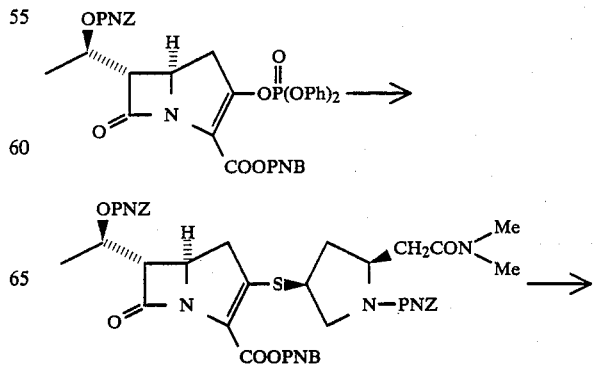

-continued

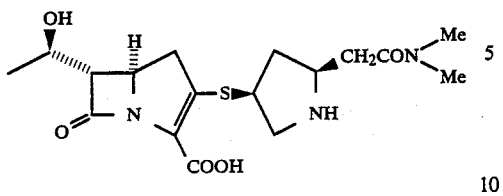

(a) (5R,6S,8R)-p-Nitrobenzyl-3-(diphenylphosphoryloxy)-6(1-p-nitrobenzyloxycarbonyloxyethyl)-1-azabicyclo[3.2.0]-hept-2-en-7-one-2carboxylate (182 mg) was dissolved in 2 ml of dry acetonitrile, and 34 mg of diisopropylethylamine and 88 mg of [2R,4S]-1-p-nitrobenzyloxycarbonyl-2-dimethylaminocarbonylmethyl-4-mercaptopyrrolidine were added thereto in a nitrogen stream under ice-cooling, followed by stirring for 15 minutes. The reaction mixture was diluted with ether-dichloromethane, washed successively with water, an aqueous potassium dihydrogen phosphate solution and water, dried over anhydrous magnesium sulfate and concentrated. The residue was purified by silica gel thin layer chromatography to obtain 135 mg of (5R,6S,8R,2′R,4′S)-p-nitrobenzyl-3-[(1-p-nitro-benzyloxycarbonyl-2-dimethylaminocarbonylmethylpyrrolidin)-4-ylthio]-6-(1-p-nitrobenzyloxycarbonyloxyethyl)-1-azabicyclo[3.2.0]-hept-2-en-7-one-2-carboxylate.

IR $_{max}{}^{CHCl_3}$ cm$^{-1}$: 1780, 1743, 1700, 1630, 1517, 1255.

NMR δ (CDCl$_3$) 1.49 (3H, d, J=6.4 Hz), 2.92 (6H, s), 5.22 (2H, s), 5.26 (2H, s), 5.46 (1H, d, J =13.9 Hz), 8.22 (6H, d, J =8.1 Hz).

(b) (5R,6S,8R,2′R,4′S)-p-Nitrobenzyl-3-[(1-p-nitrobenzyloxycarbonyl-2-dimethylaminocarbonylmethylpyrrolidin)-4-ylthio]-6-(1-p-nitrobenzyloxycarbonyloxyethyl)-1-azabicyclo[3.2.0]-hept-2-en-7-one-2-carboxylate (135 mg) was dissolved in 5.1 ml of tetrahydrofuran, and a morpholinopropanesulfonic acid buffer solution (pH 7.0) (3.4 ml) and 10% palladium-carbon as prepared in Example 1 b) (164 mg) were added thereto. The resultant mixture was hydrogenated under atmospheric pressure of hydrogen at room temperature for 4 hours. The catalyst was removed by filtration, and the filtrate was distilled under reduced pressure to remove tetrahydrofuran. The residual solution was washed with dichloromethane, and the aqueous layer was again distilled under reduced pressure to remove the organic solvent. The residual solution was subjected to, polymer chromatography (CHP-20P) to obtain (5R,6S,8R,2R,4,S)-3-(2-dimethylaminocarbonylmethylpyrrolidin)-4-ylthio]-6-(1-hydroxyethyl)-1-azabicyclo[3.2.0]-hept-2-en-7-one-2-carboxylic acid from the fraction eluted with 1% tetrahydrofuran-water.

UV$_{max}{}^{H_2O}$ nm: 298.

IR $_{max}{}^{KBr}$ cm$^{-1}$: 1752, 1620, 1580, 1380, 1240, 1140.

NMR δ (D$_2$O): 1.26 (3H, d, J =6.3 Hz), 2.91 (3H, s), 3.02 (3H, s).

EXAMPLE 7

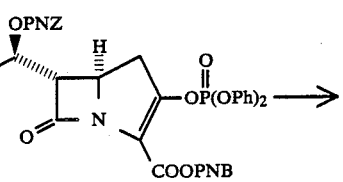

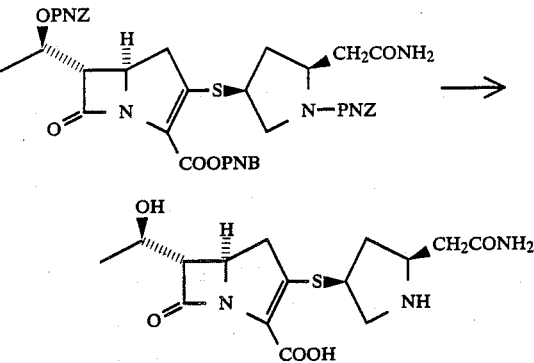

(a) (5R,6S,8R)-p-Nitrobenzyl-3-(diphenylphosphoryloxy)-6-(1-p-nitrobenzyloxycarbonyloxyethyl)-1-azabicyclo[3.2.0]-hept-2-en-7-one-2-carboxylate (167 mg) was dissolved in 2.5 ml of dry acetonitrile, and 54 mg of diisopropylethylamine and 85 mg of (2R,4S)-1-p-nitro-benzyloxycarbonyl-2-aminocarbonylmethyl-4-mercaptopyrrolidine were added thereto in a nitrogen stream under ice-cooling, followed by stirring for 15 minutes. The reaction mixture was diluted with ether-dichloromethane (4:1), washed successively with water, an aqueous potassium dihydrogen phosphate solution and water, dried over anhydrous magnesium sulfate and concentrated. The residue was purified by silica gel thin layer chromatography to obtain 60 mg of (5R,6S,8 R,2′R,4′S)-p-nitrobenzyl-3-[(1-p-nitro-benzyloxycarbonyl-2-aminocarbonylmethylpyrrolidin)-4-ylthio]-6-(1-p-nitrobenzyloxycarbonyloxyethyl)-1-azabicyclo-[3.2.0]-hept-2-en-7-one-2-carboxylate.

IR $_{max}{}^{Nujol}$ cm$^{-1}$: 1 1775, 1740, 1690, 1670 (sh), 1510, 1340.

NMR δ (DMSO-d$_6$) 1.34 (3H, d, J =6.2 Hz), 5.23 (2H, s), 5.30 (2H, s), 6.82 (1H, bs), 8.21 (6H, d, J =8.8 Hz).

(b) (5R,6S,8R,2′R,4′S)-p-Nitrobenzyl-3-[(1-p-nitrobenzyloxycarbonyl-2-aminocarbonylmethylpyrrolidin)-4-ylthio]-6-(1-p-nitrobenzyloxycarbonyloxyethyl)-1-azabicyclo[3.2.0]-hept-2-en-7-one-2-carboxylate (60 mg) was dissolved in 1.3 ml of tetrahydrofuran and 0.5 ml of dimethylformamide, and a morpholinopropanesulfonic acid buffer solution (pH 7.0) (1.2 ml) and 10% palladium-carbon as prepared in Example 1 b) (73 mg) were added thereto. The resultant mixture was hydrogenated under atmospheric pressure of hydrogen at room temperature for 4 hours. The catalyst was removed by filtration, and the filtrate was distilled under reduced pressure to remove tetrahydrofuran. The residual solution was washed with dichloromethane, and the aqueous layer was again distilled under reduced pressure to remove the organic solvent. The residual solution was subjected to polymer chromatography (CHP-20P) to obtain (5R,6S,8R,2′R,4′S)-3-[(2-aminocarbonylmethylpyrrolidin)-4-ylthio]6-(1-hydroxyethyl)-1-azabicyclo[3.2.0]-hept-2-en-one-2-carboxylic acid from the fraction eluted with 1% tetrahydrofuran-water.

UV $_{max}^{H_2O}$ nm: 298.

IR $_{max}^{KBr}$ cm$^{-1}$: 1 1743, 1670, 1590, 1400, 1260.

NMR δ (D$_2$O) 1.27 (3H, d, J =6.3 Hz).

EXAMPLE 8

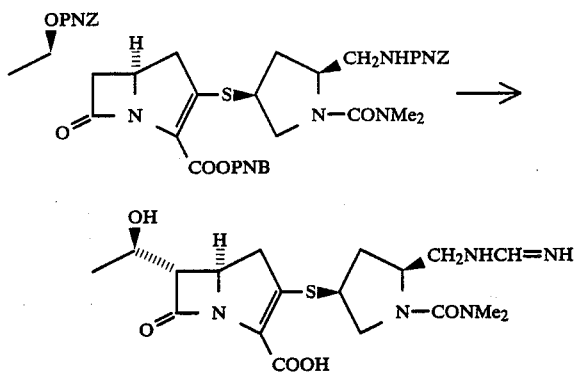

(5R,6S,8R,2'S,4'S)-p-Nitrobenzyl-3-[(1-dimethylaminocarbonyl-2-p-nitrobenzyloxycarbonylaminomethylpyrrolidin)-4-ylthio]-6-(1-p-nitrobenzyloxycarbonyloxy-ethyl)-1-azabicyclo[3.2.0]-hept-2-en-7-one-2-carboxylate (100 mg) was dissolved in 10 ml of tetrahydrofuran, and 8.5 ml of a morpholinopropanesulfonic acid buffer solution (pH 7.0) and 10% palladium-carbon as prepared in Example 1 b) (121 mg) were added thereto. The resultant mixture was hydrogenated under atmospheric pressure of hydrogen at room temperature for 4 hours. The catalyst was removed by filtration, and the filtrate was cooled at 0° C. and adjusted with 1N sodium hydroxide to pH 8.5, and then 200 mg of benzylform imidate hydrochloride was added thereto, followed by stirring for 10 minutes. Tetrahydrofuran in the reaction mixture was removed under reduced pressure The residual solution was washed with dichloromethane, and the aqueous layer was again distilled under reduced pressure to remove the organic solvent. The residual solution was subjected to polymer chromatography (CHP-20P) to obtain (5R,6S,2'S,4'S)-3-[(1-methylpyrrolidin)-4-ylthio]-6-(1-hydroxyethyl)-1-azabicyclo[3.2.0]-hept-2-en-7-one-2-carboxylic acid from the fraction eluted with 1% terrahydrofuran-water.

UV $_{max}^{H_2O}$ nm: 298.

IR $_{max}^{KBr}$ cm$^{-1}$: 1752, 1580, 1494, 1383, 1240.

NMR δ (D$_2$O) 1.25 (3H, d, J =6.3 Hz), 2.85 (6H, s), 7.78 (1H, s).

EXAMPLE 9

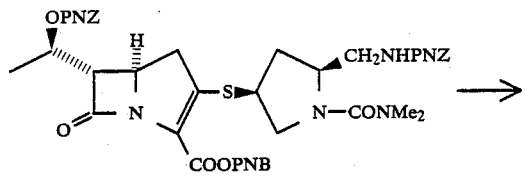

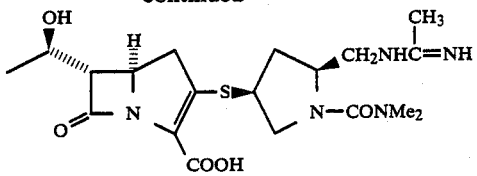

(5R,6S,8R,2's,4'S)-p-Nitrobenzyl-3-[(1-dimethylaminocarbonyl-2-p-nitrobenzyloxycarbonylaminomethylpyrrolidin)-4-ylthio]-6-(1-p-nitrobenzyloxycarbonyloxyethyl)-1-axabicyclo[3.2.0]-hept-2-en-7-one-2-carboxylate (100 mg) was dissolved in 10 ml of tetrahydrofuran, and 8.5 ml of a morpholinopropanesulfonic acid buffer solution (pH 7.0) and 10% palladium-carbon as prepared in Example 1 b) (121 mg) were added thereto, and the mixture was hydrogenated under atmospheric pressure of hydrogen at room temperature for 4 hours. The catalyst was removed by filtration, and the filtrate was cooled at 0° C. and adjusted with 1N sodium hydroxide solution of pH 8.5. Ethylacetoimidate hydrochloride (250 mg) was added thereto, followed by stirring for 1 hour. Tetrahydrofuran in the reaction mixture was removed under reduced pressure. The residual solution was washed with dichloromethane, and the aqueous layer was again distilled under reduced pressure to remove the organic solvent. The residual solution was subjected to polymer chromatography (CHP-20P) to obtain (5R,6S,8R,2,S,4,S)-3-[(1-dimethylaminocarbonyl-2-acetoamidinomethylpyrrolidin)-4-ylthio]-6-(1-hydroxyethyl)-1-azabicyclo[3.2.0]-hept-2-en-7-one-2-carboxylic acid from the fraction eluted with 1% tetrahydrofuran-water.

UV $_{max}^{H_2O}$ nm: 299.

IR $_{max}^{KBr}$ cm$^{-1}$: 1756, 1590, 1500, 1395.

NMR δ (D$_2$O): 1.26 (3H, d, J =6.3 Hz), 2.20 (3H, s), 2.84 (3H, s), 2.85 (3H, s).

EXAMPLE 10

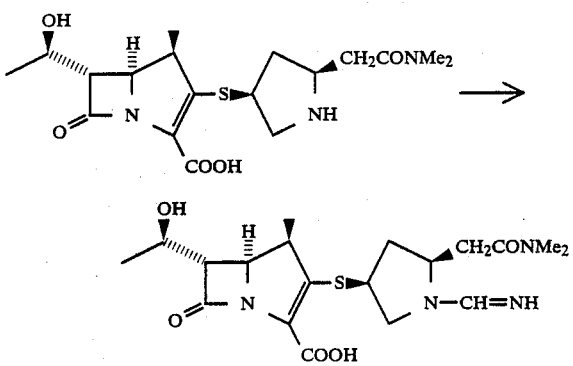

(4R,5S,6S,8R,2,P,4,S)-3-[(2-Dimethylaminocarbonylmethylpyrrolidin)-4ylthio]-4-methyl-6-(1-hydroxyethyl)-1-azabicyclo[3.2.0]-hept-2-en-7-one-2carboxylic acid. (15 mg) was dissolved in 15 ml of a morpholinopropane acid buffer solution (pH 7.0). The mixture was cooled at 0° C. and adjusting with 4N sodium hydroxide solution to pH 9.0, and 100 mg of benzyl formimidate hydrochloride was added thereto. The resulting mixture was kept at pH 9.0 with 4N sodium hydroxide solution, followed by stirring for 1 minutes. The reaction solution was neutralized with 1N hydrochloric acid, washed with dichloromethane and distilled under reduced pressure to remove dichloromethane. The residual solution was subjected to polymer chromatography (CHP-20P) to obtain (4R,5S,6S,8R,2,R,4,S)-3-[(1--formimino-2-dimethylaminocarbonylmethylpyrrolidin)-4-ylthio]-4-methyl-6-(1-hydroxyethyl)-1-azabicyclo[3.2.0]-hept-2-en-7-one-2-carboxylic acid from the fraction eluted with 1% tetrahydrofuran-water.

UV $_{max}^{H_2O}$ nm: 298.

IR $_{max}^{KBr}$ cm$^{-1}$: 1745, 1700, 1625, 1590, 1385.

NMR δ (D$_2$O): 1.21 (3H, d, J = 7.3 Hz), 1.28 (3H, J = 6.6 Hz), 2.93 (3H, s), 3.06 (3H, s), 7.99 (1H, s).

EXAMPLE 11

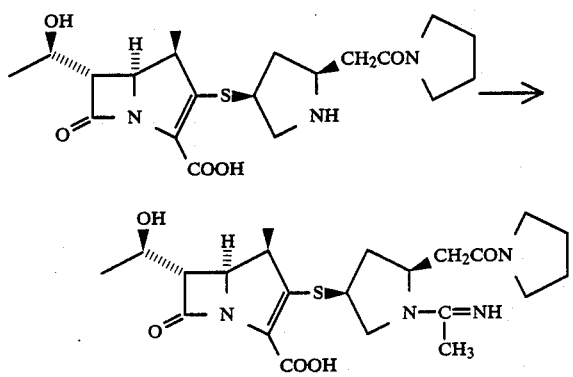

(4R,5S,6S,8R,2,R,4,S)-3-[[2-(1-Pyrrolidinecarbonylmethyl)pyrrolidin]-4ylthio]-4-methyl-6-(1-hydroxyethyl)-1-azabicyclo[3.2.0]-hept-2-en-7-one-2carboxylic acid (10 mg) was dissolved in a morpholinopropanesulfonic acid buffer solution. The mixture was cooled at 0° C. and adjusted with 4N sodium hydroxide solution to pH 9.0, and 100 mg of ethyl acetoimidate hydrochloride was added in four portions thereto. The resultant mixture was adjusted with 4N sodium hydroxide solution to pH 9.0, followed by stirring for 2 hours. The reaction solution was subjected to polymer chromatography (CHP-20P) to obtain (4R,5S,6S,8R,2'R,4'S)-3-[(1-acetoimino-2-(1-pyrrolidinecarbonylmethyl)pyrrolidin]-4-ylthio]-4-methyl-6-(1-hydroxyethyl)-1-azabicyclo[3.2.0]-hept-2-en-7-one-2-carboxylic acid from the fraction eluted with a 1% tetrahydrofuran-water.

UV $_{max}^{H_2O}$ nm: 298.

IR $_{max}^{KBr}$ cm$^{-1}$: 1750, 1685 (sh), 1610, 1450, 1380, 1255.

NMR δ (D$_2$O): 1.19 (3H, d, J = 7.3 Hz), 1.28 (3H, d, J = 6.6 Hz), 2.20 (3H, s).

According to the procedures as described in the preceding Examples, the compounds as shown in Tables 12, 13 and 14 were obtained.

TABLE 12

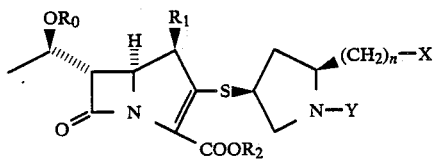

| Example No. | $R_0$ | $R_1$ | $R_2$ | X | Y | n | Physical data | |
|---|---|---|---|---|---|---|---|---|
| 12 | H | Me | PNB | CONH$_2$ | PNZ | 1 | IR$_{max}^{CHCl_3}$ cm$^{-1}$: | 1770, 1690, 1520, 1400, 1345, 1105 |
| | | | | | | | NMR δ (CDCl$_3$): | 1.28(3H, d, J = 6.8Hz), 1.36(3H, d, J=7Hz), 5.22 (2H, s), 5.49 1H, d, J=13.9Hz), 8.21(4H, d, J=8.8Hz) |
| | H | Me | H | CONH$_2$ | H | 1 | UV$_{max}^{H_2O}$ nm: | 298 |
| | | | | | | | IR$_{max}^{KBr}$ cm$^{-1}$: | 1750, 1665, 1590, 1487, 1280 |
| | | | | | | | NMR δ (D$_2$O): | 1.20(3H, d, J=7.3Hz), 1.28(3H, d, J = 6.3Hz), 3.44(1H, dd, J= 2.6Hz and 6.3Hz) |
| 13 | PNZ | H | PNB | CON⟨⟩ | PNZ | 1 | IR$_{max}^{CHCl_3}$ cm$^{-1}$: | 1773, 1740, 1695, 1620, 1513, 1340, 1254 |
| | | | | | | | NMR δ (CDCl$_3$): | 1.48(3H, d, J=6.2Hz), 5.22(2H, s), 5.26(2H, s), 5.46(1H, d, J = 13.9Hz), 8.21(6H, d, J=8.6Hz) |
| | H | H | H | CON⟨⟩ | H | 1 | UV$_{max}^{H_2O}$ nm: | 298 |
| | | | | | | | IR$_{max}^{KBR}$ cm$^{-1}$: | 1753, 1620, 1446, 1380 |
| | | | | | | | NMR δ (D$_2$O): | 1.26(3H, d, J=6.3Hz) |
| 14 | H | Me | PNB | CON⟨⟩ | PNZ | 1 | IR$_{max}^{neat}$ cm$^{-1}$: | 1765, 1700, 1620, 1520, 1347, 1210 |
| | | | | | | | NMR δ (CDCl$_3$): | 1.27(3H, d, J=7.3Hz), 1.34(3H, d, J=6.4Hz), 5.22(2H, s), 5.48(1H, d, J = 13.9Hz), 8.40(4H, d, J=8.6Hz) |

TABLE 12-continued

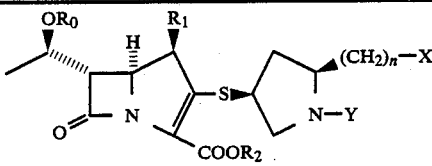

| Example No. | $R_0$ | $R_1$ | $R_2$ | X | Y | n | Physical data | |
|---|---|---|---|---|---|---|---|---|
| | | H | Me | H | CON⟨pyrrolidine⟩ | H | 1 | $UV_{max}^{H_2O}$ nm: | 296 |
| | | | | | | | | $IR_{max}^{KBr}$ cm$^{-1}$: | 1745, 1615, 1445, 1380 |
| | | | | | | | | NMR δ (D$_2$O): | 1.20(3H, d, J=7.32Hz), 1.27(3H, d, J=6.3Hz) |
| 15 | H | Me | PNB | COOMe | PNZ | 1 | $IR_{max}^{neat}$ cm$^{-1}$: | 1760, 1730(sh), 1700, 1515, 1345, 1210 |
| | | | | | | | NMR δ (CDCl$_3$): | 1.26(3H, d, J=7Hz), 1.34(3H, d, J=6.9Hz), 3.67(3H, s), 5.22 (2H, s), 5.49(1H, d, J=13.6Hz), 8.20(4H, d, J=8.8Hz) |
| | H | Me | H | COOMe | H | 1 | $UV_{max}^{H_2O}$ nm: | 296 |
| | | | | | | | $IR_{max}^{KBr}$ cm$^{-1}$: | 1755(sh), 1735, 1600, 1385, 1260 |
| | | | | | | | NMR δ (D$_2$O): | 1.20(3H, d, J = 7Hz), 1.27(3H, d, J= 6Hz), 3.44(1H, dd, J = 2.3Hz and 6 Hz), 3.73(3H, s), 4.19(1H, d, J=2.3Hz) |
| 16 | PNZ | H | PNB | NHCONH$_2$ | PNZ | 1 | $IR_{max}^{Nujol}$ cm$^{-1}$: | 1782, 1750, 1700, 1608, 1520, 1350 |
| | | | | | | | NMR δ (DMSO-d$_6$): | 5.35(2H, s), 5.42(2H, s), 8.33(6H, d, J=8.6Hz) |
| | H | H | H | NHCONH$_2$ | H | 1 | $UV_{max}^{H_2O}$ nm: | 298 |
| | | | | | | | $IR_{max}^{KBr}$ cm$^{-1}$: | 1750, 1652, 1585, 1383 |
| | | | | | | | NMR δ (D$_2$O): | 1.27(3H, d, J=6.3Hz), 3.18(2H, d, J = 9.2Hz) |
| 17 | PNZ | H | PNB | NHCONMe$_2$ | PNZ | 1 | $IR_{max}^{near}$ cm$^{-1}$: | 1780, 1742, 1692, 1636, 1520, 1255 |
| | | | | | | | NMR δ (CDCl$_3$): | 1.50(3H, d, J=6.4Hz), 2.87(6H, s), 5.26(4H, s), 8.20(6H, d J=8.6Hz) |
| | H | H | H | NHCONMe$_2$ | H | 1 | $UV_{max}^{H_2O}$ | 298 |
| | | | | | | | $IR_{max}^{KBr}$ cm$^{-1}$: | 1757, 1605(sh), 1595, 1535, 1395 |
| | | | | | | | NMR δ (D$_2$O): | 1.26(3H, d, J=6.4Hz), 2.88(6H, s), 3.67(2H, d, J=9.2Hz) |
| 18 | PNZ | H | PNB | NHCOOEt | PNZ | 1 | $IR_{max}^{near}$ cm$^{-1}$: | 1770, 1750, 1710, 1520, 1350, 1280 |
| | | | | | | | NMR δ (CDCl$_3$): | 1.22(3H, t, J=7Hz), 1.48(3H, d, J=6.2Hz), 5.24(4H, s), 8.20 (6H, d, J=8.6Hz) |
| | H | H | H | NHCOOEt | H | 1 | $UV_{max}^{H_2O}$ nm: | 298 |
| | | | | | | | $IR_{max}^{KBr}$ cm$^{-1}$: | 1746, 1700, 1585, 1380, 1245 |
| | | | | | | | NMR δ (D$_2$O): | 3.17(2H, d, J=8.9Hz), 3.30(1H, dd, J=4.6Hz and 12.5Hz), 3.40 (1H, dd, J=2.6Hz, and 5.9Hz) |
| 19 | PNZ | H | PNB | NHCOCH$_3$ | PNZ | 1 | $IR_{max}^{neat}$ cm$^{-1}$: | 1780, 1745, 1695, 1520, 1347, 1256 |
| | | | | | | | NMR δ (CDCl$_3$): | 1.48(3H, d, J=6.2Hz), 1.95(3H, s), 5.25(4H, s) |
| | H | H | H | NHCOCH$_3$ | H | 1 | $UV_{max}^{H_2O}$ nm: | 298 |
| | | | | | | | $IR_{max}^{KBr}$ cm$^{-1}$: | 1750, 1650, 1593, 1385, 1195, 1040 |
| | | | | | | | NMR δ (D$_2$O): | 1.28(3H, d, J=6Hz), 2.03(3H, s), 3.19(2H, d, J=9.2Hz) |
| 20 | PNZ | H | PNB | OCONH$_2$ | PNZ | 1 | $IR_{max}^{neat}$ cm$^{-1}$: | 1783, 1740, 1705, 1525, 1348, 1260 |
| | | | | | | | NMR δ (CDCl$_3$): | 1.48(3H, d, J=6.2Hz), 5.22(4H, s), 5.46(1H, d, J=13.9Hz) |
| | H | H | H | OCONH$_2$ | H | 1 | $UV_{max}^{H_2O}$ nm: | 298 |
| | | | | | | | $IR_{max}^{KBr}$ cm$^{-1}$: | 1725, 1595, 1395, 1520, 1092 |
| | | | | | | | NMR δ (D$_2$O): | 1.26(3H, d, J=6.3Hz), 3.40(1H, dd, J=2.6Hz and 5.9Hz), 3.57(1H, dd, J=6.9Hz, and 12.2Hz) |
| 21 | PNZ | H | PNZ | OCONMe$_2$ | PNZ | 1 | $IR_{max}^{neat}$ cm$^{-1}$: | 1773, 1740, 1700, 1515, 1340, 1253 |
| | | | | | | | NMR δ (CDCl$_3$): | 1.49(3H, d, J=6.4Hz), 2.88 (6H, s), 5.23(4H, s), 5.46 (1H, d, J=13.6Hz), 8.20(6H, d, J=8.4Hz) |
| | H | H | H | OCONMe$_2$ | H | 1 | $UV_{max}^{H_2O}$ nm: | 298 |
| | | | | | | | $IR_{max}^{KBr}$ cm$^{-1}$: | 1755, 1690, 1592, 1385, 1193 |
| | | | | | | | NMR δ (D$_2$O): | 1.27(3H, d, J=6.3Hz), 2.89(3H, s), 2.94(3H, s), 3.40(1H, dd, |

TABLE 12-continued

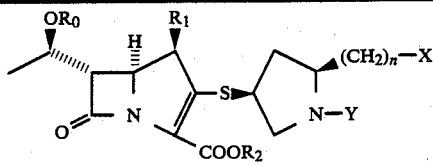

| Example No. | R₀ | R₁ | R₂ | X | Y | n | Physical data | |
|---|---|---|---|---|---|---|---|---|
| 22 | PNZ | H | PNB | NHPNZ | CONMe₂ | 1 | $IR_{max}^{CHCl_3}$ cm⁻¹: | J=2.6Hz and 5.9Hz), 3.56(1H, dd, J=6.9Hz and 12.2Hz) 1780, 1740(sh), 1720, 1625(sh), 1610, 1514 |
| | | | | | | | NMR δ (CDCl₃): | 1.49(3H, d, J=6.4Hz), 2.83 (6H, s), 5.18(2H, s), 5.26 (2H, s) |
| 23 | PNZ | H | PNB | OCONHMe | PNZ | 1 | $IR_{max}^{neat}$ cm⁻¹: | 1773, 1745(sh), 1702, 1520, 1343, 1260 |
| | | | | | | | NMR δ (CDCl₃): | 1.48(3H, d, J=6.4Hz), 2.95(3H, s), 5.25(4H, s), |
| | H | H | H | OCONHMe | H | 1 | $UV_{max}^{H_2O}$ nm: | 296 |
| | | | | | | | $IR_{max}^{KBr}$ cm⁻¹: | 1758, 1712, 1588, 1385, 1255, 1140 |
| | | | | | | | NMR δ (D₂O): | 1.27(3H, d, J=6.6Hz), 2.71(3H, s), 3.41(1H, dd, J=2.6Hz and 5.9Hz), |
| 24 | PNZ | H | PNB | OCOOEt | PNZ | 1 | $IR_{max}^{neat}$ cm⁻¹: | 1770, 1740, 1708, 1515, 1340 |
| | | | | | | | NMR δ (CDCl₃): | 1.31(3H, t, J=7Hz), 1.49(3H, d, J=6.2Hz), 4.19(2H, q, J=7Hz), 5.24(4H, s), 5.47(1H, d, J= 14.1Hz), 8.20(6H, d, J=8.6Hz) |
| | H | H | H | OCOOEt | H | 1 | $UV_{max}^{H_2O}$ nm: | 298 |
| | | | | | | | $IR_{max}^{KBr}$ cm⁻¹: | 1747, 1600, 1386, 1260 |
| | | | | | | | NMR δ (D₂O): | 1.26(3H, d, J=6.6Hz), 1.28(3H, t, J=6.9Hz), 3.30(1H, d, J=5.6Hz and 12.2Hz), 3.40(1H, dd J=2.6Hz and 5.9Hz) |
| 25 | PNZ | H | PNB | OCOCH₃ | PNZ | 1 | $IR_{max}^{neat}$ cm⁻¹: | 1772, 1730, 1698, 1517, 1342, 1225 |
| | | | | | | | NMR δ (CDCl₃): | 1.49(3H, d, J=6.4Hz), 2.06(3H, s), 5.24(4H, s), 5.47(1H, d, J= 13.6Hz), 8.20(6H, d, J=8.4Hz) |
| | H | H | H | OCOCH₃ | H | 1 | $UV_{max}^{H_2O}$ nm: | 298 |
| | | | | | | | $IR_{max}^{KBr}$ cm⁻¹: | 1740, 1590, 1385, 1238 |
| | | | | | | | NMR δ (D₂O): | 1.26(3H, d, J=6.3Hz), 2.14(3H, s) |
| 26 | PNZ | H | PNB | CONH₂ | PNZ | 2 | $IR_{max}^{Nujol}$ cm⁻¹: | 1790, 1746, 1708, 1660, 1600, 1510 |
| | | | | | | | NMR δ (CDCl₃): | 1.34(3H, d, J=6.1Hz), 5.22(2H, s), 5.30(2H, s), 8.21(6H, d, J= 8.6Hz) |
| | H | H | H | CONH₂ | H | 2 | $UV_{max}^{H_2O}$ nm: | 298 |
| | | | | | | | $IR_{max}^{KBr}$ cm⁻¹: | 1750, 1660, 1585, 1387 |
| | | | | | | | NMR δ (D₂O): | 1.25(3H, d, J=6.6Hz), 2.39(2H, t, J=7.7Hz), 3.27(1H, dd, J=5.2Hz and 12.5Hz), 3.38(1H, dd, J=2.6Hz and 5.9Hz) |
| 27 | H | Me | PNB | CONH₂ | PNZ | 2 | $IR_{max}^{CHCl_3}$ cm⁻¹: | 1700, 1770, 1520, 1347, 1102 |
| | | | | | | | NMR δ (acetone-d₆): | 1.27(6H, d, J=6.2Hz), 5.25 (2H, s), 5.51(1H, d, J= 14.1Hz) |
| | H | Me | H | CONH₂ | H | 2 | $UV_{max}^{H_2O}$ nm: | 298 |
| | | | | | | | $IR_{max}^{KBr}$ cm⁻¹: | 1750, 1663, 1590, 1383, 1246 |
| | | | | | | | NMR δ (D₂O): | 1.18(3H, d, J=7.3Hz) 1.26(3H, d, J=6.6Hz), 3.43(1H, dd, J=2.6Hz and 6.3Hz) |
| 28 | PNZ | H | PNB | CON(H)(Me) | PNZ | 2 | $IR_{max}^{Nujol}$ cm⁻¹: | 1788, 1742, 1704, 1633, 1512 |
| | | | | | | | NMR δ (DMSO-d₆): | 3.22(3H, s), 5.22(2H, s), 5.30 (2H, s), 8.21(6H, d, J=8.6Hz) |
| | H | H | H | CON(H)(Me) | H | 2 | $UV_{max}^{H_2O}$ nm: | 299 |
| | | | | | | | $IR_{max}^{KBr}$ cm⁻¹: | 1757, 1638, 1590, 1380, 1240 |
| | | | | | | | NMR δ (D₂O): | 1.25(3H, d, J=6.3Hz), 2.69(3H, s), 3.38(1H, dd, J=2.6Hz and 6.3Hz) |
| 29 | PNZ | H | PNB | CONMe₂ | PNZ | 2 | $IR_{max}^{CHCl_3}$ cm⁻¹: | 1782, 1750, 1700, 1638, 1523 |
| | | | | | | | NMR δ (CDCl₃): | 1.48(3H, d, J=6.4Hz), 2.91(3H, s), 2.94(3H, s), 5.26(2H, s), 5.21(2H, s), 5.48(1H, d, J= 13.9Hz), 8.20(6H, d, J=8.6Hz) |
| | H | H | H | CONMe₂ | H | 2 | $UV_{max}^{H_2O}$ nm: | 298 |

TABLE 12-continued

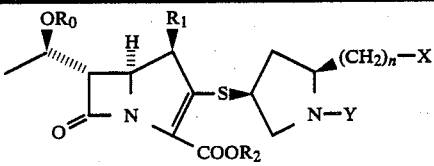

| Example No. | $R_0$ | $R_1$ | $R_2$ | X | Y | n | Physical data | |
|---|---|---|---|---|---|---|---|---|
| | | | | | | | $IR_{max}^{KBr}$ cm$^{-1}$: | 1756, 1620, 1590, 1385, 1245 |
| | | | | | | | NMR δ (D$_2$O): | 1.25(3H, d, J=6.3Hz) 2.90(3H, s), 3.03(3H, s) |
| 30 | PNZ | H | PNB | OH | PNZ | 1 | $IR_{max}^{neat}$ cm$^{-1}$: | 1778, 1748, 1700, 1515, 1305, 1259 |
| | | | | | | | NMR δ (CDCl$_3$): | 1.48(3H, d, J=6.4Hz), 5.23(4H, s), 5.46(1H, d, J=13.9Hz), 8.20 (6H, d, J=8.6Hz) |
| | H | H | H | OH | H | 1 | $UV_{max}^{H_2O}$ nm: | 298 |
| | | | | | | | $IR_{max}^{KBr}$ cm$^{-1}$: | 1750, 1585, 1385, 1240 |
| | | | | | | | NMR δ (D$_2$O): | 1.26(3H, d, J=6.3Hz), 3.18(2H, d, J=8.9Hz) |
| 31 | H | Me | H | OH | CH=NH | 1 | $UV_{max}^{H_2O}$ nm: | 298 |
| | | | | | | | $IR_{max}^{KBr}$ cm$^{-1}$: | 1742, 1698, 1582, 1380 |
| | | | | | | | NMR δ (D$_2$O): | 1.19(3H, d, J=7.3Hz), 1.27(3H, d, J=6.3Hz), 8.05(1H, s) |
| 32 | H | Me | H | OH | CH$_3$<br>\|<br>C=NH | 1 | $UV_{max}^{H_2O}$ nm: | 298 |
| | | | | | | | $IR_{max}^{KBr}$ cm$^{-1}$: | 1740, 1693, 1605, 1382 |
| | | | | | | | NMR δ (D$_2$O): | 1.19(3H, d, J=6.9Hz), 1.27(3H, d. J=6.3Hz), 2.20(3H, s) |
| 33 | PNZ | H | PNB | SMe | PNZ | 1 | $IR_{max}^{neat}$ cm$^{-1}$: | 1778, 1738, 1705, 1520, 1345, 1260 |
| | | | | | | | NMR δ (CDCl$_3$): | 1.49(3H, d, J=6.4Hz), 2.09(3H, s), 5.23(2H, s), 5.25(2H, s), 5.47(1H, d, J=13.6Hz), 8.20(6H, d, J=8.6Hz) |
| | H | H | H | SMe | H | 1 | $UV_{max}^{H_2O}$ nm: | 297 |
| | | | | | | | $IR_{max}^{KBr}$ cm$^{-1}$: | 1755, 1590, 1380, 1238 |
| | | | | | | | NMR δ (D$_2$O): | 1.26(3H, d, J=6.3Hz), 2.14(3H, s), 3.17(2H, d, J=8.9Hz) |
| 34 | PNZ | H | PNB | SO$_2$Me | PNZ | 1 | $IR_{max}^{neat}$ cm$^{-1}$: | 1780, 1750, 1703, 1520, 1308, 1263 |
| | | | | | | | NMR δ (CDCl$_3$): | 1.49(3H, d, J=6.4Hz), 2.75(3/2H, s), 2.80(3/2H, s), 5.23(2H, s), 5.25(2H, s), 5.47(1H, d, J=13.9Hz), 8.20(6H, d, J=8.8Hz) |
| | H | H | H | SO$_2$Me | H | 1 | $UV_{max}^{H_2O}$ nm: | 298 |
| | | | | | | | $IR_{max}^{KBr}$ cm$^{-1}$: | 1755, 1590, 1390, 1292, 1128 |
| | | | | | | | NMR δ (D$_2$O): | 1.26(3H, d, J=6.3Hz), 3.15(3H, s), 3.39(1H, dd, J=2.3Hz and 5.9Hz) |
| 35 | PNZ | H | PNB | OMe | PNZ | 1 | $IR_{max}^{neat}$ cm$^{-1}$: | 1783, 1752, 1708, 1528, 1350 |
| | | | | | | | NMR δ (CDCl$_3$): | 1.49(3H, d, J=6.4Hz), 3.33(3H, s), 5.23(2H, s), 5.25(2H, s), 5.47(1H, d, J=13.9Hz), 8.20(6H, d, J=8.6Hz) |
| | H | H | H | OMe | H | 1 | $UV_{max}^{H_2O}$ nm: | 298 |
| | | | | | | | $IR_{max}^{KBr}$ cm$^{-1}$: | 1752, 1590, 1382, 1242 |
| | | | | | | | NMR δ (D$_2$O): | 1.26(3H, d, J=6.6Hz), 3.40(3H, s) |
| 36 | H | Me | PNB | CN | PNZ | 1 | $IR_{max}^{neat}$ cm$^{-1}$: | 2250, 1770, 1705, 1513, 1350 |
| | | | | | | | NMR δ (CDCl$_3$): | 1.28(3H, d, J=7Hz), 1.35(3H, d, J=6Hz), 5.23(2H, s), 5.48(1H, d, J=13.9Hz), 8.21(4H, d, J=8.1Hz) |
| | H | Me | H | CN | H | 1 | $UV_{max}^{H_2O}$ nm: | 300 |
| | | | | | | | $IR_{max}^{KBr}$ cm$^{-1}$: | 2250, 1750, 1593, 1390 |
| | | | | | | | NMR δ (D$_2$O): | 1.21(3H, d, J=7.3Hz), 1.29(3H, d, J=6.3Hz), 3.16(1H, dd, J=4.3Hz and 12.2Hz) |
| 37 | PNZ | H | PNB | CN | PNZ | 1 | $IR_{max}^{neat}$ cm$^{-1}$: | 2245, 1778, 1745, 1700, 1519 |
| | | | | | | | NMR (CDCl$_3$): | 1.48(3H, d, J=6.2Hz), 5.24(4H, s), 8.18(6H, d, J=8.8Hz) |
| | H | H | H | CN | H | 1 | $UV_{max}^{H_2O}$ nm: | 298 |
| | | | | | | | $IR_{max}^{KBr}$ cm$^{-1}$: | 1750, 1585, 1383 |
| | | | | | | | NMR δ (D$_2$O): | 1.28(3H, d, J=6.6Hz), 3.72(1H, dd, J=7.6Hz and 12.5Hz) |
| 38 | H | Me | PNB | OMe | PNZ | 1 | $IR_{max}^{neat}$ cm$^{-1}$: | 1765, 1700, 1520, 1340 |
| | | | | | | | NMR δ (CDCl$_3$): | 1.27(3H, d, J=6.6Hz), 1.48(3H, d, J=6.2Hz), 3.33(3H, s), 5.22(2H, s), 5.48(1H, d, J=13.6Hz), 8.20(4H, d, J=8.4Hz) |
| | H | Me | H | OMe | H | 1 | $UV_{max}^{H_2O}$ nm: | 298 |
| | | | | | | | $IR_{max}^{KBr}$ cm$^{-1}$: | 1753, 1597, 1385 |

TABLE 12-continued

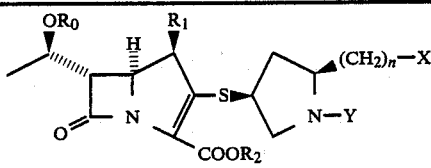

| Example No. | R₀ | R₁ | R₂ | X | Y | n | Physical data | |
|---|---|---|---|---|---|---|---|---|
| | | | | | | | NMR δ (D₂O): | 1.19(3H, d, J=7.3Hz), 1.26(3H, d, J=6.3Hz), 3.39(3H, s), 3.44(1H, dd, J=2.4Hz and 6.3Hz) |
| 39 | H | Me | PNB | CON(H)(Me) | PNZ | 3 | IR$_{max}^{neat}$ cm⁻¹:<br>NMR δ (CDCl₃): | 1775, 1705, 1658, 1525, 1348<br>1.26(3H, d, J=7Hz), 1.34(3H, d, J=6.4Hz), 2.77(3H, d, J=4.8Hz), 5.20(2H, s), 5.47(1H, d, J=13.6Hz) |
| | H | Me | H | CON(H)(Me) | H | 3 | UV$_{max}^{H_2O}$ nm<br>IR$_{max}^{KBr}$ cm⁻¹:<br>NMR δ (D₂O): | 298<br>1752, 1640, 1590, 1383<br>1.20(3H, d, J=7.3Hz), 1.27(3H, d, J=6.3Hz), 2.29(2H, t, J=7Hz), 2.71(3H, s) |
| 40 | H | Me | PNB | CON(H)(Me) | PNZ | 4 | IR$_{max}^{neat}$ cm⁻¹:<br>NMR δ (CDCl₃): | 1763, 1700, 1655, 1520, 1343<br>1.27(3H, d, J=7Hz), 1.35(3H, d, J=7Hz), 2.78(3H, d, J=4.8Hz), 5.21(2H, s), 8.21(4H, d, J=8.8Hz) |
| | H | Me | H | CON(H)(Me) | H | 4 | UV$_{max}^{H_2O}$ nm:<br>IR$_{max}^{KBr}$ cm⁻¹:<br>NMR δ (D₂O): | 298<br>1752, 1640, 1590, 1385<br>1.22(3H, d, J=6.9Hz), 1.30(3H, d, J=6.3Hz), 2.27(2H, t, J=7Hz), 2.73(3H, s) |
| 41 | H | Me | PNB | COOPNB | PNZ | 1 | IR$_{max}^{neat}$ cm⁻¹:<br>NMR δ (CDCl₃): | 1762, 1736, 1703, 1519, 1342<br>1.26(3H, d, J=6.8Hz), 1.34(3H, d, J=6.2Hz), 5.20(4H, s), 8.19(6H, d, J=8.8Hz) |
| | H | Me | H | COOH | H | 1 | UV$_{max}^{H_2O}$ nm:<br>IR$_{max}^{KBr}$ cm⁻¹:<br>NMR δ (D₂O): | 298<br>1750, 1598, 1393, 1180<br>1.22(3H, d, J=7.3Hz), 1.30(3H, d, J=6.3Hz), 3.47(1H, dd, J=2.6Hz and 6.3Hz) |
| 42 | H | Me | PNB | COOPNB | PNZ | 2 | IR$_{max}^{neat}$ cm⁻¹:<br>NMR δ (CDCl₃): | 1770, 1730, 1693, 1604, 1515<br>1.26(3H, d, J=7.3Hz), 1.34(3H, d, J=6Hz), 5.20(4H, S), 8.18(6H, d, J=8.1Hz) |
| | H | Me | H | COOH | H | 2 | UV$_{max}^{H_2O}$ nm:<br>IR$_{max}^{KBr}$ cm⁻¹:<br>NMR δ (D₂O): | 298<br>1755, 1608, 1570, 1400<br>1.23(3H, d, J=7.3Hz), 1.30(3H, d, J=6.6Hz) |
| 43 | H | Me | PNB | CH=N—OMe | PNZ | 1 | IR$_{max}^{neat}$ cm⁻¹:<br>NMR δ (CDCl₃): | 1760, 1700, 1520, 1400, 1345<br>1.27(3H, d, J=6.8Hz), 1.35(3H, d, J=5.9Hz), 5.23(2H, s), 5.49(1H, d, J=13.9Hz), 8.20(4H, d, J=8.6Hz) |
| | H | Me | H | CH=N—OMe | H | 1 | UV$_{max}^{H_2O}$ nm:<br>IR$_{max}^{KBr}$ cm⁻¹:<br>NMR δ (D₂O): | 298<br>1750, 1595, 1390<br>1.22(3H, d, J=7.3Hz), 1.29(3H, d, J=6.3Hz), 3.47(1H, dd, J=2.6Hz and 5.9Hz), 3.85, 3.90 (3H, s) |
| 44 | H | Me | PNB | CH=N—NMe₂ | PNZ | 1 | IR$_{max}^{neat}$ cm⁻¹:<br>NMR δ (CDCl₃): | 1765, 1700, 1520, 1400, 1340<br>1.19(3H, d, J=7Hz), 1.27(3H, d, J=7Hz), 2.73(6H, s), 5.23(2H, s), 8.21(4H, d, J=8.8Hz) |
| | H | Me | H | CH=N—NMe₂ | H | 1 | UV$_{max}^{H_2O}$ nm:<br>IR$_{max}^{KBr}$ cm⁻¹:<br>NMR δ (D₂O): | 238, 298<br>1748, 1590, 1383<br>1.22(3H, d, J=7.3Hz), 1.30(3H, d, J=6.6Hz), 2.72(6H, s), 3.47 (1H, dd, J=2.6Hz and 6.3Hz), 6.02(1H, t, J=5Hz) |
| 45 | H | Me | PNB | CONHNMe₂ | PNZ | 1 | IR$_{max}^{neat}$ cm⁻¹:<br>NMR δ (CDCl₃): | 1763, 1700, 1520, 1400, 1342<br>1.28(3H, d, J=7Hz), 1.35(3H, d, J=6.4Hz), 2.49(3H, s), 2.56 (3H, s), 5.22(2H, s), 8.21(4H, d, J=8.4Hz) |

TABLE 12-continued

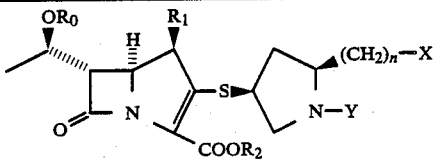

| Example No. | $R_0$ | $R_1$ | $R_2$ | X | Y | n | | Physical data |
|---|---|---|---|---|---|---|---|---|
| | H | Me | H | CONHNMe$_2$ | H | 1 | UV$_{max}^{H_2O}$ nm: | 296 |
| | | | | | | | IR$_{max}^{KBr}$ cm$^{-1}$: | 1745, 1658, 1590, 1383 |
| | | | | | | | NMR δ (D$_2$O): | 1.22(3H, d, J=7.3Hz), 1.30(3H, d, J=6.6Hz), 2.55(6H, s) |
| 46 | H | Me | PNB | OH | PNZ | 2 | IR$_{max}^{neat}$ cm$^{-1}$: | 1768, 1690, 1520, 1348, 1212 |
| | | | | | | | NMR δ (CDCl$_3$): | 1.28(3H, d, J=7.3Hz), 1.35 3H, d, J=6.3Hz), 5.23(2H, s), 5.50(1H, d, J=13.9Hz) |
| | H | Me | H | OH | H | 2 | UV$_{max}^{H_2O}$ nm: | 298 |
| | | | | | | | IR$_{max}^{KBr}$ cm$^{-1}$: | 1750, 1588, 1383 |
| | | | | | | | NMR δ (D$_2$O): | 1.23(3H, d, J=7.3Hz), 1.30(3H, d, J=6.3Hz), 3.47(1H, dd, J=2.6Hz and 6.3Hz) |
| 47 | H | Me | PNB | OH | PNZ | 3 | IR$_{max}^{neat}$ cm$^{-1}$: | 1770, 1690, 1520, 1348, 1208 |
| | | | | | | | NMR δ (CDCl$_3$): | 1.28(3H, d, J=7Hz), 1.36(3H, d, J=6.3Hz), 5.50(1H, d, J=13.5Hz), 7.65(2H, d, J=8.9Hz) |
| | H | Me | H | OH | H | 3 | UV$_{max}^{H_2O}$ nm: | 298 |
| | | | | | | | IR$_{max}^{KBr}$ cm$^{-1}$: | 1752, 1595, 1388 |
| | | | | | | | NMR δ (D$_2$O): | 1.22(3H, d, J=7.3Hz), 1.30(3H, d, J=6.3Hz) |

TABLE 13

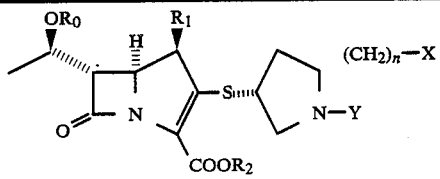

| Example No. | $R_0$ | $R_1$ | $R_2$ | X | Y | n | | Physical data |
|---|---|---|---|---|---|---|---|---|
| 48 | H | Me | PNB | OH | PNZ | 1 | IR$_{max}^{neat}$ cm$^{-1}$: | 1760, 1685, 1512, 1340 |
| | | | | | | | NMR δ (CDCl$_3$): | 1.27 (3H, d, J=7.3Hz), 1.34 (3H, d, J=6.3 Hz), 5.24 (2H, s), 5.48 (1H, d, J=13.9Hz), 7.52 (2H, d, J=8.9Hz), 7.63 (2H d, J=8.9 Hz) |
| | H | Me | H | OH | H | 1 | UV$_{max}^{H_2O}$ nm: | 298 |
| | | | | | | | IR$_{max}^{KBr}$ cm$^{-1}$: | 1752, 1598, 1395 |
| | | | | | | | NMR δ (D$_2$O): | 1.22 (3H, d, J=7.3Hz), 1.30 (3H, d, J=6.3 Hz) 3.48 (1H, dd, J=2.6 Hz and 5.9 Hz) |
| 49 | H | Me | PNB | CONH-Me | PNZ | 1 | IR$_{max}^{neat}$ cm$^{-1}$: | 1768, 1705, 1660, 1524 |
| | | | | | | | NMR δ (CDCl$_3$): | 1.27 (3H, d, J=7.3 Hz), 1.36 (3H, d, J=6.3 Hz), 2.72 (3H, d, J=4.6 Hz), 5.22 (2H, s), 5.50 (1H, d, J=13.5 Hz), 7.52 (2H, d, J=8.3 Hz), 7.66 (2H d, J=8.6 Hz) |
| | H | Me | H | CONH-Me | H | 1 | UV$_{max}^{H_2O}$ nm: | 298 |
| | | | | | | | IR$_{max}^{KBr}$ cm$^{-1}$: | 1745, 1642, 1580, 1380 |
| | | | | | | | NMR δ (D$_2$O): | 1.22 (3H, d, J=7.3 Hz), 1.31 (3H, d, J=6.3 Hz), 2.74 (3H, s) |

TABLE 14

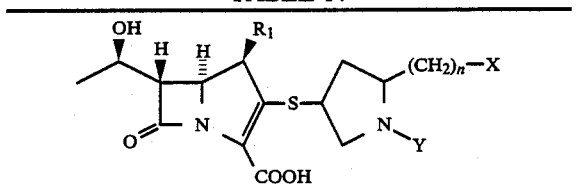

| No. | R₁ | n | X | Y |
|---|---|---|---|---|
| 1 | H | 1 | CONH₂ | H |
| 2 | Me | 1 | CONH₂ | H |
| 3 | H | 1 | CONHMe | H |
| 4 | Me | 1 | CONHMe | H |
| 5 | H | 1 | CONMe₂ | H |
| 6 | Me | 1 | CONMe₂ | H |
| 7 | H | 1 | CON(pyrrolidine) | H |
| 8 | Me | 1 | CON(pyrrolidine) | H |
| 9 | H | 1 | CON(azetidine) | H |
| 10 | Me | 1 | CON(azetidine) | H |
| 11 | H | 1 | CON(piperidine) | H |
| 12 | Me | 1 | CON(piperidine) | H |
| 13 | H | 1 | COOMe | H |
| 14 | Me | 1 | COOMe | H |
| 15 | H | 1 | COOEt | H |
| 16 | Me | 1 | COOEt | H |
| 17 | H | 1 | NHCONH₂ | H |
| 18 | Me | 1 | NHCONH₂ | H |
| 19 | H | 1 | NHCONHMe | H |
| 20 | Me | 1 | NHCONHMe | H |
| 21 | H | 1 | NHCONMe₂ | H |
| 22 | Me | 1 | NHCONMe₂ | H |
| 23 | H | 1 | NHAc | H |
| 24 | Me | 1 | NHAc | H |
| 25 | H | 1 | NHCOOMe | H |
| 26 | Me | 1 | NHCOOMe | H |
| 27 | H | 1 | NHCOOEt | H |
| 28 | Me | 1 | NHCOOEt | H |
| 29 | H | 1 | OAc | H |
| 30 | Me | 1 | OAc | H |
| 31 | H | 1 | OCONH₂ | H |
| 32 | Me | 1 | OCONH₂ | H |
| 33 | H | 1 | OCONHMe | H |
| 34 | Me | 1 | OCONHMe | H |
| 35 | H | 1 | OCONMe₂ | H |
| 36 | Me | 1 | OCONMe₂ | H |
| 37 | H | 1 | NH—CH=NH | CONMe₂ |
| 38 | Me | 1 | NHCH=NH | CONMe₂ |

TABLE 14-continued

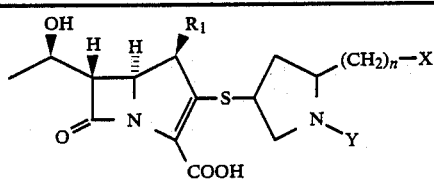

| No. | R₁ | n | X | Y |
|---|---|---|---|---|
| 39 | H | 1 | NH—C(Me)=NH | CONMe₂ |
| 40 | Me | 1 | NH—C(Me)=NH | CONMe₂ |
| 41 | H | 1 | CONH₂ | CH=NH |
| 42 | Me | 1 | CONH₂ | CH=NH |
| 43 | H | 1 | CONH₂ | C(Me)=NH |
| 44 | Me | 1 | CONH₂ | C(Me)=NH |
| 45 | H | 1 | CONHMe | CH=NH |
| 46 | Me | 1 | CONHMe | CH=NH |
| 47 | H | 1 | CONHMe | C(Me)=NH |
| 48 | Me | 1 | CONHMe | C(Me)=NH |
| 49 | H | 1 | CONMe₂ | CH=NH |
| 50 | Me | 1 | CONMe₂ | CH=NH |
| 51 | H | 1 | CONMe₂ | C(Me)=NH |
| 52 | Me | 1 | CONMe₂ | C(Me)=NH |
| 53 | H | 1 | CON(pyrrolidine) | CH=NH |
| 54 | Me | 1 | CON(pyrrolidine) | CH=NH |
| 55 | H | 1 | CON(pyrrolidine) | C(Me)=NH |
| 56 | Me | 1 | CON(pyrrolidine) | C(Me)=NH |
| 57 | H | 1 | NHCONMe₂ | CH=NH |
| 58 | Me | 1 | NHCONMe₂ | CH=NH |

TABLE 14-continued

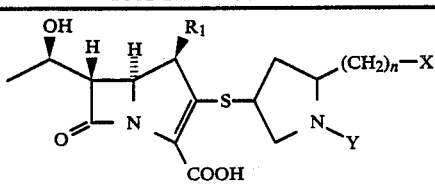

| No. | R₁ | n | X | Y |
|---|---|---|---|---|
| 59 | H | 1 | NHCONMe₂ | C=NH<br>\|<br>Me |
| 60 | Me | 1 | NHCONMe₂ | C=NH<br>\|<br>Me |
| 61 | H | 1 | CONHEt | H |
| 62 | Me | 1 | CONHEt | H |
| 63 | H | 1 | CONEt₂ | H |
| 64 | Me | 1 | CONEt₂ | H |
| 65 | H | 1 | NHCONHEt | H |
| 66 | Me | 1 | NHCONHEt | H |
| 67 | H | 1 | NHCONEt₂ | H |
| 68 | Me | 1 | NHCONEt₂ | H |
| 69 | H | 1 | OCONHEt | H |
| 70 | Me | 1 | OCONHEt | H |
| 71 | H | 1 | OCONEt₂ | H |
| 72 | Me | 1 | OCONEt₂ | H |
| 73 | H | 1 | OCOEt | H |
| 74 | Me | 1 | OCOEt | H |
| 75 | H | 1 | OCOOMe | H |
| 76 | Me | 1 | OCOOMe | H |
| 77 | H | 1 | OCOOEt | H |
| 78 | Me | 1 | OCOOEt | H |
| 79 | H | 1 | COOH | H |
| 80 | Me | 1 | COOH | H |
| 81 | H | 2 | CONH₂ | H |
| 82 | Me | 2 | CONH₂ | H |
| 83 | H | 2 | CONHMe | H |
| 84 | Me | 2 | CONHMe | H |
| 85 | H | 2 | CONMe₂ | H |
| 86 | Me | 2 | CONMe₂ | H |
| 87 | H | 2 | CON⟨azetidine⟩ | H |
| 88 | Me | 2 | CON⟨azetidine⟩ | H |
| 89 | H | 2 | CON⟨pyrrolidine⟩ | H |
| 90 | Me | 2 | CON⟨pyrrolidine⟩ | H |
| 91 | H | 2 | COOMe | H |
| 92 | Me | 2 | COOMe | H |
| 93 | H | 2 | COOH | H |
| 94 | Me | 2 | COOH | H |
| 95 | H | 2 | CONH₂ | CH=NH |
| 96 | Me | 2 | CONH₂ | CH=NH |
| 97 | H | 2 | CONH₂ | C=NH<br>\|<br>Me |
| 98 | Me | 2 | CONH₂ | C=NH<br>\|<br>Me |
| 99 | H | 2 | CONHMe | CH=NH |
| 100 | Me | 2 | CONHMe | CH=NH |
| 101 | H | 2 | CONHMe | C=NH<br>\|<br>Me |
| 102 | Me | 2 | CONHMe | C=NH<br>\|<br>Me |
| 103 | H | 2 | CONMe₂ | CH=NH |
| 104 | Me | 2 | CONMe₂ | CH=NH |
| 105 | H | 2 | CONMe₂ | C=NH<br>\|<br>Me |
| 106 | Me | 2 | CONMe₂ | C=NH<br>\|<br>Me |
| 107 | H | 3 | CONH₂ | H |
| 108 | Me | 3 | CONH₂ | H |
| 109 | H | 3 | CONHMe | H |
| 110 | Me | 3 | CONHMe | H |
| 111 | H | 3 | CONMe₂ | H |
| 112 | Me | 3 | CONMe₂ | H |
| 113 | H | 3 | CON⟨pyrrolidine⟩ | H |
| 114 | Me | 3 | CON⟨pyrrolidine⟩ | H |
| 115 | H | 3 | COOMe | H |
| 116 | Me | 3 | COOMe | H |
| 117 | H | 3 | COOH | H |
| 118 | Me | 3 | COOH | H |
| 119 | H | 3 | CONH₂ | CH=NH |
| 120 | Me | 3 | CONH₂ | CH=NH |
| 121 | H | 3 | CONH₂ | C=NH<br>\|<br>Me |
| 122 | Me | 3 | CONH₂ | C=NH<br>\|<br>Me |
| 123 | H | 3 | CONHMe | CH=NH |
| 124 | Me | 3 | CONHMe | CH=NH |
| 125 | H | 3 | CONHMe | C=NH<br>\|<br>Me |
| 126 | Me | 3 | CONHMe | C=NH<br>\|<br>Me |

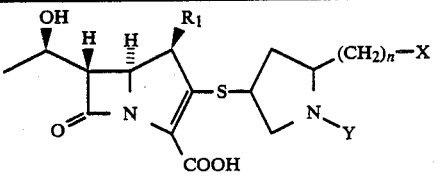

TABLE 14-continued

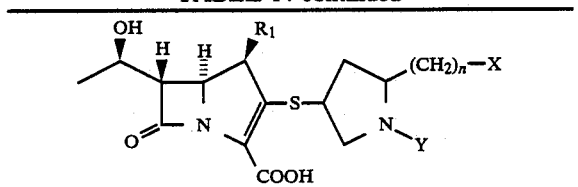

| No. | $R_1$ | n | X | Y |
|---|---|---|---|---|
| 127 | H | 3 | $CONMe_2$ | CH=NH |
| 128 | Me | 3 | $CONMe_2$ | CH=NH |
| 129 | H | 3 | $CONMe_2$ | C(Me)=NH |
| 130 | Me | 3 | $CONMe_2$ | C(Me)=NH |
| 131 | H | 4 | $CONH_2$ | H |
| 132 | Me | 4 | $CONH_2$ | H |
| 133 | H | 4 | CONHMe | H |
| 134 | Me | 4 | CONHMe | H |
| 135 | H | 4 | $CONMe_2$ | H |
| 136 | Me | 4 | $CONMe_2$ | H |
| 137 | H | 4 | COOMe | H |
| 138 | Me | 4 | COOMe | H |
| 139 | H | 4 | COOH | H |
| 140 | Me | 4 | COOH | H |
| 141 | H | 4 | CON(pyrrolidine) | H |
| 142 | Me | 4 | CON(pyrrolidine) | H |
| 143 | H | 4 | $CONH_2$ | CH=NH |
| 144 | Me | 4 | $CONH_2$ | CH=NH |
| 145 | H | 4 | $CONH_2$ | C(Me)=NH |
| 146 | Me | 4 | $CONH_2$ | C(Me)=NH |
| 147 | H | 4 | CONHMe | CH=NH |
| 148 | Me | 4 | CONHMe | CH=NH |
| 149 | H | 4 | CONHMe | C(Me)=NH |
| 150 | Me | 4 | CONHMe | C(Me)=NH |
| 151 | H | 4 | $CONMe_2$ | CH=NH |
| 152 | Me | 4 | $CONMe_2$ | CH=NH |
| 153 | H | 4 | $CONMe_2$ | C(Me)=NH |
| 154 | Me | 4 | $CONMe_2$ | C(Me)=NH |
| 155 | H | 1 | CN | H |
| 156 | Me | 1 | CN | H |

TABLE 14-continued

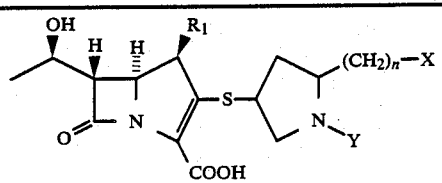

| No. | $R_1$ | n | X | Y |
|---|---|---|---|---|
| 157 | H | 1 | CH=N—OMe | H |
| 158 | Me | 1 | CH=N—OMe | H |
| 159 | H | 1 | CH=N—OEt | H |
| 160 | Me | 1 | CH=N—OEt | H |
| 161 | H | 1 | $CH=NNMe_2$ | H |
| 162 | Me | 1 | $CH=NNMe_2$ | H |
| 163 | H | 1 | $CH=NNEt_2$ | H |
| 164 | Me | 1 | $CH=NNEt_2$ | H |
| 165 | H | 1 | CH=NN(Me)(Et) | H |
| 166 | Me | 1 | CH=NN(Me)(Et) | H |
| 167 | H | 1 | CH=NNHMe | H |
| 168 | Me | 1 | CH=NNHMe | H |
| 169 | H | 1 | $CONHNH_2$ | H |
| 170 | Me | 1 | $CONHNH_2$ | H |
| 171 | H | 1 | $CONHNMe_2$ | H |
| 172 | Me | 1 | $CONHNMe_2$ | H |
| 173 | H | 1 | $CONMeNMe_2$ | H |
| 174 | Me | 1 | $CONMeNMe_2$ | H |
| 175 | H | 1 | $CONHNEt_2$ | H |
| 176 | Me | 1 | $CONHNEt_2$ | H |
| 177 | H | 1 | $CONMeNEt_2$ | H |
| 178 | Me | 1 | $CONMeNEt_2$ | H |
| 179 | H | 1 | CONMeN(Me)(Et) | H |
| 180 | Me | 1 | CONMeN(Me)(Et) | H |
| 181 | H | 1 | OH | H |
| 182 | Me | 1 | OH | H |
| 183 | H | 1 | SMe | H |
| 184 | Me | 1 | SMe | H |
| 185 | H | 1 | SEt | H |
| 186 | Me | 1 | SEt | H |
| 187 | H | 1 | S(n)Pr | H |
| 188 | Me | 1 | S(n)Pr | H |
| 189 | H | 1 | S(i)Pr | H |
| 190 | Me | 1 | S(i)Pr | H |
| 191 | H | 1 | $SO_2Me$ | H |
| 192 | Me | 1 | $SO_2Me$ | H |
| 193 | H | 1 | $SO_2Et$ | H |
| 194 | Me | 1 | $SO_2Et$ | H |
| 195 | H | 1 | $SO_2$(n)Pr | H |
| 196 | Me | 1 | $SO_2$(n)Pr | H |
| 197 | H | 1 | $SO_2$(i)Pr | H |
| 198 | Me | 1 | $SO_2$(i)Pr | H |
| 199 | H | 1 | OMe | H |
| 200 | Me | 1 | OMe | H |
| 201 | H | 1 | OEt | H |
| 202 | Me | 1 | OEt | H |
| 203 | H | 1 | O(n)Pr | H |
| 204 | Me | 1 | O(n)Pr | H |
| 205 | H | 1 | O(i)Pr | H |
| 206 | Me | 1 | O(i)Pr | H |
| 207 | H | 1 | OH | CH=NH |

TABLE 14-continued

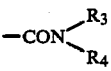

| No. | $R_1$ | n | X | Y |
|---|---|---|---|---|
| 208 | Me | 1 | OH | CH=NH |
| 209 | H | 1 | OH | C=NH, Me |
| 210 | Me | 1 | OH | C=NH, Me |
| 211 | H | 1 | SMe | CH=NH |
| 212 | Me | 1 | SMe | CH=NH |
| 213 | H | 1 | SMe | C=NH, Me |
| 214 | Me | 1 | SMe | C=NH, Me |
| 215 | H | 1 | $SO_2Me$ | CH=NH |
| 216 | Me | 1 | $SO_2Me$ | CH=NH |
| 217 | H | 1 | $SO_2Me$ | C=NH, Me |
| 218 | Me | 1 | $SO_2Me$ | C=NH, Me |
| 219 | H | 1 | OMe | CH=NH |
| 220 | Me | 1 | OMe | CH=NH |
| 221 | H | 1 | OMe | C=NH, Me |
| 222 | Me | 1 | OMe | C=NH, Me |

What is claimed is:

1. A compound of the formula:

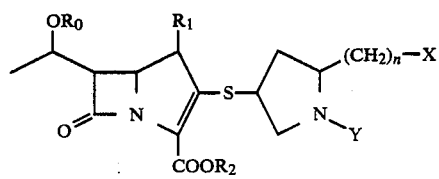

wherein $R_1$ is a hydrogen atom or a lower alkyl group, $R_2$ is a hydrogen atom or a conventional protecting group for a carboxyl group, $R_0$ is a hydrogen atom or a conventional protecting group for a hydroxyl group, X is a protected or unprotected amino group, a carboxyl group, a lower alkoxycarbonyl group, an ar(lower)alkyloxycarbonyl group, a cyano group, a hydroxyl group, a lower alkyloxy group, a lower alkylthio group, a lower alkylsulfonyl group or a group of either one of the following formulas:

 (1)

wherein $R_3$ and $R_4$, which may be the same or different, each represent a hydrogen atom or a lower alkyl group, or they are taken together to represent an alkylene chain to form, in combination with the adjacent nitrogen atom, a 3- to 7-membered cyclic amino group, $$-ZCOR_5 \quad (2)$$

wherein Z represents —NH— or —O— and $R_5$ represents an amino group, a mono(lower)alkylamino group, a di(lower)alkylamino group, a lower alkyloxy group or a lower alkyl group,

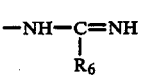 (3)

wherein $R_6$ represents a hydrogen atom or a lower alkyl group, $$-CH=N-R_7 \quad (4)$$

wherein $R_7$ represents a mono(lower)alkylamino group, a di(lower)alkylamino group or a lower alkyloxy group, or

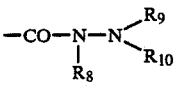 (5)

wherein $R_8$, $R_9$ and $R_{10}$, which may be the same or different, each represent a hydrogen atom or a lower alkyl group, Y represents a hydrogen atom, a conventional protecting group for an amino group or a group of either one of the following formulas:

 (6)

wherein $R_{11}$ and $R_{12}$, which may be the same or different, each represents a hydrogen atom or a lower alkyl group or

 (7)

wherein $R_6$ is as defined above and n is an integer of 1 to 6, and a pharmacologically acceptable salt thereof.

2. A compound as claimed in claim 1, wherein $R_0$ and $R_2$ each are a hydrogen atom and X is an amino group, a carboxyl group, a lower alkoxycarbonyl group, an ar(lower)alkyloxycarbonyl group, a cyano group, a hydroxyl group, a lower alkyloxy group, a lower alkylthio group, a lower alkylsulfonyl group or a group of either one of the following formulas:

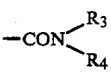 (1)

wherein $R_3$ and $R_4$ are as defined in claim 1,

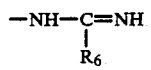 (2)

wherein Z and R$_5$ are as defined in claim 1,

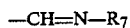 (3)

wherein R$_6$ is as defined in claim 1,

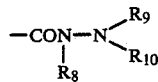 (4)

wherein R$_7$ is as defined in claim 1, or

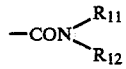 (5)

wherein R$_8$, R$_9$ and R$_{10}$ are as defined in claim 1, and Y is a hydrogen atom or a group of either one of the following formulas:

 (6)

wherein R$_{11}$ and R$_{12}$ are as defined in claim 1, or

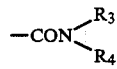 (7)

wherein R$_6$ is as defined in claim 1.

3. A compound as claimed in claim 1, wherein R$_0$ and R$_2$ each are a hydrogen atom, X is a carboxyl group, a lower alkoxycarbonyl group, a cyano group, a hydroxyl group, a lower alkyloxy group or a group of either one of the following formulas:

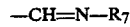 (1)

wherein R$_3$ and R$_4$ are as defined in claim 1,

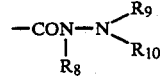 (4)

wherein R$_7$ is as defined in claim 1, or

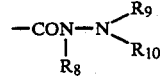 (5)

wherein R$_8$, R$_9$ and R$_{10}$ are as defomed om claim 1, and Y is a hydrogen atom.

4. A compound as claimed in claim 3, wherein X is a group of the formula:

wherein R$_{3a}$ and R$_{4a}$ each represent a hydrogen atom or a methyl group.

5. A compound as claimed in claim 3, wherein X is a hydroxyl group or a lower alkyloxy group.

6. A compound as claimed in any one of claims 1 to 5, wherein R$_1$ is a methyl group.

7. A compound as claimed in claim 6, which has a (5S)-configuration.

8. A compound as claimed in claim 7, which has a (4R,5S,6S,8R)-configuration.

9. A compound as claimed in claim 3, wherein R$_1$ is a hydrogen atom.

10. A compound as claimed in claim 9, which has a (5R)-configuration.

11. A compound as claimed in claim 10, which has a (5R,6S,8R)-configuration.

12. A compound as claimed in claim 1, which is (4R,5S,6S,8R,2'R,4'S)-3-[(2-dimethylaminocarbonylmethyl-pyrrolidin)-4-ylthio]-4-methyl-6-(1-hydroxyethyl)-1-azabicyclo[3.2.0]-hept-2-en-7-one-2-carboxylic acid, or a salt thereof.

13. A compound as claimed in claim 1, which is (4R,5S,6S,8R,2'R,4'S)-3-[(2-methylaminocarbonylmethyl-pyrrolidin)-4-ylthio]-4-methyl-6-(1-hydroxyethyl)-1-azabicyclo[3.2.0]-hept-2-en-7-one-2-carboxylic acid, or a salt thereof.

14. A compound as claimed in claim 1, which is (4R,5S,6S,8R,2'R,4'S)-3-[(2-carbamoylmethylpyrrolidin)-4-ylthio]-4-methyl-6-(1-hydroxyethyl)-1-azabicyclo[3.2.0]-hept-2-en-7-one-2-carboxylic acid, or a salt thereof.

15. A compound as claimed in claim 1, which is (4R,5S,6S,8R,2'R,4'S)-3-[(2-(2-dimethylaminocarbonylethyl)-pyrrolidin)-4-ylthio]-4-methyl-6-(1-hydroxyethyl)-1-azabicyclo[3.2.0]-hept-2-en-7-one-2-carboxylic acid, or a salt thereof.

16. A compound as claimed in claim 1, which is (4R,5S,6S,8R,2'R,4'S)-3-[(2-(2-methylaminocarbonylethyl)-pyrrolidin)-4-ylthio]-4-methyl-6-(1-hydroxyethyl)-1-azabicyclo[3.2.0]-hept-2-en-7-one-2-carboxylic acid, or a salt thereof.

17. A compound as claimed in claim 1, which is (4R,5S,6S,8R,2'R,4'S)-3-[(2-(2-carbamoylethyl)pyrrolidin)-4-ylthio]-4-methyl-6-(1-hydroxyethyl)-1-azabicyclo[3.2.0]-hept-2-en-7-one-2-carboxylic acid, or a salt thereof.

18. A compound as claimed in claim 1, which is (4R,5S,6S,8R,2'S,4'S)-3-[(2-hydroxymethylpyrrolidin)-4-ylthio]-4-methyl-6-(1-hydroxyethyl)-1-azabicyclo[3.2.0]-hept-2-en-7-one-2-carboxylic acid, or a salt thereof.

19. A compound as claimed in claim 1, which is (4R,5S,6S,8R,2'S,4'S)-3-[2-methoxymethylpyrrolidin)-4-ylthio]-4-methyl-6-(1-hydroxyethyl)-1-azabicyclo[3.2.0]-hept- 2-en-7-one-2-carboxylic acid, or a salt thereof.

20. A compound as claimed in claim 1, which is (4R,5S,6S,8R,2'R,4'S)-3-[(2-(2-carboxyethyl)pyrrolidin)-4-ylthio]-4-methyl-6-(1-hydroxyethyl)-1-azabicyclo-[3.2.0]-hept-2-en-7-one-2-carboxylic acid, or a salt thereof.

21. A compound as claimed in claim 1, which is (4R,-5S,6S,8R,2'R,4'S)-3-[(2-methoxycarbonylmethylpyrrolidin)-4-ylthio]-4-methyl-6-(1-hydroxyethyl)-1-azabicyclo[3.2.0]-hept-2-en-7-one-2-carboxylic acid, or a salt thereof.

22. A compound as claimed in claim 1, which is (4R,5S,6S,8R,2'R,4'S)-3-[(2-(2-N,N-dimethylhydrazonoethyl)pyrrolidin)-4-ylthio]-4-methyl-6-(1-hydroxyethyl)1-azabicyclo[3.2.0]-hept-2-en-7-one-2-carboxylic acid, or a salt thereof.

23. A pharmaceutical composition for antimicrobial use which comprises as an active ingredient a pharmaceutically effective amount of a compound according to claim 1, and at least one pharmaceutically acceptable inert carrier or diluent.

24. A pharmaceutical composition for antimicrobial which comprises as an active ingredient a pharmaceutically effective amount of a compounding according to claim 2, and at least one pharmaceutically acceptable carrier or diluent.

25. A method for treating an infectious disease caused by bacteria, which comprises administering an effective amount of a compound according to claim I as an antimicrobial agent to a patient suffering from said disease caused by bacteria.

26. A compounding according to claim 1, which is represented by the formula:

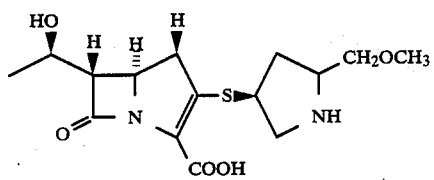

27. A compound according to claim 1, which is represented by the formula:

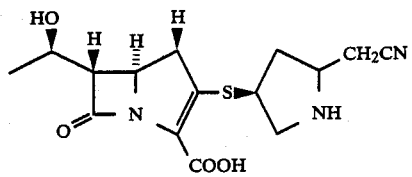

28. A compound according to claim 1, which is represented by the formula:

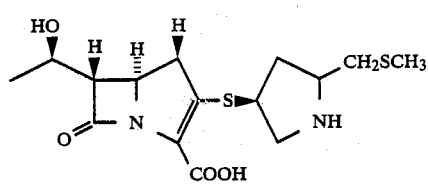

29. A compound according to claim 1, which is represented by the formula:

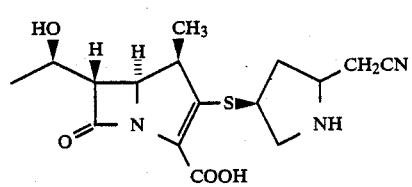

* * * * *